US012623997B2

(12) United States Patent
Faler et al.

(10) Patent No.: US 12,623,997 B2
(45) Date of Patent: May 12, 2026

(54) NON-COORDINATING ANION ACTIVATORS CONTAINING A CATION WITH LONG CHAIN ALKOXY FUNCTIONALIZATION

(71) Applicant: ExxonMobil Chemical Patents Inc., Baytown, TX (US)

(72) Inventors: Catherine A. Faler, Houston, TX (US); Margaret T. Whalley, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 895 days.

(21) Appl. No.: 17/771,344

(22) PCT Filed: Aug. 4, 2020

(86) PCT No.: PCT/US2020/044865

§ 371 (c)(1),
(2) Date: Apr. 22, 2022

(87) PCT Pub. No.: WO2021/086467

PCT Pub. Date: May 6, 2021

(65) Prior Publication Data

US 2022/0388946 A1 Dec. 8, 2022

Related U.S. Application Data

(60) Provisional application No. 62/926,956, filed on Oct. 28, 2019.

(51) Int. Cl.

| | |
|---|---|
| ***C07C 217/52*** | (2006.01) |
| ***C07C 217/84*** | (2006.01) |
| ***C07F 5/02*** | (2006.01) |
| ***C07F 7/00*** | (2006.01) |
| ***C07F 17/00*** | (2006.01) |
| ***C08F 4/659*** | (2006.01) |
| ***C08F 10/00*** | (2006.01) |
| ***C08F 110/02*** | (2006.01) |
| ***C08F 110/06*** | (2006.01) |
| ***C08F 210/14*** | (2006.01) |
| ***C08F 210/16*** | (2006.01) |

(52) U.S. Cl.
CPC ............ *C07C 217/52* (2013.01); *C08F 4/659* (2013.01)

(58) Field of Classification Search
CPC . C07C 217/52; C07C 217/84; C08F 2420/10; C08F 210/16; C08F 210/14; C08F 2500/03; C08F 2500/27; C08F 2500/034; C08F 110/02; C08F 110/06; C07F 7/00; C07F 17/00; C07F 5/02; C07F 5/027
See application file for complete search history.

(56) References Cited

U.S. PATENT DOCUMENTS

| | | | |
|---|---|---|---|
| 6,121,185 | A | 9/2000 | Rosen |
| 7,101,940 | B2 | 9/2006 | Schottek et al. |
| 7,223,822 | B2 | 5/2007 | Abhari |
| 7,332,551 | B2 | 2/2008 | Rodriguez et al. |
| 8,658,556 | B2 | 2/2014 | Stewart |
| 8,859,696 | B2 | 10/2014 | Hanton |
| 9,035,119 | B2 | 5/2015 | Ewart |
| 9,611,280 | B2 | 4/2017 | Takaishi et al. |
| 11,414,436 | B2 | 8/2022 | Faler |
| 2006/0247483 | A1 | 11/2006 | McConville et al. |
| 2008/0220193 | A1 | 9/2008 | Tohi |
| 2009/0286944 | A1 | 11/2009 | Ackerman et al. |
| 2012/0316302 | A1 | 12/2012 | Stewart |
| 2012/0316303 | A1 | 12/2012 | Hanton et al. |
| 2014/0039141 | A1 | 2/2014 | Giesbrecht et al. |
| 2014/0087987 | A1 | 3/2014 | Crowther et al. |
| 2019/0330139 | A1 | 10/2019 | Faler et al. |

FOREIGN PATENT DOCUMENTS

| | | |
|---|---|---|
| JP | 2010-176930 | 8/2010 |
| JP | 2011-225650 | 11/2011 |
| JP | 2013089618 | 5/2013 |
| WO | 2001042249 A1 | 6/2001 |
| WO | 2012/170202 | 12/2012 |
| WO | 2018022219 A1 | 2/2018 |
| WO | 2021/025903 | 2/2021 |

OTHER PUBLICATIONS

Masoud Samet, et al.(2015) "Charge-Enhanced Acidity and Catalyst Activation", ACS Publications, J. Am. Chem. Soc 2015, v 137, pp. 4678-4680.

*Primary Examiner* — Sun Jae Yoo
(74) *Attorney, Agent, or Firm* — Fletcher Yoder P.C.

(57) ABSTRACT

Activators may comprise compounds represented by the Formula $[Ar(EHR^1R^2)(OR^3)]d+[M^{k+}Q_n]^d$, wherein: Ar is an aryl group; E is nitrogen or phosphorous; $R^1$ is a $C_1$-$C_{30}$, optionally substituted, linear alkyl group; $R^2$ is a $C_1$-$C_{30}$, optionally substituted, linear alkyl group; $R^3$ is a $C_{10}$-$C_{30}$, optionally substituted, linear alkyl group; M is an element selected from group 13 of the Periodic Table of the Elements; d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical. Catalysts systems may comprise these activators and methods of preparing polyolefins may use these catalysts systems.

19 Claims, 1 Drawing Sheet

NON-COORDINATING ANION ACTIVATORS CONTAINING A CATION WITH LONG CHAIN ALKOXY FUNCTIONALIZATION

CROSS-REFERENCE TO RELATED APPLICATION

This application is a U.S. national phase application of PCT Application No. PCT/US2020/044865 having a filing date of Aug. 4, 2020, which claims priority to and the benefit of U.S. Provisional Application No. 62/926,956 having a filing date of Oct. 28, 2019, the contents of both are incorporated by reference in their entirety.

FIELD

This application relates to group 13 metallate activators, catalyst systems comprising the activators, and methods for polymerizing olefins using such activators.

BACKGROUND

Polyolefins are widely used commercially because of their robust physical properties. Polyolefins are typically prepared with a catalyst that polymerizes olefin monomers. Therefore, there is interest in finding new catalysts and catalyst systems that provide polymers having improved properties.

Catalysts for olefin polymerization are often based on metallocenes as catalyst precursors, which are activated either with an alumoxane or an activator containing a non-coordinating anion. A non-coordinating anion, such as tetrakis(pentafluorophenyl)borate, is capable of stabilizing the resulting metal cation of the catalyst. Because such activators are fully ionized and the corresponding anion is highly non-coordinating, such activators can be effective as olefin polymerization catalyst activators. However, because they are ionic salts, such activators are frequently insoluble in aliphatic hydrocarbons and only sparingly soluble in aromatic hydrocarbons. It is desirable to conduct most polymerizations of α-olefins in aliphatic hydrocarbon solvents due to the compatibility of such solvents with the olefin monomer and in order to reduce the aromatic hydrocarbon content of the resulting polymer product. Typically, ionic salt activators are added to such polymerizations in the form of a solution in an aromatic solvent such as toluene. The use of even a small quantity of such an aromatic solvent for this purpose is undesirable since it must be removed in a post-polymerization devolatilization step and separated from other volatile components, which is a process that adds significant cost and complexity to any commercial process. In addition, the activators often exist in the form of an oily, intractable material which is not readily handled and metered or precisely incorporated into the reaction mixture.

There is a need for activators that are soluble in aliphatic hydrocarbon solvents and capable of producing polyolefins at high activity levels. In particular, there is a need for activators that may be economically prepared and possessing solubilities eliminating the need to use aromatic solvents in the polymerization process.

It is therefore an object of the present invention to provide activators, catalyst systems comprising these activators, and methods for the polymerization of olefins using such activators and catalyst systems.

SUMMARY

Activators described herein may comprise a compound represented by Formula (I):

$$[Ar(EHR^1R^2)(OR^3)]_d^+[M^{k+}Q_n]^{d-} \quad (I)$$

wherein:

Ar is an aryl group;

E is nitrogen or phosphorous;

$R^1$ is a $C_1$-$C_{30}$, optionally substituted, linear alkyl group;

$R^2$ is a $C_1$-$C_{30}$, optionally substituted, linear alkyl group;

$R^3$ is a $C_{10}$-$C_{30}$, optionally substituted, linear alkyl group;

M is an element selected from group 13 of the Periodic Table of the Elements;

d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Activators described herein may also comprise a compound represented by Formula (II):

$$[Cat]^+[MQ_4]^- \quad (II)$$

wherein:

M is an element selected from group 13 of the Periodic Table of the Elements;

Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical; and $[Cat]^+$ is a cation represented by a structure selected from the group consisting of

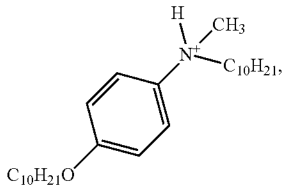

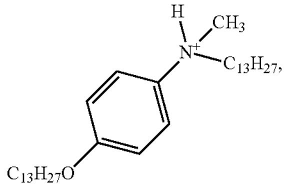

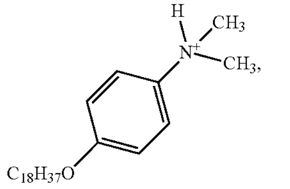

and

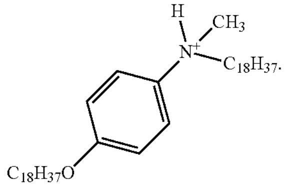

Activators described herein may also comprise a compound represented by Formula (III):

$$[R^{11}R^{12}R^{13}EH]^+[BR^{14}R^{15}R^{16}R^{17}]^- \quad (II)$$

wherein:

E is nitrogen or phosphorous;

each of $R^{11}$, $R^{12}$, and $R^{13}$ is independently a $C_1$-$C_{30}$ linear alkyl group or an aryl group, wherein the aryl group is substituted with at least one $C_{10}$-$C_{30}$ alkoxy group, wherein $R^{11}$, $R^{12}$, and $R^{13}$ together comprise 26 or more carbon atoms; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

Catalyst systems described herein may comprise an activator as described herein and a catalyst compound represented by Formula (IV):

(IV)

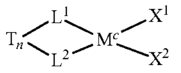

wherein in Formula (IV):

$M^c$ is an element selected from group 4 of the Periodic Table of the Elements;

n is 0 or 1;

T is an optional bridging group selected from S, O, PR', NR', $SiR''_2$, $CH_2$, CHR", or $CR''_2$, wherein R' is a $C_1$-$C_{30}$, optionally substituted, hydrocarbyl group and R" is hydrogen or a $C_1$-$C_{30}$, optionally substituted, hydrocarbyl group;

$L^1$ and $L^2$ are independently cyclopentadienyl, substituted cyclopentadienyl, indenyl, substituted indenyl, tetrahydroindenyl, substituted tetrahydroindenyl, fluorenyl, or substituted fluorenyl groups; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Catalyst systems described herein may comprise an activator as described herein and a catalyst compound represented by Formula (V):

(V)

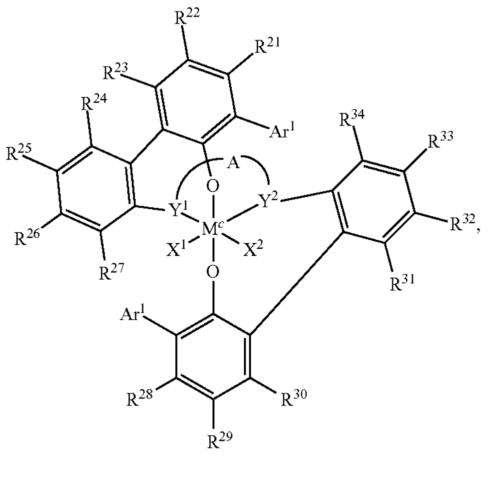

wherein in Formula (IV):

$M^c$ is an element selected from group 4 of the Periodic Table of the Elements;

$R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ are independently hydride, halide, optionally substituted hydrocarbyl, heteroatom-containing optionally substituted hydrocarbyl, alkoxy, aryloxy, silyl, boryl, dialkyl amino, alkylthio, arylthio and seleno: optionally two or more R groups can combine together into ring structures with such ring structures having from 3 to 100 non-hydrogen atoms in the ring;

A is a $C_1$-$C_{50}$ alkyl group;

$Y^1$ and $Y^2$ are independently selected from O, S, $NR^a$ and $PR^a$ wherein $R^a$ is optionally substituted hydrocarbyl;

$Ar^1$ is phenyl, naphthyl, biphenyl, anthracenyl, or phenanthrenyl; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, alkylaryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Catalyst systems described herein may comprise an activator as described herein and a catalyst compound represented by Formulas (VIa) or (VIb):

(VIa)

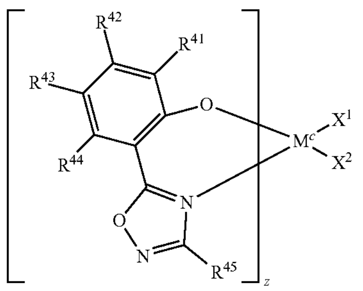

(VIb)

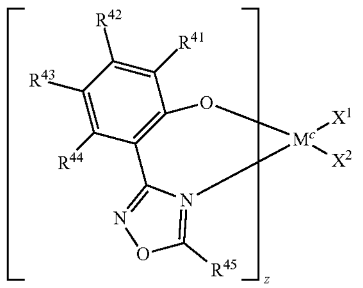

wherein in Formulas (VIa) or (VIb):

$M^c$ is an element selected from group 4 of the Periodic Table of the Elements $R^{41}$, $R^{42}$, $R^{43}$, $R^{44}$, $R^{45}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand; and z is 1, 2, 3, or 4.

Catalyst systems described herein may comprise an activator as described herein and a catalyst compound represented by Formula (VII):

(VII)

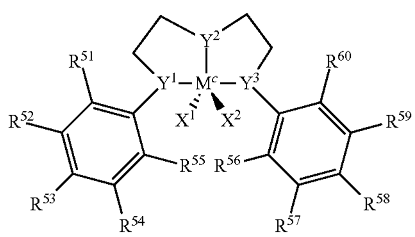

wherein in Formula (VII):

$M^c$ is an element selected from group 4 of the Periodic Table of the Elements $R^{51}$, $R^{52}$, $R^{53}$, $R^{54}$, $R^{55}$, $R^{56}$, $R^{57}$, $R^{58}$, $R^{59}$, $R^{60}$ are independently selected from the group consisting of hydrogen, alkyl, substituted alkyl, cycloakyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amnion, thioalkyl, thioaryl, nitro, and combinations thereof;

$Y^1$ and $Y^2$ are independently O, N, NH, or S; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Polymerization methods disclosed herein may comprise a) contacting one or more olefin monomers with a catalyst system comprising: i) an activator as described herein, ii) a catalyst compound, and iii) optional support.

BRIEF DESCRIPTION OF THE FIGURES

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
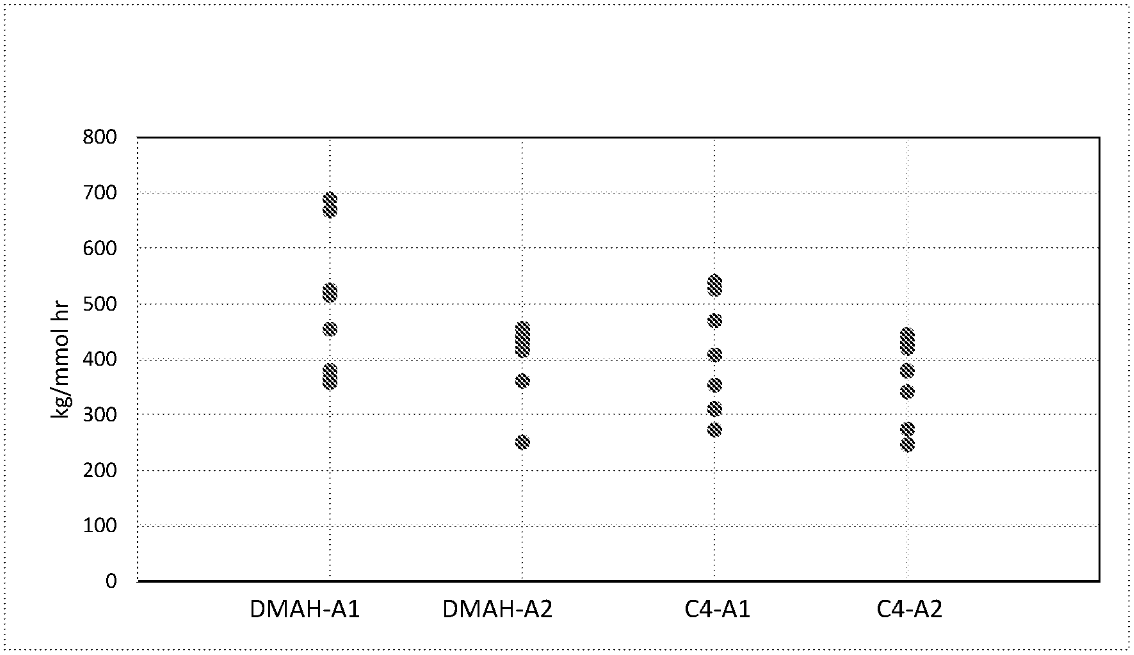
FIG. 1 is a graph illustrating the catalyst activity data for examples in Table 1.

This application relates to group 13 metallate activators, catalyst systems comprising the activators, and methods for polymerizing olefins using such activators and, more particularly, activators that are soluble in aliphatic solvents.

To facilitate an understanding of the present invention, a number of terms and phrases are defined below.

Definitions

Unless otherwise noted all melt temperatures (Tm) are DSC second melt and are determined using the following DSC procedure according to ASTM D3418-03. Differential scanning calorimetric (DSC) data are obtained using a TA Instruments model Q200 machine. Samples weighing about 5 to about 10 mg are sealed in an aluminum hermetic sample pan. The DSC data are recorded by first gradually heating the sample to about 200° C. at a rate of about 10° C./minute. The sample is kept at about 200° C. for about 2 minutes, then cooled to about −90° C. at a rate of about 10° C./minute, followed by an isothermal for about 2 minutes and heating to about 200° C. at about 10° C./minute. Both the first and second cycle thermal events are recorded. The melting points reported herein are obtained during the second heating/cooling cycle unless otherwise noted.

All molecular weights are weight average (Mw) unless otherwise noted. All molecular weights are reported in g/mol unless otherwise noted. Unless otherwise indicated, measurements of weight average molecular weight (Mw) are determined by the Gel Permeation Chromatography (GPC) procedure as described in US 2006/0173123 page 24-25, paragraphs [0334] to [0341]; each of which is fully incorporated herein by reference for US purposes. Melt index (MI) also referred to as 12, reported in g/10 min., is determined according to ASTM D-1238, 190° C., 2.16 kg load. High load melt index (HLMI) also referred to as 121, reported in g/10 min., is determined according to ASTM D-1238, 190° C., 21.6 kg load. Melt index ratio (MIR) is MI divided by HLMI as determined by ASTM D1238.

The specification describes catalysts that can be transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides). Under this scheme, the term "transition metal" refers to any atom from Groups 3-12 of the Periodic Table, inclusive of the lanthanides and actinide elements. Ti, Zr, and Hf are Group 4 transition metals, for example.

The following abbreviations are used through this specification: o-biphenyl is an ortho-biphenyl moiety represented by the structure

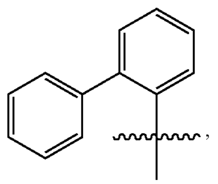 [SMILES: *c1ccccc1-c1ccccc1]

dme is 1,2-dimethoxyethane, Me is methyl, Ph is phenyl, Et is ethyl, Pr is propyl, iPr is isopropyl, n-Pr is normal propyl, cPr is cyclopropyl, Bu is butyl, iBu is isobutyl, tBu is tertiary butyl, p-tBu is para-tertiary butyl, nBu is normal butyl, sBu is sec-butyl, TMS is trimethylsilyl, TIBAL is triisobutylaluminum, TNOAL is tri(n-octyl)aluminum, MAO is methylalumoxane, p-Me is para-methyl, Ph is phenyl, Bn is benzyl (i.e., $CH_2Ph$), THF (also referred to as thf) is tetrahydrofuran, RT is room temperature (and is 23° C. unless otherwise indicated), tol is toluene, EtOAc is ethyl acetate, MeCy is methylcyclohexane, and Cy is cyclohexyl.

Unless otherwise indicated (e.g., the definition of "substituted hydrocarbyl," "substituted aromatic," etc.), the term "substituted" means that at least one hydrogen atom has been replaced with at least a non-hydrogen group, such as a hydrocarbyl group, a heteroatom, or a heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a ring structure.

The terms "hydrocarbyl radical," "hydrocarbyl," and "hydrocarbyl group," are used interchangeably throughout this application. Likewise, the terms "group", "radical", and "substituent" may be used interchangeably and are defined to mean a group consisting of hydrogen and carbon atoms only. Preferred hydrocarbyls are $C_1$-$C_{100}$ radicals that may be linear, branched, or cyclic, and when cyclic, aromatic or non-aromatic. Examples of such radicals include, but are not limited to, alkyl groups such as methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like, aryl groups, such as phenyl, benzyl naphthyl, and the like.

Substituted hydrocarbyl radicals are radicals in which at least one hydrogen atom of the hydrocarbyl radical has been replaced with a heteroatom, or a heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring.

Substituted cyclopentadienyl, indenyl, tetrahydroindenyl or fluorenyl groups are cyclopentadienyl, indenyl, tetrahydroindenyl or fluorenyl groups where at least one hydrogen atom has been replaced with at least a non-hydrogen group, such as a hydrocarbyl group, a heteroatom, or a heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a ring structure.

Halocarbyl radicals (also referred to as halocarbyls, halocarbyl groups or halocarbyl substituents) are radicals in which one or more hydrocarbyl hydrogen atoms have been substituted with at least one halogen (e.g., F, Cl, Br, I) or halogen-containing group (e.g., CAT-2). Substituted halocarbyl radicals are radicals in which at least one halocarbyl hydrogen or halogen atom has been substituted with at least one functional group such as NR*2, OR*, SeR*, TeR*, $PR^*_2$, $AsR^*_2$, $SbR^*_2$, SR*, $BR^*_2$, $SiR^*_3$, $GeR^*_3$, $SnR^*_3$, $PbR^*_3$, and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —$Si(R^*)_2$—, —$Ge(R^*)_2$—, —$Sn(R^*)_2$—, —$Pb(R^*)_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Hydrocarbylsilyl groups, also referred to as silylcarbyl groups, are radicals in which one or more hydrocarbyl hydrogen atoms have been substituted with at least one $SiR^*_3$ containing group or where at least one —$Si(R^*)_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Silylcarbyl radicals can be bonded via a silicon atom or a carbon atom.

Substituted silylcarbyl radicals are silylcarbyl radicals in which at least one hydrogen atom has been substituted with at least one functional group such as $NR^*_2$, OR*, SeR*, TeR*, $PR^*_2$, $AsR^*_2$, $SbR^*_2$, SR*, $BR^*_2$, $GeR^*_3$, $SnR^*_3$, $PbR_3$ and the like or where at least one non-hydrocarbon atom or group has been inserted within the silylcarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —$Ge(R^*)_2$—, —$Sn(R^*)_2$—, —$Pb(R^*)_2$— and the like, where R* is independently a hydrocarbyl or halocarbyl radical, and two or more R* may join together to form a substituted or unsubstituted saturated, partially unsaturated or aromatic cyclic or polycyclic ring structure.

Germylcarbyl radicals (also referred to as germylcarbyls, germylcarbyl groups or germylcarbyl substituents) are radicals in which one or more hydrocarbyl hydrogen atoms have been substituted with at least one $GeR^*_3$ containing group or where at least one —$Ge(R^*)_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Germylcarbyl radicals can be bonded via a germanium atom or a carbon atom.

Substituted germylcarbyl radicals are germylcarbyl radicals in which at least one hydrogen atom has been substituted with at least one functional group such as $NR^*_2$, OR*, SeR*, TeR*, $PR^*_2$, $AsR^*_2$, $SbR^*_2$, SR*, $BR^*_2$, $SiR^*_3$, $SnR^*_3$, $PbR_3$ and the like or where at least one non-hydrocarbon atom or group has been inserted within the germylcarbyl radical, such as —O—, —S—, —Se—, —Te—, —N(R*)—, ═N—, —P(R*)—, ═P—, —As(R*)—, ═As—, —Sb(R*)—, ═Sb—, —B(R*)—, ═B—, —$Si(R^*)_2$—, —$Sn(R^*)_2$—, —$Pb(R^*)_2$— and the like, where R* is independently a hydrocarbyl or halocarbyl radical, and two or more R* may join together to form a substituted or unsubstituted saturated, partially unsaturated or aromatic cyclic or polycyclic ring structure.

The terms "alkyl radical," and "alkyl" are used interchangeably throughout this application. For purposes of this application, "alkyl radicals" are defined to be $C_1$-$C_{100}$ alkyls that may be linear, branched, or cyclic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like. Substituted alkyl radicals are radicals in which at least one hydrogen atom of the alkyl radical has been substituted with at least a non-hydrogen group, such as a hydrocarbyl group, a heteroatom, or a heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring.

The term "branched alkyl" means that the alkyl group contains a tertiary or quaternary carbon (a tertiary carbon is a carbon atom bound to three other carbon atoms. A quaternary carbon is a carbon atom bound to four other carbon atoms). For example, 3,5,5 trimethylhexylphenyl is an alkyl group (hexyl) having three methyl branches (hence, one tertiary and one quaternary carbon) and thus is a branched alkyl bound to a phenyl group.

The term "alkenyl" means a straight-chain, branched-chain, or cyclic hydrocarbon radical having one or more carbon-carbon double bonds. These alkenyl radicals may be substituted. Examples of suitable alkenyl radicals can include ethenyl, propenyl, allyl, 1,4-butadienyl cyclopropenyl, cyclobutenyl, cyclopentenyl, cyclohexenyl, cyclooctenyl and the like.

The term "arylalkenyl" means an aryl group where a hydrogen has been replaced with an alkenyl or substituted alkenyl group. For example, styryl indenyl is an indene substituted with an arylalkenyl group (a styrene group).

The term "alkoxy", "alkoxyl", or "alkoxide" mean an alkyl group bound to an oxygen atom, such as an alkyl ether or aryl ether group/radical and can include those where the alkyl group is a $C_1$ to $C_{10}$ hydrocarbyl. The alkyl group may be straight chain, branched, or cyclic. The alkyl group may be saturated or unsaturated. Examples of suitable alkoxy and radicals can include methoxy, ethoxy, n-propoxy, iso-propoxy, n-butoxy, iso-butoxy, sec-butoxy, tert-butoxy, and the like.

The term "aryloxy" or "aryloxide" means an aryl group bound to an oxygen atom, such as an aryl ether group/radical wherein the term aryl is as defined herein. Examples of suitable aryloxy radicals can include phenoxyl, and the like.

The term "aryl" or "aryl group" means a carbon-containing aromatic ring such as phenyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic.

Heterocyclic means a cyclic group where a ring carbon atom (or two or three ring carbon atoms) has been replaced with a heteroatom, such as N, O, or S. A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

Substituted heterocyclic means a heterocyclic group where at least one hydrogen atom of the heterocyclic radical has been substituted with at least a non-hydrogen group, such as a hydrocarbyl group, a heteroatom, or a heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl or halocarbyl radical.

A substituted aryl is an aryl group where at least one hydrogen atom of the aryl radical has been substituted with at least a non-hydrogen group, such as a hydrocarbyl group, a heteroatom, or a heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring, for example 3,5-dimethylphenyl is a substituted aryl group.

The term "substituted phenyl," or "substituted phenyl group" means a phenyl group having one or more hydrogen groups replaced by a hydrocarbyl, substituted hydrocarbyl, heteroatom or heteroatom containing group, such as halogen (such as Br, Cl, F or I) or at least one functional group such as —$NR^*_2$, —OR*, —SeR*, —TeR*, —$PR^*_2$, —$AsR^*_2$, —$SbR^*_2$, —SR*, —$BR^*_2$, —SiR*, —$SiR^*_3$, —GeR*, —$GeR^*_3$, —SnR*, —$SnR^*_3$, —$PbR^*_3$, and the like, where each R* is independently a hydrocarbyl, halogen, or halocarbyl radical. Preferably the "substituted phenyl" group is represented by the formula:

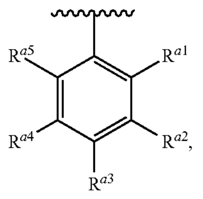

where each of $R^{a1}$, $R^{a2}$, $R^{a3}$, $R^{a4}$, and $R^{a}$ is independently selected from hydrogen, $C_1$-$C_{40}$ hydrocarbyl or $C_1$-$C_{40}$ substituted hydrocarbyl, a heteroatom, such as halogen, or a heteroatom-containing group (provided that at least one of $R^{a1}$, $R^{a2}$, $R^{a3}$, $R^{a4}$, and $R^{a5}$ is not H), or two or more of $R^{a1}$, $R^{a2}$, $R^{a3}$, $R^{a4}$, and $R^{a5}$ are joined together to form a $C_4$-$C_{62}$ cyclic or polycyclic ring structure, or a combination thereof.

The term "substituted naphthyl," means a naphthyl group having 1 or more hydrogen groups replaced by a hydrocarbyl, substituted hydrocarbyl, heteroatom or heteroatom containing group.

A "fluorophenyl" or "fluorophenyl group" is a phenyl group substituted with one, two, three, four or five fluorine atoms.

The term "substituted fluorenyl" means a fluorenyl group having 1 or more hydrogen groups replaced by a hydrocarbyl, substituted hydrocarbyl, heteroatom or heteroatom containing group.

The term "arylalkyl" means an aryl group where a hydrogen has been replaced with an alkyl or substituted alkyl group. For example, 3,5'-di-tert-butyl-phenyl indenyl is an indene substituted with an arylalkyl group. When an arylalkyl group is a substituent on another group, it is bound to that group via the aryl. For example, the aryl portion may be bound to E.

The term "alkylaryl" means an alkyl group where a hydrogen has been replaced with an aryl or substituted aryl group. For example, phenethyl indenyl is an indene substituted with an ethyl group bound to a benzene group. When an alkylaryl group is a substituent on another group, it is bound to that group via the alkyl. For example, the alkyl portion may be bound to E.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl), unless otherwise indicated.

The term "ring atom" means an atom that is part of a cyclic ring structure. Accordingly, a benzyl group has six ring atoms and tetrahydrofuran has 5 ring atoms.

As used herein, and unless otherwise specified, the term "$C_n$" means hydrocarbon(s) having n carbon atom(s) per molecule, wherein n is a positive integer.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. Likewise, a "Cm-Cy" group or compound refers to a group or compound comprising carbon atoms at a total number thereof in the range from m to y. Thus, a $C_1$-$C_{50}$ alkyl group refers to an alkyl group comprising carbon atoms at a total number thereof in the range from 1 to 50.

For purposes of the present disclosure, a "catalyst system" is a combination of at least one catalyst compound, an activator, and an optional support material. The catalyst systems may further comprise one or more additional catalyst compounds. For the purposes of the present disclosure, when catalyst systems are described as comprising neutral stable forms of the components, it is well understood by one of ordinary skill in the art, that the ionic form of the component is the form that reacts with the monomers to produce polymers. Catalysts of the presented application and activators represented by Formula (I), (II), and (III) are intended to embrace ionic forms in addition to the neutral forms of the compounds.

"Complex" as used herein, is also often referred to as catalyst precursor, precatalyst, catalyst, catalyst compound, transition metal compound, or transition metal complex. These words are used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

In the description herein, a catalyst may be described as a catalyst precursor, a precatalyst compound, a catalyst compound or a transition metal compound, and these terms are used interchangeably. A polymerization catalyst system is a catalyst system that can polymerize monomers into polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one it-bound cyclopentadienyl moiety or substituted cyclopentadienyl moiety (such as substituted or unsubstituted Cp, Ind, or Flu) and more frequently two (or three) π-bound cyclopentadienyl moieties or substituted cyclopentadienyl moieties (such as substituted or unsubstituted Cp, Ind, or Flu). (Cp=cyclopentadienyl, Ind=indenyl, Flu=fluorenyl).

For purposes of the present disclosure, in relation to catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

"Catalyst productivity" is a measure of how many grams of polymer (P) are produced using a polymerization catalyst comprising W g of catalyst (cat), over a period of time of T hours; and may be expressed by the following formula: P/(T×W) and expressed in units of $gPgcat^{-1}$ $hr^{-1}$. "Conversion" is the amount of monomer that is converted to polymer product, and is reported as mol % and is calculated based on the polymer yield and the amount of monomer fed into the reactor. "Catalyst activity" is a measure of the level of activity of the catalyst and is reported as the mass of product polymer (P) produced per mole (or mmol) of catalyst (cat) used (kgP/molcat or gP/mmolCat), and catalyst activity can also be expressed per unit of time, for example, per hour (hr), e.g., (Kg/mmol h).

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. Accordingly, the definition of copolymer, as used herein, includes terpolymers and the like. "Different" as used to refer to mer units indicates that the mer units differ from each other by at least one atom or are different isomerically. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn.

The term "continuous" means a system that operates without interruption or cessation for a period of time, such as where reactants are continually fed into a reaction zone and products are continually or regularly withdrawn without stopping the reaction in the reaction zone. For example, a continuous process to produce a polymer would be one where the reactants are continually introduced into one or more reactors and polymer product is continually withdrawn.

A "solution polymerization" means a polymerization process in which the polymerization is conducted in a liquid polymerization medium, such as an inert solvent or monomer(s) or their blends. A solution polymerization is typically homogeneous. A homogeneous polymerization is one where the polymer product is dissolved in the polymerization medium. Such systems are typically not turbid as described in Oliveira, J. V. et al. (2000) "High-Pressure Phase Equilibria for Polypropylene-Hydrocarbon Systems," *Ind. Eng. Chem. Res*., v.39, pp. 4627-4633.

A bulk polymerization means a polymerization process in which the monomers and/or comonomers being polymerized are used as a solvent or diluent using little or no inert solvent or diluent. A small fraction of inert solvent might be used as a carrier for catalyst and scavenger. A bulk polymerization system contains less than about 25 wt % of inert solvent or diluent, such as less than about 10 wt %, such as less than about 1 wt %, such as 0 wt %.

DESCRIPTION

The present disclosure relates to activator compounds that can be used in olefin polymerization processes. For example, the present disclosure provides activators, catalyst systems comprising catalyst compounds and activators, and methods for polymerizing olefins using said catalyst systems. In the present disclosure, activators are described that feature ammonium or phosphonium groups with long-chain aliphatic hydrocarbyl groups and long-chain aliphatic ether groups for improved solubility of the activator in aliphatic solvents, as compared to conventional activator compounds.

The present disclosure relates to activator compounds (activators) that can be used in olefin polymerization processes. For example, in some aspects, the present disclosure provides ammonium borate activators, catalyst systems comprising ammonium borate activators, and methods for polymerizing olefins using ammonium borate activators. In the present disclosure, activators are described that feature ammonium groups with long-chain aliphatic hydrocarbyl groups and long-chain aliphatic ether groups for improved solubility of the activator in aliphatic solvents, as compared to conventional activator compounds. Useful borate groups of the present disclosure include fluoronaphthyl borates and fluorophenyl borates, as non-limiting examples. It has been discovered that activators of the present disclosure having fluoronaphthyl borate and fluorophenyl borate anions have improved solubility in aliphatic solvents, as compared to conventional activator compounds. Activators of the present disclosure can provide polyolefins having a weight average molecular weight (Mw) of about 50,000 g/mol or greater and a melt temperature (Tm) of about 50° C. or greater.

In another aspect, the present disclosure relates to polymer compositions obtained from the catalyst systems and processes set forth herein. The components of the catalyst systems according to the present disclosure and used in the polymerization processes of the present disclosure, as well as the resulting polymers, are described in more detail herein below.

The present disclosure relates to catalyst systems comprising a transition metal compound and an activator compound of Formula (I), (II), or (III), to the use of an activator compound of Formula (I), (II), or (III) for activating a transition metal compound in a catalyst system for polymerizing olefins, and to processes for polymerizing olefins, the process comprising contacting, under polymerization conditions, one or more olefins with a catalyst system comprising a transition metal compound and an activator compound of Formula (I), (II), or (III).

The present disclosure also relates to processes for polymerizing olefins comprising contacting, under polymerization conditions, one or more olefins with a catalyst system comprising a transition metal compound and an activator compound of Formula (I), (II), or (III). The weight average molecular weight of the polymer formed can increase with increasing monomer conversion at a given reaction temperature.

The activator compounds of Formula (I), (II), or (III) will be further illustrated below. Any combinations of cations and non-coordinating anions disclosed herein are suitable to be used in the processes of the present disclosure and are thus incorporated herein.

Non-Coordinating Anion (NCA) Activators

Non-coordinating anion (NCA) means an anion either that does not coordinate to the catalyst metal cation or that does coordinate to the metal cation, but only weakly. The term NCA is also defined to include multicomponent NCA-containing activators, such as N,N-dioctadecylanilinium tetrakis(perfluoronaphthyl)borate, which contain an acidic cationic group and the non-coordinating anion. The term NCA is also defined to include neutral Lewis acids, such as tris(pentafluoronaphthyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the non-coordinating anion. Suitable metals can include aluminum, gold, and platinum. Suitable metalloids can include boron, aluminum, phosphorus, and silicon. The term non-coordinating anion activator includes neutral activators, ionic activators, and Lewis acid activators.

"Compatible" non-coordinating anions can be those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with the present disclosure are those that are compatible, stabilize the transition metal cation in the sense of balancing its ionic charge at +1, and yet retain sufficient lability to permit displacement during polymerization.

Activators

The present disclosure provides activators, such as ammonium or phosphonium metallate or metalloid activator compounds, comprising ammonium or phosphonium groups with long-chain aliphatic hydrocarbyl groups combined with metallate or metalloid anions, such as borates or aluminates. When an activator of the present disclosure is used with a catalyst compound (such as a group 4 metallocene compound) in an olefin polymerization, a polymer can be formed having a molecular weight and melt temperature and activities comparable to those obtained with comparative activators having different cation structures and more prone toward solubility in aromatic solvents. In addition, it has been discovered that activators of the present disclosure are soluble in aliphatic solvent.

In some aspects of the invention, the activators described herein have a solubility of at least 10 mM (or at least 20 mM, or at least 50 mM) at 25° C. in methylcyclohexane.

In some aspects of the invention, the activators described herein have a solubility of about 10 mM to about 100 mM, or about 20 mM to about 80 mM, or about 50 mM to about 75 mM at 25° C. in methylcyclohexane.

In some aspects of the invention, the activators described herein have a solubility of at least 10 mM (or at least 20 mM, or at least 50 mM) at 25° C. in isohexane.

In some aspects of the invention, the activators described herein have a solubility of about 10 mM to about 100 mM, or about 20 mM to about 80 mM, or about 50 mM to about 75 mM at 25° C. in isohexane.

In some aspects of the invention, the activators described herein have a solubility of at least 10 mM (or at least 20 mM, or at least 50 mM) at 25° C. in methylcyclohexane and a solubility of at least 10 mM (or at least 20 mM, or at least 20 mM, or at least 50 mM) at 25° C. in isohexane.

The present disclosure relates to catalyst systems comprising a transition metal compound and an activator compound as described herein, to the use of such activator compounds for activating a transition metal compound in a catalyst system for polymerizing olefins, and to processes for polymerizing olefins, the processes comprising contacting under polymerization conditions one or more olefins with a catalyst system comprising a transition metal compound and such activator compounds, where aromatic solvents, such as toluene, are absent (e.g., present at zero mol %, alternately present at less than 1 mol %, preferably the catalyst system, the polymerization reaction and/or the polymer produced are free of "detectable aromatic hydrocarbon solvent," such as toluene. For purposes of the present disclosure, "detectable aromatic hydrocarbon solvent" means 0.1 mg/$m^2$ or more as determined by gas phase chromatography. For purposes of the present disclosure, "detectable toluene" means 0.1 mg/$m^2$ or more as determined by gas chromatography.

The polyolefins produced herein preferably contain 0 ppm (alternately less than 1 ppm) of aromatic hydrocarbon. Preferably, the polyolefins produced herein contain 0 ppm (alternately less than 1 ppm) of toluene.

The catalyst systems used herein preferably contain 0 ppm (alternately less than 1 ppm) of aromatic hydrocarbon. Preferably, the catalyst systems used herein contain 0 ppm (alternately less than 1 ppm) of toluene.

This invention further relates to activator compounds represented by Formula (I):

$$[Ar(EHR^1R^2)(OR^3)]_d^+[M^{k+}Q_n]^{d-} \qquad (I)$$

wherein: Ar is an aryl group; E is nitrogen or phosphorous; $R^1$ is a $C_1$-$C_{30}$, optionally substituted, linear alkyl group; $R^2$ is a $C_1$-$C_{30}$, optionally substituted, linear alkyl group; $R^3$ is a $C_{10}$-$C_{30}$, optionally substituted, linear alkyl group; M is an element selected from group 13 of the Periodic Table of the Elements; d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

In some aspects, Ar is a phenyl group. Further, in some aspects, $R^1$, $R^2$, and $R^3$ together comprise 20 or more carbon atoms.

In some aspects, $R^1$ is a $C_1$ to $C_{10}$ linear alkyl group. In particular, in some aspects, $R^1$ is methyl, ethyl, propyl, butyl, pentyl, hexyl, heptyl, octyl, nonyl, or decyl. In some aspects, $R^2$ is a $C_1$-$C_{20}$, optionally substituted, linear alkyl group. In some aspects, $R^3$ is a $C_{10}$-$C_{20}$, optionally substituted, linear alkyl group.

In some aspects, $R^1$ is methyl, $R^2$ is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl, and $R^3$ is n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

In some aspects of any activator formula herein, each $R^1$, $R^2$ and/or $R^3$ may be independently optionally substituted with at least one of halide, $C_1$-$C_{50}$ alkyl, $C_5$-$C_{50}$ aryl, $C_6$-$C_{35}$ arylalkyl, or $C_6$-$C_{35}$ alkylaryl, provided that substituted $R^2$ and $R^3$ groups are not branched alkyl groups (as defined above).

In some aspects, Q is an optionally substituted aryl group. Preferably, Q may be a halogen substituted aryl group. Preferably, each Q is a fluorinated hydrocarbyl group having 1 to 30 carbon atoms, more preferably each Q is a fluorinated aryl (such as phenyl or naphthyl) group, and most preferably each Q is a perfluorinated aryl (such as phenyl or naphthyl) group. In particular, at least one, preferably all, Q may be a perfluoroaryl group. More particularly, at least one, preferably all, Q may be a perfluorophenyl group or a perfluoronaphthyl group.

In at least one aspect of the invention, the activator is represented by Formula (II):

$$[Cat]^+[MQ_4]^- \qquad (II)$$

wherein M is a group 13 atom, preferably B or Al; Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

In some aspects, the $[Cat]^+$ is selected from the group consisting of:

(C1)

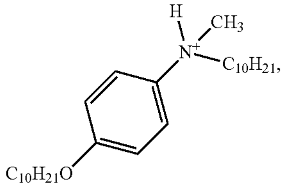

(C2)

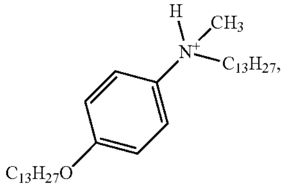

(C3)

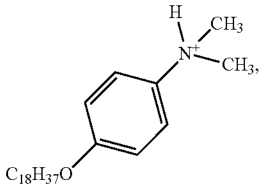

and (C4)

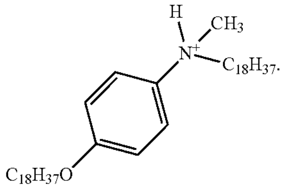

In some aspects, Q is an optionally substituted aryl group. Preferably, Q may be a halogen substituted aryl group. Preferably, each Q is a fluorinated hydrocarbyl group having 1 to 30 carbon atoms, more preferably each Q is a fluorinated aryl (such as phenyl or naphthyl) group, and most preferably each Q is a perfluorinated aryl (such as phenyl or naphthyl) group. In particular, Q may be a perfluoroaryl group. More particularly, Q may be a perfluorophenyl group or a perfluoronaphthyl group.

In at least one aspect, an activator is an ionic ammonium or phosphonium borate represented by Formula (III):

$$[R^{11}R^{12}R^{13}EH]^+[BR^{14}R^{15}R^{16}R^{17}]^- \quad \text{(II)}$$

wherein E is nitrogen or phosphorous; each of $R^{11}$, $R^{12}$, and $R^{13}$ is independently a $C_1$-$C_{30}$ linear alkyl group or an aryl group, wherein the aryl is substituted with at least one $C_{10}$-$C_{30}$ alkoxy group, wherein $R^{11}$, $R^{12}$, and $R^{13}$ together comprise 26 or more carbon atoms; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

This invention also relates to activator compounds represented by Formula (III):

$$[R^{11}R^{12}R^{13}EH]^+[BR^{14}R^{15}R^{16}R^{17}]^- \quad \text{(III)}$$

wherein: E is nitrogen or phosphorous; each of $R^{11}$ and $R^{12}$ is independently $C_1$-$C_{30}$ linear alkyl, $R^{13}$ is an aryl group substituted with a $C_{10}$-$C_{30}$ alkoxy group; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

This invention also relates to activator compounds represented by Formula (III):

$$[R^{11}R^{12}R^{13}EH]^+[BR^{14}R^{15}R^{16}R^{17}]^- \quad \text{(III)}$$

wherein: E is nitrogen or phosphorous; each of $R^{11}$ and $R^{12}$ is independently $C_1$-$C_{30}$ linear alkyl, $R^{13}$ is an aryl group substituted with a $C_{10}$-$C_{30}$ alkoxy group; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms, and wherein $R^{11}$, $R^{12}$, and $R^{13}$ together comprise 30 or more (or 40 or more) carbon atoms.

In any aspect described herein, each of $R^{14}$, $R^{15}$, $R^{16}$, and $R^{17}$ is independently each a fluorinated hydrocarbyl group having 1 to 30 carbon atoms, more preferably each of $R^{14}$, $R^{15}$, $R^{16}$, and $R^{17}$ is independently a fluorinated aryl (such as phenyl, biphenyl, $[(C_6H_3(C_6H_5)_2)_4B]$, or naphthyl) group, and most preferably each of $R^{14}$, $R^{15}$, $R^{16}$, and $R^{17}$ is independently a perfluorinated aryl (such as bi-phenyl, $[(C_6H_3(C_6H_5)_2)_4B]$, or naphthyl) group.

In any aspect described herein, preferably each of $R^{14}$, $R^{15}$, $R^{16}$, and $R^{17}$ is independently a naphthyl comprising one fluorine atom, two fluorine atoms, three fluorine atoms, four fluorine atoms, five fluorine atoms, six fluorine atoms, or seven fluorine atoms, preferably seven fluorine atoms.

In any aspect described herein, preferably each of $R^{14}$, $R^{15}$, $R^{16}$, and $R^{17}$ is independently a phenyl comprising one fluorine atom, two fluorine atoms, three fluorine atoms, four fluorine atoms, five fluorine atoms, preferably five fluorine atoms.

In at least one aspect, $R^{14}$ is independently naphthyl comprising one fluorine atom, two fluorine atoms, three fluorine atoms, four fluorine atoms, five fluorine atoms, six fluorine atoms, or seven fluorine atoms.

In at least one aspect, $R^{14}$ is independently naphthyl comprising one fluorine atom, two fluorine atoms, three fluorine atoms, four fluorine atoms, or five fluorine atoms.

In at least one aspect, $R^{15}$ is independently naphthyl comprising one fluorine atom, two fluorine atoms, three fluorine atoms, four fluorine atoms, five fluorine atoms, six fluorine atoms, or seven fluorine atoms.

In at least one aspect, $R^{15}$ is independently naphthyl comprising one fluorine atom, two fluorine atoms, three fluorine atoms, four fluorine atoms, or five fluorine atoms.

In at least one aspect, $R^{16}$ is independently naphthyl comprising one fluorine atom, two fluorine atoms, three fluorine atoms, four fluorine atoms, five fluorine atoms, six fluorine atoms, or seven fluorine atoms.

In at least one aspect, $R^{16}$ is independently naphthyl comprising one fluorine atom, two fluorine atoms, three fluorine atoms, four fluorine atoms, or five fluorine atoms.

In at least one aspect, $R^{17}$ is independently naphthyl comprising one fluorine atom, two fluorine atoms, three fluorine atoms, four fluorine atoms, five fluorine atoms, six fluorine atoms, or seven fluorine atoms.

In at least one aspect, $R^{17}$ is independently naphthyl comprising one fluorine atom, two fluorine atoms, three fluorine atoms, four fluorine atoms, or five fluorine atoms.

The terms "cocatalyst" and "activator" are used herein interchangeably and are defined to be any compound which can activate any one of the catalyst compounds of the present disclosure by converting the neutral catalyst compound to a catalytically active catalyst compound cation.

Catalyst systems of the present disclosure may be formed by combining the catalysts with activators in any suitable manner, including by supporting them for use in slurry or gas phase polymerization. The catalyst systems may also be added to or generated in solution polymerization or bulk polymerization (in the monomer, i.e., little or no solvent).

Both the cation part of Formulas (I), (II) and (III) as well as the anion part thereof, which is an NCA, will be further illustrated below. Any combinations of cations and NCAs disclosed herein are suitable to be used in the processes of the present disclosure and are thus incorporated herein.

Activators—the Cations

The cation component of the activators described herein (such as those of Formulas (I), (II) and (III) above), is a protonated Lewis base that can be capable of protonating a moiety, such as an alkyl or aryl, from the transition metal compound. Thus, upon release of a neutral leaving group (e.g., an alkane resulting from the combination of a proton donated from the cationic component of the activator and an alkyl substituent of the transition metal compound) transition metal cation results, which is the catalytically active species.

In at least one aspect of Formula (I), E is nitrogen or phosphorous, Ar is an ortho, meta, or para substituted phenyl, each of $R^1$ and $R^2$ is independently a $C_1$-$C_{30}$, optionally substituted, linear alkyl group, and $R^3$ is a $C_{10}$-$C_{30}$, optionally substituted, linear alkyl group, wherein each of $R^1$, $R^2$, and $R^3$ is optionally substituted by halogen, —$NR'_2$, —OR' or —$SiR'_3$ (where each R' is independently hydrogen or $C_1$-$C_{20}$ hydrocarbyl). Preferably, Ar is a para-substituted phenyl group. In an aspect, $R^1$, $R^2$, and $R^3$ together comprise 20 or more carbon atoms, such as 26 or more carbon atoms, such as 27 or more carbon atoms, such as 43 or more carbon atoms. In at least one aspect, $R^1$, $R^2$, and $R^3$ are independently substituted or unsubstituted $C_1$-$C_{22}$ linear alkyl, or substituted or unsubstituted phenyl. In at least one embodiment, each of $R^1$ and $R^2$ is independently selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. In at least one aspect, $R^3$ is selected from n-decyl, n-undecyl, n-dodecyl, n-tridecyl, n-tetradecyl, n-pentadecyl, n-hexadecyl, n-heptadecyl, n-octadecyl, n-nonadecyl, and n-icosyl.

In another aspect, $R^1$ is methyl, $R^2$ is $C_1$ to $C_{30}$ alkyl, $R^3$ is $C_{10}$ to $C_{30}$ linear alkyl.

In another aspect, $R^1$ is methyl, $R^2$ is methyl, n-decyl, n-tridecyl, or n-icosyl, and $R^3$ is $C_{10}$ to $C_{30}$ linear alkyl.

In another aspect, $R^1$ is methyl, $R^2$ is methyl, n-decyl, n-tridecyl, or n-icosyl, and $R^3$ is n-decyl, n-tridecyl, or n-icosyl.

In at least one aspect of Formula (III), E is nitrogen or phosphorous, $R^{11}$ is a methyl group; $R^{12}$ is $C_1$-$C_{30}$ alkyl, and $R^3$ is an aryl group substituted with at least one $C_{10}$-$C_{30}$ linear alkoxy group, wherein $R^{11}$, $R^{12}$, and $R^{13}$ together comprise 26 or more carbon atoms, such as 30 or more carbon atoms, such as 40 or more carbon atoms. In at least one aspect, each of $R^1$ and $R^2$ is independently selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. In at least one aspect, $R^3$ is selected from phenyl alkoxydecyl, phenyl alkoxyundecyl, phenyl alkoxydodecyl, phenyl alkoxytridecyl, phenyl alkoxytetradecyl, phenyl alkoxypentadecyl, phenyl alkoxyhexadecyl, phenyl alkoxyheptadecyl, phenyl alkoxyoctadecyl, phenyl alkoxynonadecyl, and phenyl alkoxyicosyl.

Preferably, the compound represented by Formulas (I), (II), and (III) comprises a cation selected from the group consisting of:

(C1)

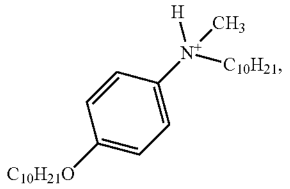

(C2)

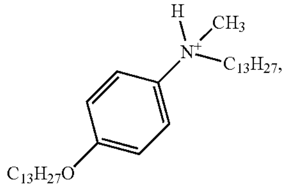

(C3)

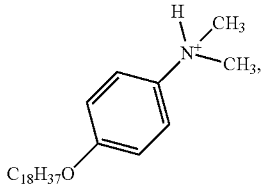

and (C4)

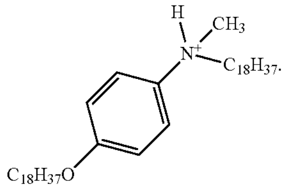

Activators—the Anion

The anion component of the activators described herein includes those represented by the formula $[M^{k+}Q_n]^-$ wherein k is 1, 2, or 3; n is 1, 2, 3, 4, 5, or 6 (preferably 1, 2, 3, or 4), (preferably k is 3; n is 4, 5, or 6, preferably when M is B, n is 4); M is an element selected from group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms. Preferably, each Q is a fluorinated hydrocarbyl group, optionally having 1 to 20 carbon atoms, more preferably each Q is a fluorinated aryl group, and most preferably each Q is a perfluorinated aryl group. In an aspect, Q is a substituted phenyl, such as a perfluorophenyl. In another aspect, Q is a substituted naphthyl, such as a perfluoronaphthyl.

In at least one aspect, the anion component of the activators includes those represented by the formula $[MQ_4]^-$ wherein Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical. Preferably, each Q is a fluorinated hydrocarbyl group, optionally having 1 to 20 carbon atoms, more preferably each Q is a fluorinated aryl group, and most preferably each Q is a perfluorinated aryl group. In an aspect, Q is a substituted phenyl, such as a perfluorophenyl. In another aspect, Q is a substituted naphthyl, such as a perfluoronaphthyl.

In another aspect, for the borate moiety ($[BR^{14}R^{15}R^{16}R^{17}]$) of the activator represented by Formula (III), each of $R^{14}$, $R^{15}$, $R^{16}$, and $R^{17}$ is independently aryl (such as phenyl or naphthyl), wherein at least one of $R^{14}$, $R^{15}$, $R^{16}$, and $R^{17}$ is substituted with from one to seven fluorine atoms. In at least one embodiment, each of $R^{14}$, $R^{15}$, $R^{16}$, and $R^{17}$ is naphthyl, wherein at least one of $R^{14}$, $R^{15}$, $R^{16}$, and $R^{17}$ is substituted with from one to seven fluorine atoms.

In at least one aspect, each of $R^{14}$, $R^{15}$, $R^{16}$, and $R^{17}$ is independently naphthyl comprising one fluorine atom, two fluorine atoms, three fluorine atoms, four fluorine atoms, five fluorine atoms, six fluorine atoms, or seven fluorine atoms.

In at least one aspect, each of $R^{14}$, $R^{15}$, $R^{16}$, and $R^{17}$ is independently phenyl comprising one fluorine atom, two fluorine atoms, three fluorine atoms, four fluorine atoms, or five fluorine atoms.

In one aspect, the borate activator comprises tetrakis (pentafluorophenyl)borate.

In another aspect, the borate activator comprises tetrakis (heptafluoronaphthyalen-2-yl)borate.

Preferred anions for use in the non-coordinating anion activators described herein include those represented by Formula (VIII) below:

(VIII)

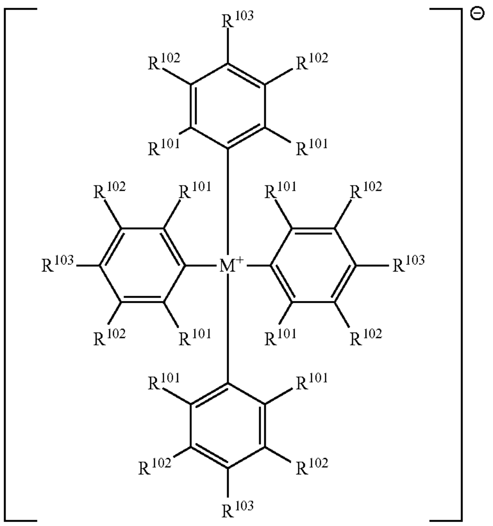

wherein:

M* is a group 13 atom, preferably B or Al, preferably B;

each $R^{101}$ is, independently, a halide, preferably a fluoride;

each $R^{102}$ is, independently, a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{102}$ is a fluoride or a perfluorinated phenyl group;

each $R^{103}$ is a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{103}$ is a fluoride or a $C_6$ perfluorinated aromatic hydrocarbyl group;

wherein $R^{102}$ and $R^{103}$ can form one or more saturated or unsaturated, substituted or unsubstituted rings, preferably $R^{102}$ and $R^{103}$ form a perfluorinated phenyl ring. Preferably the anion has a molecular weight of greater than 700 g/mol, and, preferably, at least three of the substituents on the M* atom each have a molecular volume of greater than 180 cubic A.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in Girolami, G. S. (1994) "A Simple "Back of the Envelope" Method for Estimating the Densities and Molecular Volumes of Liquids and Solids," *Journal of Chemical Education*, v.71(11), pp. 962-964. Molecular volume (MV), in units of cubic A, is calculated using the formula: $MV=8.3V_S$, where $V_S$ is the scaled volume. $V_S$ is the sum of the relative volumes of the constituent atoms, and is calculated from the molecular formula of the substituent using Table 1 below of relative volumes. For fused rings, the $V_S$ is decreased by 7.5% per fused ring. The Calculated Total MV of the anion is the sum of the MV per substituent, for example, the MV of perfluorophenyl is 183 Å$^3$, and the Calculated Total MV for tetrakis(perfluorophenyl)borate is four times 183 Å$^3$, or 732 Å$^3$.

TABLE 1

| Element | Relative Volume |
|---|---|
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

Exemplary anions useful herein and their respective scaled volumes and molecular volumes are shown in Table 2 below. The dashed bonds indicate bonding to boron.

TABLE 2

| Ion | Structure of Boron Substituents | Molecular Formula of Each Substituent | $V_S$ | MV Per subst. (Å$^3$) | Calculated Total MV (Å$^3$) |
|---|---|---|---|---|---|
| tetrakis (perfluorophenyl) borate | 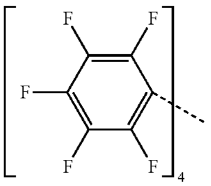 | $C_6F_5$ | 22 | 183 | 732 |

TABLE 2-continued

| Ion | Structure of Boron Substituents | Molecular Formula of Each Substituent | $V_S$ | MV Per subst. (Å$^3$) | Calculated Total MV (Å$^3$) |
|---|---|---|---|---|---|
| tris(perfluorophenyl)-(perfluoronaphthyl) borate | 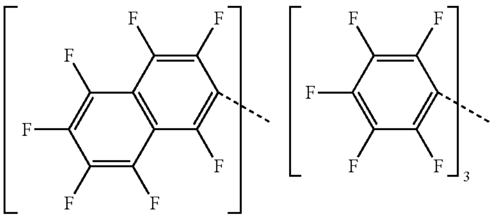 | $C_6F_5$<br>$C_{10}F_7$ | 22<br>34 | 183<br>261 | 810 |
| (perfluorophenyl)tris-(perfluoronaphthyl) borate | 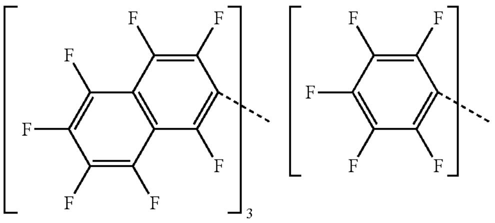 | $C_6F_5$<br>$C_{10}F_7$ | 22<br>34 | 183<br>261 | 966 |
| tetrakis (perfluoronaphthyl) borate | 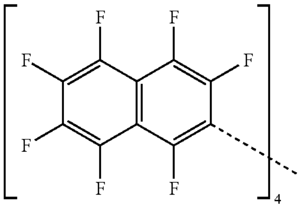 | $C_{10}F_7$ | 34 | 261 | 1044 |
| tetrakis (perfluorobiphenyl) borate | 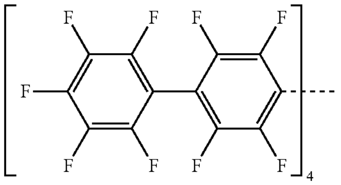 | $C_{12}F_9$ | 42 | 349 | 1396 |
| $[(C_6CAT\text{-}2(C_6F_5)_2)_4B]$ | 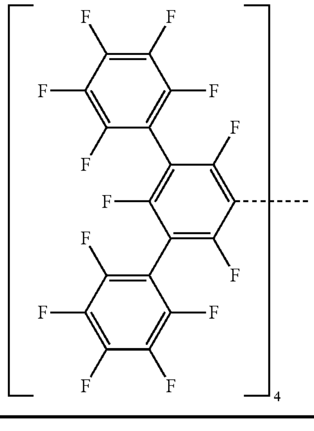 | $C_{18}F_{13}$ | 62 | 515 | 2060 |

The activators may be added to a polymerization in the form of an ion pair using, for example, $[M2HTH]^+[NCA]^-$ in which the di(hydrogenated tallow)methylamine ("M2HTH") cation reacts with a basic leaving group on the transition metal complex to form a transition metal complex cation and $[NCA]^-$. Alternatively, the transition metal complex may be reacted with a neutral NCA precursor, such as $B(C_{10}F_7)_3$, which abstracts an anionic group from the complex to form an activated species. Useful activators include di(hydrogenated tallow)methylamine(perfluoronaphthyl) borate (i.e., $[M2HTH]B(C_{10}F_7)_4$) and di(octadecyl)tolylamine (perfluoronaphthyl)borate (i.e., $[DOdTH]B(C_{10}C_7)_4$).

In at least one aspect, the activators obtained in their salt form used for a borate activator compound are: Lithium tetrakis(pentafluorophenyl)borate etherate (Li—Al), N,N-dimethylanilinium tetrakis(pentafluorophenyl)borate (DMAH-A1), Sodium tetrakis(heptafluoronaphthalen-2-yl)

borate (Na-A2) and N,N-dimethylanilinium tetrakis(heptafluoronaphthalen-2-yl)borate (DMAH-A2).

In at least one aspect, an activator of the present disclosure, when combined with a group 4 metallocene catalyst compound to form an active olefin polymerization catalyst, produces a higher molecular weight polymer (e.g., Mw) than comparative activators that use other borate anions.

In at least one aspect, an activator of the present disclosure where $R^1$ is methyl, when combined with a group 4 metallocene to form an active olefin polymerization catalyst, produces a higher molecular weight polymer (e.g., Mw) than comparative activators that use other borate anions.

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of the present disclosure that the catalyst compounds can be combined with combinations of alumoxanes and the activators described herein.

Synthesis

In one aspect, the general synthesis of the activators can be performed using a three-step process. In the first step, an alkylated amine or phosphine containing an ether group is prepared from an aminophenol or phosphinophenol and a bromoalkane in the presence of sodium hydride in a solvent (e.g., tetrahydrofuran). The resulting alkylated amine or phosphine is then dissolved in a solvent (e.g., hexane, cyclohexane, methylcyclohexane, ether, dichloromethane, toluene) and an excess (e.g., 1.2 molar equivalents) of hydrogen chloride was added to form an ammonium chloride salt. This salt is typically isolated by filtration from the reaction medium and dried under reduced pressure. The isolated ammonium chloride is then heated to reflux with one molar equivalent of an alkali metal metallate or metalloid (such as borate or aluminate) in a solvent (e.g., cyclohexane, dichloromethane, methylcyclohexane) to form the desired ammonium borate or aluminate along with byproduct alkali metal chloride, the latter which typically is removed by filtration.

In at least one aspect, the general synthesis of the ammonium borate activators can be performed using a three-step process. In the first step, an alkylated amine containing an ether group is prepared from an aminophenol and a bromoalkane in the presence of sodium hydride in a solvent (e.g., tetrahydrofuran). In the second step, the resulting alkylated amine is dissolved in a solvent (e.g., hexane, cyclohexane, methylcyclohexane, ether, dichloromethane, toluene) and an excess (e.g., 1.2 molar equivalents) of hydrogen chloride is added to form an ammonium chloride salt. This salt is typically isolated by filtration from the reaction medium and dried under reduced pressure. The isolated ammonium chloride is then heated to reflux with about one molar equivalent of an alkali metal borate in a solvent (e.g. cyclohexane, dichloromethane, methylcyclohexane) to form the ammonium borate along with byproduct alkali metal chloride, the latter of which can typically be removed by filtration.

In at least one embodiment, an activator of the present disclosure is soluble in an aliphatic solvent at a concentration of about 10 mM or greater, such as about 20 mM or greater, such as about 30 mM or greater, such as about 50 mM or greater, such as about 75 mM or greater, such as about 100 mM or greater, such as about 200 mM or greater, such as about 300 mM or greater. In at least one embodiment, an activator of the present disclosure dissolves in isohexane or methylcyclohexane at 25° C. to form a homogeneous solution of at least 10 mM concentration.

In at least one embodiment, the solubility of the borate or aluminate activators of the present disclosure in aliphatic hydrocarbon solvents increases with the number of aliphatic carbons in the cation group (i.e., the ammonium or the phosphonium). In at least one embodiment, a solubility of at least 10 mM is achieved with an activator having an ammonium or phosphonium group of about 20 aliphatic carbon atoms or more, such as about 25 aliphatic carbons atoms or more, such as about 30 carbon atoms or more, such as about 35 carbon atoms or more.

In at least one embodiment, the solubility of the ammonium borate activators of the present disclosure in aliphatic hydrocarbon solvents increases with the number of aliphatic carbons in the ammonium group. In at least one embodiment, a solubility of at least 10 mM is achieved with an activator having an ammonium group of about 20 aliphatic carbon atoms or more, such as about 25 aliphatic carbons atoms or more, such as about 30 carbon atoms or more, such as about 35 carbon atoms or more.

Useful aliphatic hydrocarbon solvents can be isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In at least one embodiment, aromatics are present in the solvent at less than 1 wt %, such as less than 0.5 wt %, such as at 0 wt % based upon the weight of the solvents. The activators of the present disclosure can be dissolved in one or more additional solvents. Additional solvents include ethereal, halogenated and N,N-dimethylformamide solvents.

In at least one embodiment, the aliphatic solvent is isohexane and/or methylcyclohexane.

Optional Scavengers or Co-Activators

In addition to these activator compounds, scavengers or co-activators may be used. Aluminum alkyl or organoaluminum or organozinc compounds which may be utilized as scavengers or co-activators include, for example, trimethylaluminum, triethylaluminum, triisobutylaluminum, tri-n-hexylaluminum, tri-n-octylaluminum, and diethyl zinc.

In at least one embodiment, little or no scavenger is used in the process to produce the ethylene polymer. Scavenger (such as trialkyl aluminum) can be present at zero mol %, alternately the scavenger is present at a molar ratio of scavenger metal to transition metal of less than 100:1, such as less than 50:1, such as less than 15:1, such as less than 10:1.

Transition Metal Catalyst Compounds

Any transition metal compound capable of catalyzing a reaction, such as a polymerization reaction, upon activation with an activator as described above is suitable for use in polymerization processes of the present disclosure. Transition metal compounds known as metallocenes are exemplary catalyst compounds according to the present disclosure.

In at least one embodiment, the present disclosure provides a catalyst system comprising a catalyst compound having a metal atom. The catalyst compound can be a metallocene catalyst compound. The metal can be a group 3 through group 12 metal atom, such as group 3 through group 10 metal atoms, or lanthanide group atoms. The catalyst compound having a group 3 through group 12 metal atom can be monodentate or multidentate, such as bidentate, tridentate, or tetradentate, where a heteroatom of the catalyst, such as phosphorous, oxygen, nitrogen, or sulfur is chelated to the metal atom of the catalyst. Non-limiting examples include bis(phenolate)s. In at least one embodiment, the group 3 through group 12 metal atom is selected from group 5, group 6, group 8, or group 10 metal atoms. In at least one embodiment, a group 3 through group 10 metal atom is selected from Cr, Sc, Ti, Zr, Hf, V, Nb, Ta, Mn, Re, Fe, Ru, Os, Co, Rh, Ir, and Ni. In at least one embodiment, a metal atom is selected from groups 4, 5, and 6 metal atoms. In at least one embodiment, a metal atom is a group 4 metal atom selected from Ti, Zr, or Hf. The oxidation state of the metal atom can range from 0 to +7, for example +1, +2, +3, +4, or +5, for example +2, +3, or +4.

Metallocene Catalyst Compounds

A "metallocene" catalyst compound is preferably a transition metal catalyst compound having one, two or three, typically one or two, substituted or unsubstituted cyclopentadienyl ligands (such as substituted or unsubstituted Cp, Ind or Flu) bound to the transition metal. Metallocene catalyst compounds as used herein include metallocenes comprising group 3 to group 12 metal complexes, such as, group 4 to group 6 metal complexes, for example, group 4 metal complexes. The metallocene catalyst compound of catalyst systems of the present disclosure may be unbridged metallocene catalyst compounds represented by the formula: $Cp^ACp^BM'X'_n$, wherein each $Cp^A$ and $Cp^B$ is independently selected from cyclopentadienyl ligands (for example, Cp, Ind, or Flu) and ligands isolobal to cyclopentadienyl, one or both $Cp^A$ and $Cp^B$ may contain heteroatoms, and one or both $Cp^A$ and $Cp^B$ may be substituted by one or more R" groups; M' is selected from groups 3 through 12 atoms and lanthanide group atoms; X' is an anionic leaving group; n is 0 or an integer from 1 to 4; each R" is independently selected from alkyl, substituted alkyl, heteroalkyl, alkenyl, substituted alkenyl, heteroalkenyl, alkynyl, substituted alkynyl, heteroalkynyl, alkoxy, aryloxy, alkylthio, arylthio, aryl, substituted aryl, heteroaryl, aralkyl, aralkylene, alkaryl, alkarylene, haloalkyl, haloalkenyl, haloalkynyl, heteroalkyl, heterocycle, heteroaryl, a heteroatom-containing group, hydrocarbyl, substituted hydrocarbyl, heterohydrocarbyl, silyl, boryl, phosphino, phosphine, amino, amine, ether, and thioether.

In at least one embodiment, each $Cp^A$ and $Cp^B$ is independently selected from cyclopentadienyl, indenyl, fluorenyl, indacenyl, tetrahydroindenyl, cyclopentaphenanthreneyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated and substituted versions thereof. Each $Cp^A$ and $Cp^B$ may independently be indacenyl or tetrahydroindenyl.

The metallocene catalyst compound may be a bridged metallocene catalyst compound represented by the formula: $Cp^A(T)Cp^BM'X'_n$, wherein each $Cp^A$ and $Cp^B$ is independently selected from cyclopentadienyl ligands (for example, Cp, Ind, or Flu) and ligands isolobal to cyclopentadienyl, where one or both $Cp^A$ and $Cp^B$ may contain heteroatoms, and one or both $Cp^A$ and $Cp^B$ may be substituted by one or more R" groups; M' is selected from groups 3 through 12 atoms and lanthanide group atoms, preferably group 4; X' is an anionic leaving group; n is 0 or an integer from 1 to 4; (T) is a bridging group selected from divalent alkyl, divalent substituted alkyl, divalent heteroalkyl, divalent alkenyl, divalent substituted alkenyl, divalent heteroalkenyl, divalent alkynyl, divalent substituted alkynyl, divalent heteroalkynyl, divalent alkoxy, divalent aryloxy, divalent alkylthio, divalent arylthio, divalent aryl, divalent substituted aryl, divalent heteroaryl, divalent aralkyl, divalent aralkylene, divalent alkaryl, divalent alkarylene, divalent haloalkyl, divalent haloalkenyl, divalent haloalkynyl, divalent heteroalkyl, divalent heterocycle, divalent heteroaryl, a divalent heteroatom-containing group, divalent hydrocarbyl, divalent substituted hydrocarbyl, divalent heterohydrocarbyl, divalent silyl, divalent boryl, divalent phosphino, divalent phosphine, divalent amino, divalent amine, divalent ether, divalent thioether. R" is selected from alkyl, substituted alkyl, heteroalkyl, alkenyl, substituted alkenyl, heteroalkenyl, alkynyl, substituted alkynyl, heteroalkynyl, alkoxy, aryloxy, alkylthio, arylthio, aryl, substituted aryl, heteroaryl, aralkyl, aralkylene, alkaryl, alkarylene, haloalkyl, haloalkenyl, haloalkynyl, heteroalkyl, heterocycle, heteroaryl, a heteroatom-containing group, hydrocarbyl, substituted hydrocarbyl, heterohydrocarbyl, silyl, boryl, phosphino, phosphine, amino, amine, germanium, ether, and thioether.

In at least one embodiment, each of $Cp^A$ and $Cp^B$ is independently selected from cyclopentadienyl, indenyl, fluorenyl, cyclopentaphenanthreneyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated, and substituted versions thereof, preferably cyclopentadienyl, n-propylcyclopentadienyl, indenyl, pentamethylcyclopentadienyl, tetramethylcyclopentadienyl, and n-butylcyclopentadienyl. Each $Cp^A$ and $Cp^B$ may independently be indacenyl or tetrahydroindenyl.

(T) is a bridging group containing at least one Group 13, 14, 15, or 16 element, in particular boron or a Group 14, 15 or 16 element, preferably (T) is O, S, NR', or $SiR'_2$, where each R' is independently hydrogen or $C_1$-$C_{20}$ hydrocarbyl.

In another embodiment, the metallocene catalyst compound is represented by the formula:

$$T_yCp_mMG_nX_q$$

where Cp is independently a substituted or unsubstituted cyclopentadienyl ligand (for example, substituted or unsubstituted Cp, Ind, or Flu) or substituted or unsubstituted ligand isolobal to cyclopentadienyl; M is a group 4 transition metal; G is a heteroatom group represented by the formula JR*z where J is N, P, O or S, and R* is a linear, branched, or cyclic $C_1$-$C_{20}$ hydrocarbyl; z is 1 or 2; T is a bridging group; y is 0 or 1; X is a leaving group; m=1, n=1, 2 or 3, q=0, 1, 2 or 3, and the sum of m+n+q is equal to the coordination number of the transition metal.

In at least one embodiment, J is N, and R* is methyl, ethyl, propyl, butyl, pentyl, hexyl, heptyl, octyl, nonyl, cyclooctyl, cyclododecyl, decyl, undecyl, dodecyl, adamantyl or an isomer thereof.

In at least one embodiment, the catalyst compound is represented by Formula (IV):

(IV)

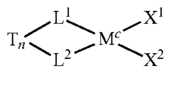

wherein in Formula (IV): $M^c$ is the metal center, and is a group 4 metal, such as titanium, zirconium or hafnium; n is 0 or 1; T is an optional bridging group selected from S, O, PR', NR', $SiR"_2$, $CH_2$, CHR", or $CR"_2$, wherein R' is a $C_1$-$C_{30}$, optionally substituted, hydrocarbyl group and R" is hydrogen or a $C_1$-$C_{30}$, optionally substituted, hydrocarbyl group; $L^1$ and $L^2$ are independently cyclopentadienyl, substituted cyclopentadienyl, indenyl, substituted indenyl, tetrahydroindenyl, substituted tetrahydroindenyl, fluorenyl, or substituted fluorenyl groups; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Preferably, T in any formula herein is present and is a bridging group containing at least one group 13, 14, 15, or 16 element, in particular a group 14 element. Examples of suitable bridging groups include P(=S)R', P(=Se)R', P(=O)R', $R'_2C$, $R'_2Si$, $R'_2Ge$, $R'_2CCR'_2$, $R'_2CCR'_2CR'_2$, $R'_2CCR'_2CR'_2CR'_2$, R'C=CR', R'C=CR'CR'$_2$, $R'_2CCR'$=CR'CR'$_2$, R'C=CR'CR'=CR', R'C=CR'CR'$_2$CR'$_2$, $R'_2CSiR'_2$, $R'_2SiSiR'_2$, $R'_2SiOSiR'_2$, $R'_2CSiR'_2CR'_2$, $R'_2SiCR'_2SiR'_2$, R'C=CR'SiR'$_2$, $R'_2CGeR'_2$, $R'_2GeGeR'_2$, $R'_2CGeR'_2CR'_2$, $R'_2GeCR'_2GeR'_2$, $R'_2SiGeR'_2$, R'C=CR'GeR'$_2$, R'B, $R'_2C$—BR', $R'_2C$—BR'—CR'$_2$, $R'_2C$—O—CR'$_2$, $R'_2CR'_2C$—O—CR'$_2$CR'$_2$, $R'_2C$—O—CR'$_2$CR'$_2$, $R'_2C$—O—CR'=CR', $R'_2C$—S—CR'$_2$, $R'_2CR'_2C$—S—CR'$_2$CR'$_2$, $R'_2C$—S—CR'$_2$CR'$_2$, $R'_2C$—S—CR'=CR', $R'_2C$—Se—CR'$_2$, $R'_2CR'_2C$—Se—CR'$_2$CR'$_2$, $R'_2C$—Se—CR'$_2$CR'$_2$, $R'_2C$—Se—CR'=CR', $R'_2C$—N=CR', $R'_2C$—NR'—CR'$_2$, $R'_2C$—NR'—CR'$_2$CR'$_2$, $R'_2C$—NR'—CR'=CR', $R'_2CR'_2C$—NR'—CR'$_2$CR'$_2$, $R'_2C$—P=CR', $R'_2C$—PR'—CR'$_2$, O, S, Se, Te, NR', PR', AsR', SbR', O—O, S—S, R'N—NR', R'P—PR', O—S, O—NR', O—PR', S—NR', S—PR', and R'N—PR' where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group T include $CH_2$, $CH_2CH_2$, $SiMe_2$, $SiPh_2$, SiMePh, $Si(CH_2)_3$, $Si(CH_2)_4$, O, S, NPh, PPh, NMe, PMe, NEt, NPr, NBu, PEt, PPr, $Me_2SiOSiMe_2$, and PBu.

In an aspect of the application, T is represented by the formula $R^a_2J$ or $(R^a_2J)_2$, where J is C, Si, or Ge, and each $R^a$ is, independently, hydrogen, halogen, $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl, and two $R^a$ can form a cyclic structure including aromatic, partially saturated, or saturated cyclic or fused ring system. Preferably, T is a bridging group comprising carbon or silicon, such as dialkylsilyl, preferably T is selected from $CH_2$, $CH_2CH_2$, $C(CH_3)_2$, $SiMe_2$, $SiPh_2$, SiMePh, silylcyclobutyl ($Si(CH_2)_3$), $(Ph)_2C$, $(p-(Et)_3SiPh)_2C$, $Me_2SiOSiMe_2$, and cyclopentasilylene ($Si(CH_2)_4$).

In an aspect of the application, T is an optional bridging group selected from dialkylsilyl, diarylsilyl, dialkylmethyl, diarylmethyl, ethylenyl, or hydrocarbylethylenyl wherein one, two, three or four of the hydrogen atoms in ethylenyl are substituted by hydrocarbyl.

In at least one aspect, the catalyst compound has a symmetry that is $C_2$ symmetrical.

Suitable metallocenes useful herein include, but are not limited to, the metallocenes disclosed and referenced in the US patents cited above, as well as those disclosed and referenced in U.S. Pat. Nos. 7,179,876; 7,169,864; 7,157,531; 7,129,302; 6,995,109; 6,958,306; 6,884,748; 6,689,847; US Patent publication 2007/0055028, and published PCT Applications WO 1997/022635; WO 2000/699/22; WO 2001/030860; WO 2001/030861; WO 2002/046246; WO 2002/050088; WO 2004/026921; and WO 2006/019494, all fully incorporated herein by reference. Additional catalysts suitable for use herein include those referenced in U.S. Pat. Nos. 6,309,997; 6,265,338; US Patent publication 2006/019925, and the following articles: Resconi, L. et al. (2000) "Selectivity in Propene Polymerization with Metallocene Catalysts," *Chem. Rev.*, v.100(4), pp. 1253-1346; Gibson, V. C. et al. (2003) "Advances in Non-Metallocene Olefin Polymerization Catalysis," *Chem. Rev.*, v.103(1), pp. 283-316; *Chem Eur. J.* 2006, v.12, p. 7546; Nakayama, Y et al. (2004), "Olefin Polymerization Behavior of bis(phenoxy-imine) Zr, Ti, and V complexes with $MgCl_2$-based Cocatalysts," *J. Mol. Catalysis A: Chemical*, v.213, pp. 141-150; Nakayama, Y. et al. (2005), Propylene Polymerization Behavior of Fluorinated Bis(phenoxy-imine) Ti Complexes with an $MgCl_2$—Based Compound ($MgCl_2$—Supported Ti-Based Catalysts)," *Macromol. Chem. Phys.*, v.206(18), pp. 1847-1852; and Matsui, S. et al. (2001) "A Family of Zirconium Complexes Having Two Phenoxy-Imine Chelate Ligands for Olefin Polymerization," *J. Am. Chem. Soc.*, v.123(28), pp. 6847-6856.

Exemplary metallocene compounds useful herein include:
bis(cyclopentadienyl)zirconium dichloride,
bis(n-butylcyclopentadienyl)zirconium dichloride,
bis(n-butylcyclopentadienyl)zirconium dimethyl,
bis(pentamethylcyclopentadienyl)zirconium dichloride,
bis(pentamethylcyclopentadienyl)zirconium dimethyl,
bis(pentamethylcyclopentadienyl)hafnium dichloride,
bis(pentamethylcyclopentadienyl)zirconium dimethyl,
bis(1-methyl-3-n-butylcyclopentadienyl)zirconium dichloride,
bis(1-methyl-3-n-butylcyclopentadienyl)zirconium dimethyl,
bis(1-methyl-3-n-butylcyclopentadienyl)hafnium dichloride,
bis(1-methyl-3-n-butylcyclopentadienyl)zirconium dimethyl,
bis(indenyl)zirconium dichloride, bis(indenyl)zirconium dimethyl,
bis(tetrahydro-1-indenyl)zirconium dichloride,
bis(tetrahydro-1-indenyl)zirconium dimethyl,
(n-propyl cyclopentadienyl, pentamethyl cyclopentadienyl) zirconium dichloride, and
(n-propyl cyclopentadienyl, pentamethyl cyclopentadienyl) zirconium dimethyl.

In at least one aspect, the catalyst compound may be selected from:
dimethylsilylbis(tetrahydroindenyl)$M^cX_n$,
dimethylsilyl bis(2-methylindenyl)$M^cX_n$,
dimethylsilyl bis(2-methylfluorenyl)$M^cX_n$,
dimethylsilyl bis(2-methyl-5,7-propylindenyl)$M^cX_n$,
dimethylsilyl bis(2-methyl-4-phenylindenyl)$M^cX_n$,
dimethylsilyl bis(2-ethyl-5-phenylindenyl)$M^cX_n$,
dimethylsilyl bis(2-methyl-4-biphenylindenyl)$M^cX_n$,
dimethylsilylene bis(2-methyl-4-carbazolylindenyl)$M^cX_n$,
rac-dimethylsilyl-bis-(5,6,7,8-tetrahydro-5,5,8,8-tetramethyl-2-methyl-1H-benz(f)indene)$M^cX_n$,
diphenylmethylene (cyclopentadienyl)(fluoreneyl)$M^cX_n$,
bis(methylcyclopentadienyl)$M^cX_n$,
rac-dimethylsiylbis(2-methyl,3-propyl indenyl)$M^cX_n$,
dimethylsilylbis(indenyl)$M^cX_n$,
rac-meso-diphenylsilyl-bis(n-propylcyclopentadienyl) $M^cX_n$, 1,1'-bis(4-triethylsilylphenyl)methylene-(cyclopentadienyl)(3,8-di-tertiary-butyl-1 fluorenyl)$M^cX_n$ (bridge is considered the 1 position),
bis-trimethylsilylphenyl-methylene(cyclopentadienyl)(di-t-butylfluorenyl)$M^cX_n$,
bis-trimethylsilylphenyl-methylene(cyclopentadienyl)(fluorenyl)$M^cX_n$,
bisphenylmethylene(cyclopentadienyl)(dimethylfluorenyl)$M^cX_n$,
bis(n-propylcyclopentadienyl)$M^cX_n$,
bis(n-butylcyclopentadienyl)$M^cX_n$,
bis(n-pentylcyclopentadienyl)$M^cX_n$,
(n-propyl cyclopentadienyl)(n-butylcyclopentadienyl)$M^cX_n$,
bis[(2-trimethylsilylethyl)cyclopentadienyl]$M^cX_n$,
bis(trimethylsilyl cyclopentadienyl)$M^cX_n$,
dimethylsilylbis(n-propylcyclopentadienyl)$M^cX_n$,
dimethylsilylbis(n-butylcyclopentadienyl)$M^cX_n$,
bis(1-n-propyl-2-methylcyclopentadienyl)$M^cX_n$,
(n-propylcyclopentadienyl)(1-n-propyl-3-n-butylcyclopentadienyl)$M^cX_n$,
bis(1-methyl, 3-n-butyl cyclopentadienyl)$M^cX_n$,
bis(indenyl)$M^cX_n$,
dimethylsilyl (tetramethylcyclopentadienyl)(cyclododecylamido)$M^cX_n$,
dimethylsilyl (tetramethylcyclopentadienyl)(t-butylamido)$M^cX_n$,
1,1'-bis(4-triethylsilylphenyl)(methylene)(cyclopentadienyl)(fluorenyl)$M^cX_n$;
μ-$(CH_3)_2$Si(cyclopentadienyl)(1-adamantylamido)$M^cX_n$,
μ-$(CH_3)_2$Si(3-tertbutylcyclopentadienyl)(1-adamantylamido)$M^cX_n$,
μ-$(CH_3)_2$(tetramethylcyclopentadienyl)(1-adamantylamido)$M^cX_n$,
μ-$(CH_3)_2$Si(tetramethylcyclopentadienyl)(1-adamantylamido)$M^cX_n$,
μ-$(CH_3)_2$C(tetramethylcyclopentadienyl)(1-adamantylamido)$M^cX_n$,
μ-$(CH_3)_2$Si(tetramethylcyclopentadienyl)(1-tertbutylamido)$M^cX_n$,
μ-$(CH_3)_2$Si(fluorenyl)(1-tertbutylamido)$M^cX_n$,
μ-$(CH_3)_2$Si(tetramethylcyclopentadienyl)(1-cyclododecylamido)$M^cX_n$,
μ-$(C_6H_5)_2$C(tetramethylcyclopentadienyl)(1-cyclododecylamido)$M^cX_n$,
μ-$(CH_3)_2$Si($\eta^5$-2,6,6-trimethyl-1,5,6,7-tetrahydro-s-indacen-1-yl)(tertbutylamido)$M^cX_n$,
where $M^c$ is selected from Ti, Zr, and Hf; where X is selected from the group consisting of halogens, hydrides, $C_{1-12}$ alkyls, $C_{2-12}$ alkenyls, $C_{6-12}$ aryls, $C_{7-20}$ alkylaryls, $C_{1-12}$ alkoxys, $C_{6-16}$ aryloxys, $C_{7-18}$ alkylaryloxys, $C_{1-12}$ fluoroalkyls, $C_{6-12}$ fluoroaryls, and $C_{1-12}$ heteroatom-containing hydrocarbons, substituted derivatives thereof, and combinations thereof, and where n is zero or an integer from 1 to 4, preferably X is selected from halogens (such as bromide, fluoride, chloride), or $C_1$ to $C_{20}$ alkyls (such as methyl, ethyl, propyl, butyl, and pentyl) and n is 1 or 2, preferably 2.

In other embodiments of the invention, the catalyst is one or more of:
bis(1-methyl, 3-n-butyl cyclopentadienyl)$M^c(R)_2$;
dimethylsilyl bis(indenyl)$M^c(R)_2$;
bis(indenyl)$M^c(R)_2$;
dimethylsilyl bis(tetrahydroindenyl)$M^c(R)_2$;
bis(n-propylcyclopentadienyl)$M^c(R)_2$;
dimethylsilyl (tetramethylcyclopentadienyl)(cyclododecylamido)$M^c(R)_2$;
dimethylsilyl (tetramethylcyclopentadienyl)(cyclododecylamido)$M^c(R)_2$;
dimethylsilyl (tetramethylcyclopentadienyl)(t-butylamido)$M^c(R)_2$;
dimethylsilyl (tetramethylcyclopentadienyl)(t-butylamido)$M^c(R)_2$;
1,1'-bis(4-triethylsilylphenyl)(methylene)(cyclopentadienyl)(fluorenyl)$M^c(R)_2$;
μ-$(CH_3)_2$Si(cyclopentadienyl)(1-adamantylamido)$M^c(R)_2$;
μ-$(CH_3)_2$Si(3-tertbutylcyclopentadienyl)(1-adamantylamido)$M^c(R)_2$;
μ-$(CH_3)_2$(tetramethylcyclopentadienyl)(1-adamantylamido)$M^c(R)_2$;
μ-$(CH_3)_2$Si(tetramethylcyclopentadienyl)(1-adamantylamido)$M^c(R)_2$;
μ-$(CH_3)_2$C(tetramethylcyclopentadienyl)(1-adamantylamido)$M^c(R)_2$;
μ-$(CH_3)_2$Si(tetramethylcyclopentadienyl)(1-tertbutylamido)$M^c(R)_2$;
μ-$(CH_3)_2$Si(fluorenyl)(1-tertbutylamido)$M^c(R)_2$;
μ-$(CH_3)_2$Si(tetramethylcyclopentadienyl)(1-cyclododecylamido)$M^c(R)_2$;
μ-$(C_6H_5)_2$C(tetramethylcyclopentadienyl)(1-cyclododecylamido)$M^c(R)_2$;
μ-$(CH_3)_2$Si($\eta^5$-2,6,6-trimethyl-1,5,6,7-tetrahydro-s-indacen-1-yl)(tertbutylamido)$M^c(R)_2$; where $M^c$ is selected from Ti, Zr, and Hf; and R is selected from halogen or $C_1$ to $C_5$ alkyl.

In preferred aspects of the application, the catalyst compound is one or more of:
dimethylsilyl (tetramethylcyclopentadienyl)(cyclododecylamido)titanium dimethyl;
dimethylsilyl (tetramethylcyclopentadienyl)(cyclododecylamido)titanium dimethyl;
dimethylsilyl (tetramethylcyclopentadienyl)(t-butylamido)titanium dimethyl;
dimethylsilyl (tetramethylcyclopentadienyl)(t-butylamido)titanium dimethyl;
μ-$(CH_3)_2$Si(cyclopentadienyl)(1-adamantylamido)titanium dimethyl;
μ-$(CH_3)_2$Si(3-tertbutylcyclopentadienyl)(1-adamantylamido)titanium dimethyl;
μ-$(CH_3)_2$(tetramethylcyclopentadienyl)(1-adamantylamido)titanium dimethyl;
μ-$(CH_3)_2$Si(tetramethylcyclopentadienyl)(1-adamantylamido)titanium dimethyl;
μ-$(CH_3)_2$C(tetramethylcyclopentadienyl)(1-adamantylamido)titanium dimethyl;
μ-$(CH_3)_2$Si(tetramethylcyclopentadienyl)(1-tertbutylamido)titanium $dimethyl_2$;
μ-$(CH_3)_2$Si(fluorenyl)(1-tertbutylamido)titanium dimethyl;
μ-$(CH_3)_2$Si(tetramethylcyclopentadienyl)(1-cyclododecylamido)titanium dimethyl;
μ-$(C_6H_5)_2$C(tetramethylcyclopentadienyl)(1-cyclododecylamido)titanium dimethyl; and/or
μ-$(CH_3)_2$Si($\eta^5$-2,6,6-trimethyl-1,5,6,7-tetrahydro-s-indacen-1-yl)(tertbutylamido)titanium dimethyl.

In at least one aspect, the catalyst is rac-dimethylsilyl-bis(indenyl)hafnium dimethyl and/or 1,1'-bis(4-triethylsilylphenyl)methylene-(cyclopentadienyl)(3,8-di-tertiary-butyl-1-fluorenyl)hafnium dimethyl and/or dimethylsilyl bis(tetrahydroindenyl)zirconium dimethyl.

In at least one embodiment, the catalyst compound is one or more of:
bis(1-methyl, 3-n-butyl cyclopentadienyl)hafnium dimethyl,
bis(1-methyl, 3-n-butyl cyclopentadienyl)zirconium dimethyl, dimethylsilyl bis(indenyl)zirconium dimethyl,
dimethylsilyl bis(indenyl)hafnium dimethyl,
bis(indenyl)zirconium dimethyl,
bis(indenyl)hafnium dimethyl,
dimethylsilyl bis(tetrahydroindenyl)zirconium dimethyl,
bis(n-propylcyclopentadienyl)zirconium dimethyl,
dimethylsilylbis(tetrahydroindenyl)hafnium dimethyl,
dimethylsilyl bis(2-methylindenyl)zirconium dimethyl,
dimethylsilyl bis(2-methylfluorenyl)zirconium dimethyl,
dimethylsilyl bis(2-methylindenyl)hafnium dimethyl,
dimethylsilyl bis(2-methylfluorenyl)hafnium dimethyl,
dimethylsilyl bis(2-methyl-5,7-propylindenyl) zirconium dimethyl,
dimethylsilyl bis(2-methyl-4-phenylindenyl) zirconium dimethyl,
dimethylsilyl bis(2-ethyl-5-phenylindenyl) zirconium dimethyl,
dimethylsilyl bis(2-methyl-4-biphenylindenyl) zirconium dimethyl,
dimethylsilylene bis(2-methyl-4-carbazolylindenyl) zirconium dimethyl,
rac-dimethylsilyl-bis-(5,6,7,8-tetrahydro-5,5,8,8-tetramethyl-2-methyl-1H-benz(f)indene)hafnium dimethyl,
diphenylmethylene (cyclopentadienyl)(fluoreneyl)hafnium dimethyl,
bis(methylcyclopentadienyl)zirconium dimethyl,
rac-dimethylsiylbis(2-methyl,3-propyl indenyl)hafnium dimethyl,
dimethylsilylbis(indenyl)hafnium dimethyl,
dimethylsilylbis(indenyl)zirconium dimethyl,
dimethyl rac-dimethylsilyl-bis-(5,6,7,8-tetrahydro-5,5,8,8-tetramethyl-2-methyl-1H-benz(f)indene)hafnium dimethyl,
rac-meso-diphenylsilyl-bis(n-propylcyclopentadienyl)hafnium dimethyl,
1,1'-bis(4-triethylsilylphenyl)methylene-(cyclopentadienyl)(3,8-di-tertiary-butyl-1 fluorenyl)hafnium dimethyl,
1,1'-bis(4-triethylsilylphenyl)methylene-(cyclopentadienyl)(3,8-di-tertiary-butyl-1 fluorenyl)hafnium $X_n$ (bridge is considered the 1 position),
bis-trimethylsilylphenyl-methylene(cyclopentadienyl)(di-t-butylfluorenyl)hafnium dimethyl,
bis-trimethylsilylphenyl-methylene(cyclopentadienyl)(fluorenyl)hafnium dimethyl,
bisphenylmethylene(cyclopentadienyl)(dimethylfluorenyl) hafnium dimethyl,
bis(n-propylcyclopentadienyl)hafnium dimethyl,
bis(n-butylcyclopentadienyl)hafnium dimethyl,
bis(n-pentylcyclopentadienyl)hafnium dimethyl,
(n-propyl cyclopentadienyl)(n-butylcyclopentadienyl)hafnium dimethyl,
bis[(2-trimethylsilylethyl)cyclopentadienyl]hafnium dimethyl,
bis(trimethylsilyl cyclopentadienyl)hafnium dimethyl,
dimethylsilylbis(n-propylcyclopentadienyl)hafnium dimethyl,
dimethylsilylbis(n-butylcyclopentadienyl)hafnium dimethyl,
bis(1-n-propyl-2-methylcyclopentadienyl)hafnium dimethyl, and
(n-propylcyclopentadienyl)(1-n-propyl-3-n-butylcyclopentadienyl)hafnium dimethyl,
bis(n-propylcyclopentadienyl)hafnium dimethyl,
bis(n-butylcyclopentadienyl)hafnium dimethyl,
bis(n-pentylcyclopentadienyl)hafnium dimethyl,
(n-propyl cyclopentadienyl)(n-butylcyclopentadienyl)hafnium dimethyl,
bis[(2-trimethylsilylethyl)cyclopentadienyl]hafnium dimethyl,
bis(trimethylsilyl cyclopentadienyl)hafnium dimethyl,
dimethylsilylbis(n-propylcyclopentadienyl)hafnium dimethyl,
dimethylsilylbis(n-butylcyclopentadienyl)hafnium dimethyl,
bis(1-n-propyl-2-methylcyclopentadienyl)hafnium dimethyl,
(n-propylcyclopentadienyl)(1-n-propyl-3-n-butylcyclopentadienyl)hafnium dimethyl, and
dimethylsilyl(3-n-propylcyclopentadienyl)(tetramethylcyclopentadienyl)zirconium dimethyl.

Exemplary metallocene catalysts used for polymerizations of the present disclosure may be represented by the Formulas (CAT-1), (CAT-2), (CAT-3), and (CAT-4):

(CAT-1)

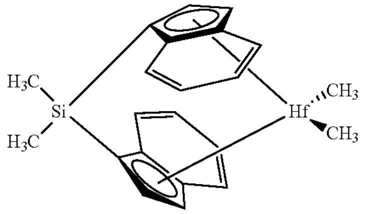

(CAT-2)

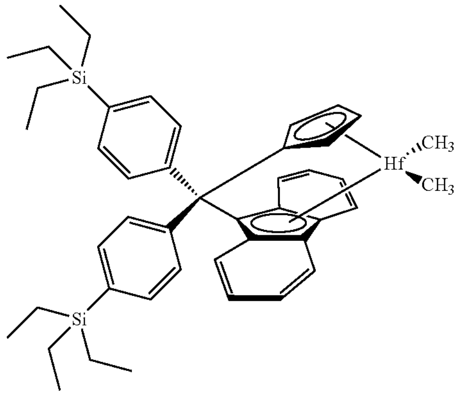

(CAT-3)

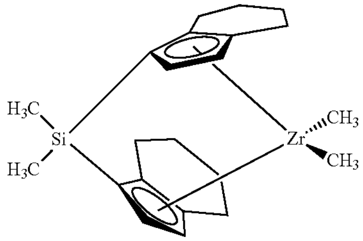

-continued (CAT-4)

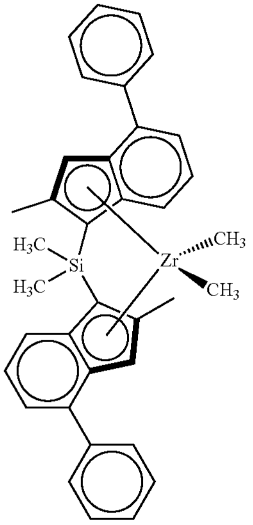

Non-Metallocene Catalyst Compounds

Transition metal complexes for polymerization processes can include any olefin polymerization catalyst. Suitable catalyst components may include "non-metallocene complexes" that are defined to be transition metal complexes that do not feature a cyclopentadienyl anion or substituted cyclopentadienyl anion donors (e.g., cyclopentadienyl, fluorenyl, indenyl, methylcyclopentadienyl). Examples of families of non-metallocene complexes that may be suitable can include late transition metal pyridylbisimines (e.g., U.S. Pat. No. 7,087,686), group 4 pyridyldiamidos (e.g., U.S. Pat. No. 7,973,116), quinolinyldiamidos (e.g., US Pub. No. 2018/0002352 A1), pyridylamidos (e.g., U.S. Pat. No. 7,087,690), phenoxyimines (e.g., Makio, H. et al. (2009) "Development and Application of F Catalysts for Olefin Polymerization: Unique Catalysis and Distinctive Polymer Formation," *Accounts of Chemical Research*, v.42(10), pp. 1532-1544), and bridged bi-aromatic complexes (e.g., U.S. Pat. No. 7,091,292), the disclosures of which are incorporated herein by reference.

Catalyst complexes that are suitable for use in combination with the activators described herein include: diphenolate complexes; oxadiazolylphenolate complexes; diethylenetriamine complexes; and oxybis(ethylamine) complexes; or any combination thereof, including any combination with metallocene complexes.

The term "bisphenolate complex" or "bisphenolate catalyst" refers to a class of coordination complexes described in U.S. Pat. No. 6,841,502, WO 2017/004462, and WO 2006/020624 that feature a dianionic tetradentate ligand that is coordinated to a metal center through two neutral Lewis basic donor atoms (e.g., oxygen bridge moieties) and two anionic aryloxy (i.e., deprotonated phenoxy) donors.

The term "phenoxyimine complex" or "phenoxyimine catalyst" refers to a class of coordination complexes described in EP 0 874 005 that feature a monoanionic bidentate ligand that is coordinated to a metal center through one neutral Lewis basic donor atom (e.g., an imine moiety) and an anionic aryloxy (i.e., deprotonated phenoxy) donor. Typically two of these bidentate phenoxyimine ligands are coordinated to a group 4 metal to form a complex that is useful as a catalyst component.

The term "oxadiazolylphenolate complex" or "oxadiazolylphenolate catalyst" refers to a class of coordination complexes that feature a metal center coordinated to a bidentate oxadiazolylphenolate anion via the phenolate oxygen and the oxadiazolyl nitrogen atom and two other anionic ligands.

The term "diethylenetriamine complex" or "diethylenetriamine complex" refers to a class of coordination complexes that feature a metal center coordinated to a tridentate diethylenetriamine ligand and two other anionic ligands.

The term "oxybis(ethylamine) complex" or "oxybis(ethylamine) complex" refers to a class of coordination complexes that feature a metal center coordinated to a tridentate oxybis(ethylamine) ligand via the nitrogen of two amino groups and the oxygen of the ether group and two other anionic ligands.

Suitable non-metallocene complexes can include zirconium and hafnium non-metallocene complexes. In at least one embodiment, non-metallocene complexes for the present disclosure include group 4 non-metallocene complexes including four anionic donor atoms and one or two neutral donor atoms. Suitable non-metallocene complexes for the present disclosure include group 4 non-metallocene complexes including an anionic phenolate donor. Suitable non-metallocene complexes for the present disclosure include group 4 non-metallocene complexes including an anionic amino donor atom. Suitable non-metallocene complexes for the present disclosure include group 4 non-metallocene complexes including two anionic aryloxide donor atoms and two additional neutral donor atoms.

A catalyst compound can be diphenolate transition metal complex represented by Formula (V):

(V)

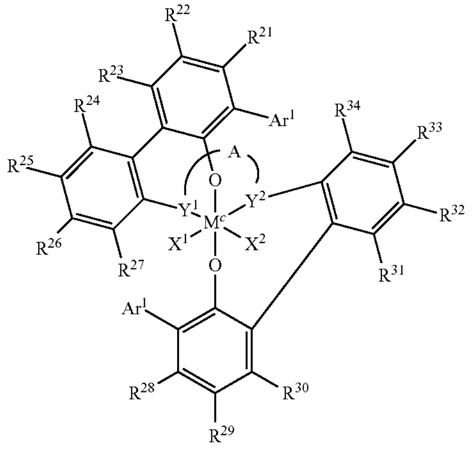

wherein:

- $M^c$ is a group 3, 4, 5, 6, 7, 8, 9, 10, 11, or 12 metal, such as a group 4 metal;
- $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ are independently hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring:
- A is a $C_1$-$C_{50}$ alkyl group;
- $Y^1$ and $Y^2$ are independently selected from O, S, $NR^a$ and $PR^a$ wherein $R^a$ is optionally substituted hydrocarbyl;
- $Ar^1$ is phenyl, naphthyl, biphenyl, anthracenyl, or phenanthrenyl; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, alkylaryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

In at least one aspect, $M^c$ is a group 4 metal, such as zirconium or hafnium, such as $M^c$ is zirconium.

In at least one aspect, $Y^1$ and $Y^2$ are O.

$X^1$ and $X^2$ may be independently alkyl (such as alkyl groups having 1 to 10 carbons, such as methyl, ethyl, propyl, butyl, pentyl, hexyl, heptyl, octyl, nonyl, decyl, and isomers thereof), aryl, alkyaryl (such as benzyl), hydride, alkylsilane, fluoride, chloride, bromide, iodide, triflate, carboxylate, amido (such as $NMe_2$), or alkylsulfonate.

In at least one aspect, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ are independently hydride or alkyl.

$R^{22}$ may be an alkyl group, such as methyl, ethyl, propyl, butyl, pentyl, hexyl, heptyl, octyl, nonyl, decyl, and isomers thereof.

$Ar^1$ may be a biphenyl group.

A may be an alkyl group such as propyl or butyl.

An exemplary catalyst used for polymerizations of the present disclosure may be represented by the Formula (CAT-5).

(CAT-5)

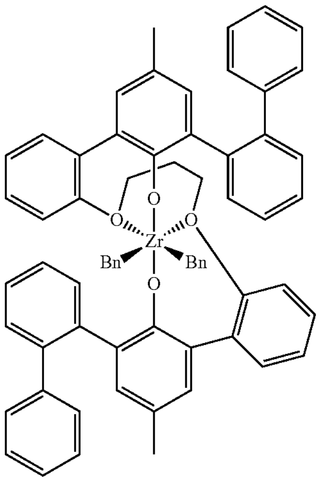

Another exemplary catalyst used for polymerizations of the present disclosure may be represented by the Formula (CAT-6).

(CAT-6)

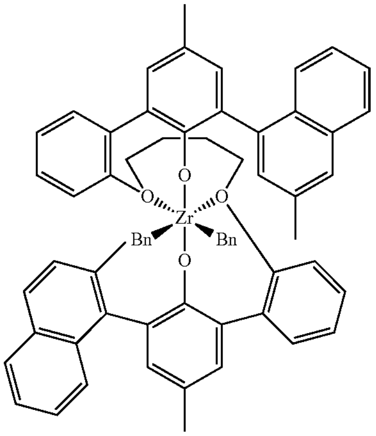

In another aspect, the oxadiazolylphenolate catalyst compound is represented by Formulas (VIa) or (VIb):

(VIa)

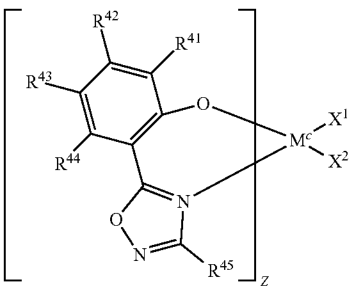

(VIb)

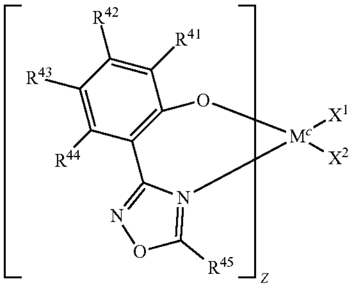

wherein in Formulas (VIa) or (VIb):

$M^c$ is an element selected from group 4 of the Periodic Table of the Elements $R^{41}$, $R^{42}$, $R^{43}$, $R^{44}$, $R^{45}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, subcultured aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atom; or both together can be an olefin, diolefin or aryne ligand; and z is 1, 2, 3, or 4.

In at least one aspect, $M^c$ is a group 4 metal, such as zirconium or hafnium, such as $M^c$ is zirconium.

In at least one aspect, $X^1$ and $X^2$ are independently alkyl (such as alkyl groups having 1 to 10 carbons, such as methyl, ethyl, propyl, butyl, pentyl, hexyl, heptyl, octyl, nonyl, decyl, and isomers thereof), aryl, alkyaryl (such as benzyl), hydride, alkylsilane, fluoride, chloride, bromide, iodide, triflate, carboxylate, amido (such as $NMe_2$), or alkylsulfonate.

In at least one aspect, $R^{41}$, $R^{42}$, $R^{43}$, $R^{44}$, $R^{45}$ are independently hydride, alkyl, substituted alkyl, aryl, or substituted aryl.

$R^{41}$ and $R^{45}$ may be independently substituted aryl groups, such as halogen substituted phenyl or haloalkyl substituted phenyl; $R^{42}$ and $R^{43}$ may be hydrogens; $R^{44}$ may be an alkyl group, such as methyl, ethyl, n-propyl, isopropyl, butyl, butyl, pentyl, hexyl, heptyl, octyl, nonyl, decyl, and isomers thereof.

In at least one aspect, $R^{41}$ may be a fluoroaryl group, such as a meta-trifluorophenyl group; $R^{42}$ and $R^{43}$ may be hydrogens; $R^{43}$ may be a butyl group, such as a tert-butyl group butyl; and $R^{41}$ may be a chloroaryl group, such as a dichlorophenyl group.

An exemplary oxadiazolylphenolate catalyst used for polymerizations of the present disclosure may be represented by the Formula (CAT-7).

(CAT-7)

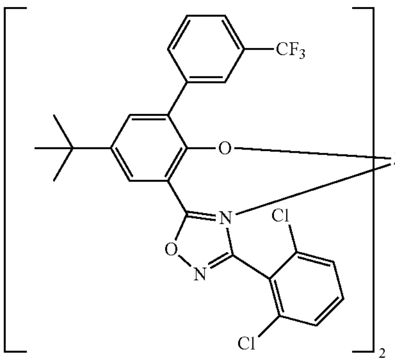

In another aspect, the diethylenetriamine and oxybis (ethylamine) catalyst compounds are represented by Formula (VII):

(VII)

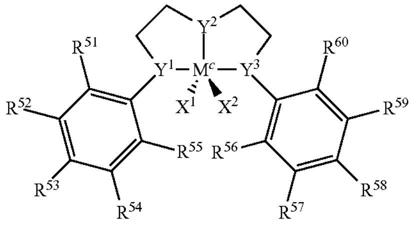

wherein in Formula (VII):

$M^c$ is an element selected from group 4 of the Periodic Table of the Elements $R^{51}$, $R^{52}$, $R^{53}$, $R^{54}$, $R^{55}$, $R^{56}$, $R^{57}$, $R^{58}$, $R^{59}$, $R^{60}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$Y^1$ and $Y^2$ are independently O, N, NH, or S; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

In at least one aspect, $M^c$ is a group 4 metal, such as zirconium or hafnium, such as $M^c$ is zirconium.

In at least one aspect, $Y^1$ and $Y^2$ are independently O or N.

In at least one aspect, $X^1$ and $X^2$ are independently alkyl (such as alkyl groups having 1 to 10 carbons, such as methyl, ethyl, propyl, butyl, pentyl, hexyl, heptyl, octyl, nonyl, decyl, and isomers thereof), aryl, alkyaryl (such as benzyl), hydride, alkylsilane, fluoride, chloride, bromide, iodide, triflate, carboxylate, amido (such as $NMe_2$), or alkylsulfonate.

In at least one aspect, $R^{51}$, $R^{52}$, $R^{53}$, $R^{54}$, $R^{55}$, $R^{56}$, $R^{57}$, $R^{58}$, $R^{59}$, and $R^{60}$ are independently hydride, alkyl, substituted alkyl, aryl, or substituted aryl groups.

In at least one aspect, $R^{51}$, $R^{52}$, $R^{53}$, $R^{54}$, $R^{55}$, $R^{56}$, $R^{57}$, $R^{58}$, $R^{59}$, and $R^{60}$ are alkyl groups, such as methyl groups.

An exemplary oxybis(ethylamine) catalyst used for polymerizations of the present disclosure may be represented by the Formula (CAT-8).

(CAT-8)

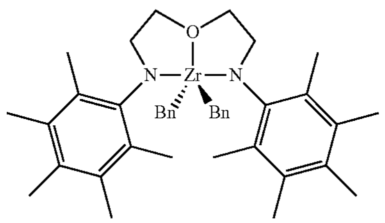

An exemplary diethylenetriamine catalyst used for polymerizations of the present disclosure may be represented by the Formula (CAT-9).

(CAT-9)

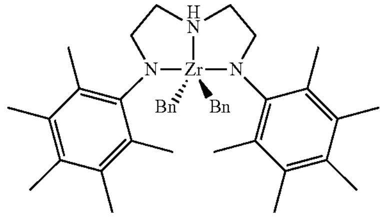

In some aspects, a co-activator is combined with the catalyst compound (such as halogenated catalyst compounds described above) to form an alkylated catalyst compound. Organoaluminum compounds which may be utilized as co-activators include, for example, trialkylaluminum compounds, such as trimethylaluminum, triethylaluminum, triisobutylaluminum, tri-n-hexylaluminum, tri-n-octylaluminum, and the like, or alumoxanes.

In some aspects, two or more different catalyst compounds are present in the catalyst system used herein. In some embodiments, two or more different catalyst compounds are present in the reaction zone where the process (es) described herein occur. When two transition metal compound based catalysts are used in one reactor as a mixed catalyst system, the two transition metal compounds are preferably chosen such that the two are compatible. A simple screening method such as by $^{1}H$ or $^{13}C$ NMR, known to those of ordinary skill in the art, can be used to determine which transition metal compounds are compatible. It is preferable to use the same activator for the transition metal compounds, however, two different activators can be used in combination. If one or more transition metal compounds contain an anionic ligand as a leaving group which is not a hydride, hydrocarbyl, or substituted hydrocarbyl, then the alumoxane or other alkyl aluminum is typically contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Support Materials

In embodiments herein, the catalyst system may comprise a support material. In at least one embodiment, the support material is a porous support material, for example, talc, or inorganic oxides. Other support materials include zeolites, clays, organoclays, or any other suitable organic or inorganic support material and the like, or mixtures thereof.

In at least one embodiment, the support material is an inorganic oxide. Suitable inorganic oxides for use in catalyst systems herein include groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be used, for example, functionalized polyolefins, such as polypropylene. Support materials may include magnesia, titania, zirconia, montmorillonite, phyllosilicate, zeolites, talc, clays, and the like. Also, combinations of these support materials may be used, for example, silica-chromium, silica-alumina, silica-titania, and the like. Support materials also include $Al_2O_3$, $ZrO_2$, $SiO_2$, $SiO_2/Al_2O_3$, $SiO_2/TiO_2$, silica clay, silicon oxide/clay, or mixtures thereof.

It is preferred that the support material, most preferably an inorganic oxide, has a surface area in the range of from about 10 to about 700 $m^2/g$, a pore volume in the range of from about 0.1 to about 4.0 cc/g and an average particle size in the range of from about 5 to about 500 μm. More preferably, the surface area of the support material is in the range of from about 50 to about 500 $m^2/g$, a pore volume of from about 0.5 to about 3.5 cc/g and an average particle size of from about 10 to about 200 μm. Most preferably the surface area of the support material is in the range from about 100 to about 400 $m^2/g$, a pore volume from about 0.8 to about 3.0 cc/g and an average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$). Preferred silicas are marketed under the tradenames of DAVISON™ 952 or DAVISON™ 955 by the Davison Chemical Division of W.R. Grace and Company. In other embodiments DAVISON™ 948 may be used.

The support material should be dry, that is, free of absorbed water. Drying of the support material can be effected by heating or calcining at about 100° C. to about 1,000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material may have at least some reactive hydroxyl (OH) groups to produce supported catalyst systems of this invention. The calcined support material is then contacted with at least one polymerization catalyst system comprising at least one catalyst compound and an activator.

The support material, having reactive surface groups, typically hydroxyl groups, is slurried in a non-polar solvent and the resulting slurry is contacted with a solution of a catalyst compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the catalyst compound is then contacted with the isolated support/activator. In some embodiments, the supported catalyst system is generated in situ. In alternate embodiments, the slurry of the support material is first contacted with the catalyst compound for a period of time in the range of from about 0.5 hours to about 24 hours, from about 2 hours to about 16 hours, or from about 4 hours to about 8 hours. The slurry of the supported catalyst compound is then contacted with the activator solution.

The mixture of the catalyst, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the catalyst compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed. Preferably, aromatic solvents are excluded in the disclosure herein.

In at least one embodiment, the support material comprises a support material treated with an electron-withdrawing anion. The support material can be silica, alumina, silica-alumina, silica-zirconia, alumina-zirconia, aluminum phosphate, heteropolytungstates, titania, magnesia, boria, zinc oxide, mixed oxides thereof, or mixtures thereof; and the electron-withdrawing anion is selected from fluoride, chloride, bromide, phosphate, triflate, bisulfate, sulfate, or any combination thereof.

The electron-withdrawing component used to treat the support material can be any component that increases the Lewis or Brønsted acidity of the support material upon treatment (as compared to the support material that is not treated with at least one electron-withdrawing anion). In at least one embodiment, the electron-withdrawing component is an electron-withdrawing anion derived from a salt, an acid, or other compound, such as a volatile organic compound, that serves as a source or precursor for that anion. Electron-withdrawing anions can be sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or mixtures thereof, or combinations thereof. An electron-withdrawing anion can be fluoride, chloride, bromide, phosphate, triflate, bisulfate, or sulfate, or any combination thereof, at least one embodiment of this application. In at least one embodiment, the electron-withdrawing anion is sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof.

Thus, for example, the support material suitable for use in the catalyst systems of the present disclosure can be one or more of fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or combinations thereof. In at least one embodiment, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, or combinations thereof. In another embodiment, the support material includes alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, or combinations thereof. Further, any of these activator-supports optionally can be treated with a metal ion.

Nonlimiting examples of cations suitable for use in the present disclosure in the salt of the electron-withdrawing anion include ammonium, trialkyl ammonium, tetraalkyl ammonium, tetraalkyl phosphonium, $H^+$, $[H(OEt_2)_2]^+$, or combinations thereof.

Further, combinations of one or more different electron-withdrawing anions, in varying proportions, can be used to tailor the specific acidity of the support material to a desired level. Combinations of electron-withdrawing components can be contacted with the support material simultaneously or individually, and in any order that provides a desired chemically-treated support material acidity. For example, in at least one embodiment, two or more electron-withdrawing anion source compounds in two or more separate contacting steps.

In at least one embodiment of the present disclosure, one example of a process by which a chemically-treated support material is prepared is as follows: a selected support material, or combination of support materials, can be contacted with a first electron-withdrawing anion source compound to form a first mixture; such first mixture can be calcined and then contacted with a second electron-withdrawing anion source compound to form a second mixture; the second mixture can then be calcined to form a treated support material. In such a process, the first and second electron-withdrawing anion source compounds can be either the same or different compounds.

The method by which the oxide is contacted with the electron-withdrawing component, typically a salt or an acid of an electron-withdrawing anion, can include gelling, co-gelling, impregnation of one compound onto another, or combinations thereof. Following a contacting method, the contacted mixture of the support material, electron-withdrawing anion, and optional metal ion, can be calcined.

According to another embodiment of the present disclosure, the support material can be treated by a process comprising: (i) contacting a support material with a first electron-withdrawing anion source compound to form a first mixture; (ii) calcining the first mixture to produce a calcined first mixture; (iii) contacting the calcined first mixture with a second electron-withdrawing anion source compound to form a second mixture; and (iv) calcining the second mixture to form the treated support material.

Polymerization Processes

In embodiments herein, the present disclosure provides polymerization processes where monomer (such as propylene or ethylene), and optionally comonomer, are contacted with a catalyst system comprising an activator and at least one catalyst compound, as described above. The catalyst compound and activator may be combined in any order, and are combined typically prior to contacting with the monomer.

In at least one embodiment, a polymerization process includes a) contacting one or more olefin monomers with a catalyst system comprising: i) an activator and ii) a catalyst compound of the present disclosure. The activator is a non-coordination anion activator. The one or more olefin monomers may be propylene and/or ethylene and the polymerization process further comprises heating the one or more olefin monomers and the catalyst system to 70° C. or more to form propylene polymers or ethylene polymers, such as propylene polymers.

Monomers useful herein include substituted or unsubstituted $C_2$ to $C_{40}$ alpha olefins, such as $C_2$ to $C_{20}$ alpha olefins, such as $C_2$ to $C_{12}$ alpha olefins, such as ethylene, propylene, butene, pentene, hexene, heptene, octene, nonene, decene, undecene, dodecene and isomers thereof. In at least one embodiment, the monomer comprises propylene and an optional comonomers comprising one or more propylene or $C_4$ to $C_{40}$ olefins, such as $C_4$ to $C_{20}$ olefins, such as $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In at least one embodiment, the monomer comprises propylene and an optional comonomers comprising one or more $C_3$ to $C_{40}$ olefins, such as $C_4$ to $C_{20}$ olefins, such as $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include propylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, such as hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, such as norbornene, norbornadiene, and dicyclopentadiene.

In at least one embodiment, one or more dienes are present in the polymer produced herein at up to 10 wt %, such as at 0.00001 to 1.0 wt %, such as 0.002 to 0.5 wt %, such as 0.003 to 0.2 wt %, based upon the total weight of the composition. In some embodiments, 500 ppm or less of diene is added to the polymerization, such as 400 ppm or less, such as 300 ppm or less. In other embodiments at least 50 ppm of diene is added to the polymerization, or 100 ppm or more, or 150 ppm or more.

Diene monomers include any hydrocarbon structure, such as $C_4$ to $C_{30}$, having at least two unsaturated bonds, wherein at least two of the unsaturated bonds are readily incorporated into a polymer by either a stereospecific or a non-stereospecific catalyst(s). The diene monomers can be selected from alpha, omega-diene monomers (i.e. di-vinyl monomers). The diolefin monomers are linear di-vinyl monomers, such as those containing from 4 to 30 carbon atoms. Examples of dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1,000 g/mol). Cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes of the present disclosure can be carried out in any suitable manner. Any suitable suspension, homogeneous, bulk, solution, slurry, or gas phase polymerization process can be used. Such processes can be run in a batch, semi-batch, or continuous mode. Homogeneous polymerization processes and slurry processes can be performed. (A useful homogeneous polymerization process is one where at least 90 wt % of the product is soluble in the reaction media.) A bulk homogeneous process can be used. (An example bulk process is one where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In at least one embodiment, the process is a slurry polymerization process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_4$-$C_{10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In at least one embodiment, the solvent is not aromatic, such that aromatics are present in the solvent at less than 1 wt %, such as less than 0.5 wt %, such as less than 0 wt % based upon the weight of the solvents.

In at least one embodiment, the feed concentration of the monomers and comonomers for the polymerization is 60 vol % solvent or less, such as 40 vol % or less, such as 20 vol % or less, based on the total volume of the feedstream. The polymerization can be performed in a bulk process.

Polymerizations can be performed at any temperature and/or pressure suitable to obtain the desired polymers, such as ethylene and or propylene polymers. Typical temperatures and/or pressures include a temperature in the range of from 0° C. to 300° C., such as 20° C. to 200° C., such as 35° C. to 150° C., such as 40° C. to 120° C., such as 45° C. to 80° C., for example about 74° C., and at a pressure in the range of from 0.35 MPa to 10 MPa, such as 0.45 MPa to 6 MPa, such as 0.5 MPa to 4 MPa.

In a typical polymerization, the run time of the reaction is up to 300 minutes, such as in the range of from 5 to 250 minutes, such as 10 to 120 minutes.

In at least one embodiment, hydrogen is present in the polymerization reactor at a partial pressure of 0.001 to 50 psig (0.007 to 345 kPa), such as from 0.01 to 25 psig (0.07 to 172 kPa), such as 0.1 to 10 psig (0.7 to 70 kPa).

In at least one embodiment, the activity of the catalyst is at least 50 g/mmol/hour, preferably 500 or more g/mmol/hour, preferably 5,000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In at least one embodiment, a catalyst system of the present disclosure is capable of producing a polyolefin. In at least one embodiment, a polyolefin is a homopolymer of ethylene or propylene or a copolymer of ethylene such as a copolymer of ethylene having from 0.1 to 25 wt % (such as from 0.5 to 20 wt %, such as from 1 to 15 wt %, such as from 5 to 17 wt %) of ethylene with the remainder balance being one or more $C_3$ to $C_{20}$ olefin comonomers (such as $C_3$ to $C_{12}$ alpha-olefin, such as propylene, butene, hexene, octene, decene, dodecene, such as propylene, butene, hexene, octene). A polyolefin can be a copolymer of propylene such as a copolymer of propylene having from 0.1 to 25 wt % (such as from 0.5 to 20 wt %, such as from 1 to 15 wt %, such as from 3 to 10 wt %) of propylene and from 99.9 to 75 wt % of one or more of $C_2$ or $C_4$ to $C_{20}$ olefin comonomer (such as ethylene or $C_4$ to $C_{12}$ alpha-olefin, such as butene, hexene, octene, decene, dodecene, such as ethylene, butene, hexene, octene).

In at least one embodiment, a catalyst system of the present disclosure is capable of producing polyolefins, such as polyethylene, polypropylene (e.g., iPP), or ethylene-octene copolymers, having an Mw from 500 to 2,500,000, such as from 5,000 to 2,000,000, such as from 25,000 to 1,500,000, such as from 40,000 to 1,000,000, such as from 50,000 to 900,000, such as from 60,000 to 800,000.

In at least one embodiment, a catalyst system of the present disclosure is capable of producing polyolefins, such as polyethylene, polypropylene (e.g., iPP), or ethylene-octene copolymers having an Mw/Mn value from 1 to 10, such as from 1.5 to 9, such as from 2 to 7, such as from 2 to 4, such as from 2.5 to 3, for example about 2.

In at least one embodiment, a catalyst system of the present disclosure is capable of producing polyolefins, such as polyethylene, polypropylene (e.g., iPP), or ethylene-octene copolymers having a melting temperature (Tm) of less than 140° C., or 30° C. to 150° C., such as 40° C. to 140° C., such as 45° C. to 135° C., such as 50° C. to 135° C.

In at least one embodiment, little or no scavenger is used in the process to produce polymer, such as propylene polymer. Scavenger (such as trialkyl aluminum) can be present at zero mol %, alternately the scavenger is present at a molar ratio of scavenger metal to transition metal of less than 100:1, such as less than 50:1, such as less than 15:1, such as less than 10:1.

In at least one embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1; 5) the polymerization preferably occurs in one reaction zone; 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); 7) optionally scavengers (such as trialkyl aluminum compounds) are absent (e.g. present at zero mol %, alternately the scavenger is present at a molar ratio of scavenger metal to transition metal of less than 100:1, preferably less than 50:1, preferably less than 15:1, preferably less than 10:1); and 8) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound.

In at least one embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In at least one embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), hydrogen, or aluminum alkyls. Useful chain transfer agents are typically alkylalumoxanes, a compound represented by the formula $AlR_3$, $ZnR_2$ (where each R is, independently, a $C_1$-$C_8$ aliphatic radical, such as methyl, ethyl, propyl, butyl, phenyl, hexyl, octyl or an isomer thereof) or a combination thereof, such as diethylzinc, methylalumoxane, trimethylaluminum, triisobutylaluminum, trioctylaluminum, or a combination thereof.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See, for example, U.S. Pat. Nos. 4,543,399; 4,588,790; 5,028,670; 5,317,036; 5,352,749; 5,405,922; 5,436,304; 5,453,471; 5,462,999; 5,616,661; and 5,668,228; all of which are fully incorporated herein by reference.)

Slurry Phase Polymerization

A slurry polymerization process generally operates between 1 to about 50 atmosphere pressure range (15 psi to 735 psi, 103 kPa to 5,068 kPa) or even greater and temperatures in the range of 0° C. to about 120° C. In a slurry polymerization, a suspension of solid, particulate polymer is formed in a liquid polymerization diluent medium to which monomer and comonomers, along with catalysts, are added. The suspension including diluent is intermittently or continuously removed from the reactor where the volatile components are separated from the polymer and recycled, optionally after a distillation, to the reactor. The liquid diluent used in the polymerization medium is typically an alkane having from 3 to 7 carbon atoms, such as a branched alkane. The medium employed should be liquid under the conditions of polymerization and relatively inert. When a propane medium is used, the process must be operated above the reaction diluent critical temperature and pressure. For example, a hexane or an isobutane medium is employed.

In at least one embodiment, a polymerization process is a particle form polymerization, or a slurry process, where the temperature is kept below the temperature at which the polymer goes into solution. Such technique is well known in the art, and described in for instance U.S. Pat. No. 3,248,179 which is fully incorporated herein by reference. The temperature in the particle form process can be from about 85° C. to about 110° C. Two example polymerization methods for the slurry process are those using a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isohexane or as a dry free flowing powder, is injected regularly to the reactor loop, which is itself filled with circulating slurry of growing polymer particles in a diluent of isohexane containing monomer and optional comonomer. Hydrogen, optionally, may be added as a molecular weight control. (In one embodiment hydrogen is added from 50 ppm to 500 ppm, such as from 100 ppm to 400 ppm, such as 150 ppm to 300 ppm.)

The reactor may be maintained at a pressure of 2,000 kPa to 5,000 kPa, such as from 3,620 kPa to 4,309 kPa, and at a temperature of from about 60° C. to about 120° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isohexane diluent and all unreacted monomer and comonomer. The resulting hydrocarbon free powder is then compounded for use in various applications.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Useful chain transfer agents are typically alkylalumoxanes, a compound represented by the formula $AlR_3$, $ZnR_2$ (where each R is, independently, a $C_1$-$C_8$ hydrocarbyl, such as methyl, ethyl, propyl, butyl, penyl, hexyl octyl or an isomer thereof). Examples can include diethylzinc, methylalumoxane, trimethylaluminum, triisobutylaluminum, trioctylaluminum, or a combination thereof.

Solution Polymerization

A solution polymerization is a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are typically not turbid as described in Oliveira, J. V. et al. (2000) "High-Pressure Phase Equilibria for Polypropylene-Hydrocarbon Systems," *Ind. Eng. Chem. Res.*, v.39, pp. 4627-4633. Generally solution polymerization involves polymerization in a continuous reactor in which the polymer formed and the starting monomer and catalyst materials supplied, are agitated to reduce or avoid concentration gradients and in which the monomer acts as a diluent or solvent or in which a hydrocarbon is used as a diluent or solvent. Suitable processes typically operate at temperatures from about 0° C. to about 250° C., such as about 10° C. to about 150° C., such as about 40° C. to about 140° C., such as about 50° C. to about 120° C., and at pressures of about 0.1 MPa or more, such as 2 MPa or more. The upper pressure limit is not critically constrained but typically can be about 200 MPa or less, such as 120 MPa or less. Temperature control in the reactor can generally be obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds can also be used. The purity, type, and amount of solvent can be optimized for the maximum catalyst productivity for a particular type of polymerization. The solvent can be also introduced as a catalyst carrier. The solvent can be introduced as a gas phase or as a liquid phase depending on the pressure and temperature. Advantageously, the solvent can be kept in the liquid phase and introduced as a liquid. Solvent can be introduced in the feed to the polymerization reactors.

Polyolefin Products

The present disclosure also provides compositions of matter which can be produced by the methods described herein.

In at least one embodiment, a polyolefin is a propylene homopolymer, an ethylene homopolymer or an ethylene copolymer, such as propylene-ethylene and/or ethylene-alphaolefin (such as $C_4$ to $C_{20}$) copolymer (such as an ethylene-hexene copolymer or an ethylene-octene copolymer). A polyolefin can have an Mw/Mn of greater than 1.

In at least one embodiment, a polyolefin is a homopolymer of ethylene or propylene or a copolymer of ethylene such as a copolymer of ethylene having from 0.1 to 25 wt % (such as from 0.5 to 20 wt %, such as from 1 to 15 wt %, such as from 5 to 17 wt %) of ethylene with the remainder balance being one or more $C_3$ to $C_{20}$ olefin comonomers (such as $C_3$ to $C_{12}$ alpha-olefin, such as propylene, butene, hexene, octene, decene, dodecene, such as propylene, butene, hexene, octene). A polyolefin can be a copolymer of propylene such as a copolymer of propylene having from 0.1 to 25 wt % (such as from 0.5 to 20 wt %, such as from 1 to 15 wt %, such as from 3 to 10 wt %) of propylene and from 99.9 to 75 wt % of one or more of $C_2$ or $C_4$ to $C_{20}$ olefin comonomer (such as ethylene or $C_4$ to $C_{12}$ alpha-olefin, such as butene, hexene, octene, decene, dodecene, such as ethylene, butene, hexene, octene).

In at least one embodiment, a catalyst system of the present disclosure is capable of producing polyolefins, such as polyethylene, polypropylene (e.g., iPP), or ethylene-octene copolymers, having an Mw from 500 to 2,500,000, such as from 20,000 to 2,000,000, such as from 30,000 to 1,500,000, such as from 40,000 to 1,000,000, such as from 50,000 to 900,000, such as from 60,000 to 800,000.

In at least one embodiment, a catalyst system of the present disclosure is capable of producing polyolefins, such as polyethylene, polypropylene (e.g., iPP), or ethylene-octene copolymers having an Mw/Mn value from 1 to 10, such as from 1.5 to 9, such as from 2 to 7, such as from 2 to 4, such as from 2.5 to 3, for example about 2.

In at least one embodiment, a catalyst system of the present disclosure is capable of producing polyolefins, such as polyethylene, polypropylene (e.g., iPP), or ethylene-octene copolymers having a melting temperature (Tm) of less than 140° C., or 30° C. to 150° C., such as 40° C. to 140° C., such as 45° C. to 135° C., such as 50° C. to 135° C.

In at least one embodiment, a polymer of the present disclosure has a $g'_{vis}$ of greater than 0.9, such as greater than 0.92, such as greater than 0.95.

In at least one embodiment, the polymer is an ethylene copolymer, and the comonomer is octene, at a comonomer content of from 1 wt % to 18 wt % octene, such as from 5 wt % to 15 wt %, such as from 8 wt % to 13 wt %, such as from 9 wt % to 12 wt %.

In at least one embodiment, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

Unless otherwise indicated Mw, Mn, MWD are determined by GPC as described in US 2006/0173123 page 24-25, paragraphs [0334] to [0341].

In at least one embodiment, the polymer produced herein has a composition distribution breadth index (CDBI) of 50% or more, such as 60% or more, such as 70% or more. CDBI is a measure of the composition distribution of monomer within the polymer chains and is measured by the procedure described in PCT publication WO1993/003093, published Feb. 18, 1993, specifically columns 7 and 8 as well as in Wild, L. et al. (1982) "Determinatino of Branching Distributions in Polyethylene and Ethylene Copolymers," *J. Poly. Sci., Poly. Phys. Ed.*, v.20(3), pp. 441-455; and U.S. Pat. No. 5,008,204, including that fractions having a weight average molecular weight (Mw) below 15,000 are ignored when determining CDBI.

Copolymer of the present disclosure can have a reversed comonomer index. The reversed-co-monomer index (RCI, m) is computed from x2 (mol % co-monomer $C_3$, $C_4$, $C_6$, $C_8$, etc.), as a function of molecular weight, where x2 is obtained from the following expression in which n is the number of carbon atoms in the comonomer (3 for $C_3$, 4 for $C_4$, 6 for $C_6$, etc.):

$$x2 = -\frac{200w2}{-100n - 2w2 + nw2}.$$

Then the molecular-weight distribution, W(z) where $Z=\log_{10}$ M, is modified to W'(z) by setting to 0 the points in W that are less than 5% of the maximum of W; this is to effectively remove points for which the S/N in the composition signal is low. Also, points of W' for molecular weights below 2000 gm/mole are set to 0. Then W' is renormalized so that $$1 = \int_{-\infty}^{\infty} W' dz$$

and a modified weight-average molecular weight ($M_w'$) is calculated over the effectively reduced range of molecular weights as follows:

$$M_w' = \int_{-\infty}^{\infty} 10^z * W' dz.$$

The RCI,m is then computed as:

$$RCI, m = \int_{-\infty}^{\infty} x2(10^z - M_w')W' dz.$$

A reversed-co-monomer index (RCI,w) is also defined on the basis of the weight fraction co-monomer signal (w2/100) and is computed as follows:

$$RCI, w = \int_{-\infty}^{\infty} \frac{w2}{100}(10^z - M_w')W' dz.$$

Note that in the above definite integrals the limits of integration are the widest possible for the sake of generality; however, in reality the function is only integrated over a finite range for which data is acquired, considering the function in the rest of the non-acquired range to be 0. Also, by the manner in which W' is obtained, it is possible that W' is a discontinuous function, and the above integrations need to be done piecewise.

Three co-monomer distribution ratios are also defined on the basis of the % weight (w2) comonomer signal, denoted as CDR-1,w, CDR-2,w, and CDR-3,w, as follows:

$$CDR\text{-}1, w = \frac{w2(Mz)}{w2(Mw)}$$

$$CDR\text{-}2, w = \frac{w2(Mz)}{w2\left(\frac{Mw + Mn}{2}\right)}$$

$$CDR\text{-}3, w = \frac{w2\left(\frac{Mz + Mw}{2}\right)}{w2\left(\frac{Mw + Mn}{2}\right)}$$

where w2(Mw) is the % weight co-monomer signal corresponding to a molecular weight of Mw, w2(Mz) is the % weight co-monomer signal corresponding to a molecular weight of Mz, w2[(Mw+Mn)/2)] is the % weight co-monomer signal corresponding to a molecular weight of (Mw+Mn)/2, and w2[(Mz+Mw)/2] is the % weight co-monomer signal corresponding to a molecular weight of Mz+Mw/2, where Mw is the weight-average molecular weight, Mn is the number-average molecular weight, and Mz is the z-average molecular weight.

Accordingly, the co-monomer distribution ratios can be also defined utilizing the % mole co-monomer signal, CDR-1,m, CDR-2,m, CDR-3,m, as:

$$CDR\text{-}1, m = \frac{x2(Mz)}{x2(Mw)}$$

$$CDR\text{-}2, m = \frac{x2(Mz)}{x2\left(\frac{Mw + Mn}{2}\right)}$$

$$CDR\text{-}3, m = \frac{x2\left(\frac{Mz + Mw}{2}\right)}{x2\left(\frac{Mw + Mn}{2}\right)}$$

where x2(Mw) is the % mole co-monomer signal corresponding to a molecular weight of Mw, x2(Mz) is the % mole co-monomer signal corresponding to a molecular weight of Mz, x2[(Mw+Mn)/2)] is the % mole co-monomer signal corresponding to a molecular weight of (Mw+Mn)/2, and x2[(Mz+Mw)/2] is the % mole co-monomer signal corresponding to a molecular weight of Mz+Mw/2, where Mw is the weight-average molecular weight, Mn is the number-average molecular weight, and Mz is the z-average molecular weight.

In at least one embodiment of the present disclosure, the polymer produced by the processes described herein includes ethylene and one or more comonomers and the polymer has: 1) an RCI,m of 30 or more (alternatively from 30 to 250).

Molecular Weight, Comonomer Composition and Long Chain Branching Determination by Polymer Char GPC-IR with Multiple Detectors The distribution and the moments of molecular weight (Mw, Mn, Mw/Mn, etc.), the comonomer content ($C_2$, $C_3$, $C_6$, etc.) and the long chain branching (g') are determined by using a high temperature Gel Permeation Chromatography (Polymer Char GPC-IR) equipped with a multiple-channel band-filter based Infrared detector IR5, an 18-angle light scattering detector and a viscometer. Three Agilent PLgel 10 μm Mixed-B LS columns are used to provide polymer separation. Aldrich reagent grade 1,2,4-trichlorobenzene (TCB) with 300 ppm antioxidant butylated hydroxytoluene (BHT) is used as the mobile phase. The TCB mixture is filtered through a 0.1 m Teflon filter and degassed with an online degasser before entering the GPC instrument. The nominal flow rate is 1.0 mL/min and the nominal injection volume is 200 μL. The whole system including transfer lines, columns, detectors are contained in an oven maintained at 145° C. Given amount of polymer sample is weighed and sealed in a standard vial with 80 μL flow marker (Heptane) added to it. After loading the vial in the autosampler, polymer is automatically dissolved in the instrument with 8 mL added TCB solvent. The polymer is dissolved at 160° C. with continuous shaking for about 1 hour for most PE samples or 2 hour for PP samples. The TCB densities used in concentration calculation are 1.463 g/ml at room temperature and 1.284 g/ml at 145° C. The sample solution concentration is from 0.2 to 2.0 mg/ml, with lower concentrations being used for higher molecular weight samples.

The concentration (c), at each point in the chromatogram is calculated from the baseline-subtracted IR5 broadband signal intensity (I), using the following equation:

$$c \leq \beta I$$

where β is the mass constant determined with PE or PP standards. The mass recovery is calculated from the ratio of the integrated area of the concentration chromatography over elution volume and the injection mass which is equal to the pre-determined concentration multiplied by injection loop volume.

The conventional molecular weight (IR MW) is determined by combining universal calibration relationship with the column calibration which is performed with a series of monodispersed polystyrene (PS) standards ranging from 700 to 10M. The MW at each elution volume is calculated with following equation;

$$\log M = \frac{\log(K_{PS}/K)}{a+1} + \frac{a_{PS}+1}{a+1}\log M_{PS}$$

where the variables with subscript "PS" stands for polystyrene while those without a subscript are for the test samples. In this method, $a_{PS}$=0.67 and $K_{PS}$=0.000175 while a and K are calculated as described in the published in literature (Sun, T. et al. (2001) "Effect of Short Chain Branching on the Coil Dimensions of Polyolefins in Dilute Solutions," *Macromolecules*, v.34(19), pp. 6812-6820), except that for purposes of this invention and claims thereto, α=0.695 and K=0.000579 for linear ethylene polymers, α=0.705 and K=0.0002288 for linear propylene polymers, α=0.695+(0.01*(wt. fraction propylene)) and K=0.000579−(0.0003502*(wt. fraction propylene)) for ethylene-propylene copolymers. Concentrations are expressed in g/cm$^3$, molecular weight is expressed in g/mole, and intrinsic viscosity (hence K in the Mark-Houwink equation) is expressed in dL/g unless otherwise noted.

The comonomer composition is determined by the ratio of the IR5 detector intensity corresponding to $CH_2$ and $CH_3$ channel calibrated with a series of PE and PP homo/copolymer standards whose nominal value are predetermined by NMR or FTIR such as EMCC commercial grades about LLDPE, Vistamaxx, ICP, etc.

The LS detector is the 18-angle Wyatt Technology High Temperature DAWN HELEOSII. The LS molecular weight (M) at each point in the chromatogram is determined by analyzing the LS output using the Zimm model for static light scattering (M. B. Huglin, *Light Scattering from Polymer Solutions*, Academic Press, 1971):

$$\frac{K_o c}{\Delta R(\theta)} = \frac{1}{MP(\theta)} + 2A_2 c$$

Here, ΔR(θ) is the measured excess Rayleigh scattering intensity at scattering angle θ, c is the polymer concentration determined from the IR5 analysis, $A_2$ is the second virial coefficient. P(θ) is the form factor for a monodisperse random coil, and $K_o$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system. The refractive index, n=1.500 for TCB at 145° C. and λ=665 nm.

A high temperature Agilent (or Viscotek Corporation) viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$[\eta] = \eta_s / c$$

where c is concentration and was determined from the IR5 broadband channel output. The viscosity MW at each point is calculated from the below equation:

$$M = K_{PS} M^{\alpha_{PS}+1} / [\eta].$$

The branching index ($g'_{vis}$) is calculated using the output of the GPC-IR5-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits. The branching index $g'_{vis}$ is defined as:

$$g'_{vis} = \frac{[\eta]_{avg}}{kM_v^\alpha}$$

$M_V$ is the viscosity-average molecular weight based on molecular weights determined by LS analysis. The K/a are for the reference linear polymers are as described above.

All the concentration is expressed in g/cm$^3$, molecular weight is expressed in g/mole, and intrinsic viscosity is expressed in dL/g unless otherwise noted.

All molecular weights are reported in g/mol unless otherwise noted.

Differential Scanning Calorimetry (DSC—Procedure-2). Melting Temperature, Tm, is measured by differential scanning calorimetry ("DSC") using a DSCQ200 unit. The sample is first equilibrated at 25° C. and subsequently heated to 220° C. using a heating rate of 10° C./min (first heat). The sample is held at 220° C. for 3 minutes. The sample is subsequently cooled down to −100° C. with a constant cooling rate of 10° C./min (first cool). The sample is equilibrated at −100° C. before being heated to 220° C. at a constant heating rate of 10° C./min (second heat). The exothermic peak of crystallization (first cool) is analyzed using the TA Universal Analysis software and the corresponding to 10° C./min cooling rate is determined. The endothermic peak of melting (second heat) is also analyzed using the TA Universal Analysis software and the peak melting temperature (Tm) corresponding to 10° C./min heating rate is determined. In the event of conflict between the DSC Procedure-1 and DSC procedure-2, DSC procedure-2 is used.

Blends

In another embodiment, the polymer (such as the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, low density polyethylene (LDPE), linear low density polyethylene (LLDPE), high density polyethylene (HDPE), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In at least one embodiment, the polymer (such as polyethylene or polypropylene) is present in the above blends, at from 10 to 99 wt %, based upon the weight of the polymers in the blend, such as 20 to 95 wt %, such as at least 30 to 90 wt %, such as at least 40 to 90 wt %, such as at least 50 to 90 wt %, such as at least 60 to 90 wt %, such as at least 70 to 90 wt %.

The blends described above may be produced by mixing the polymers of the present disclosure with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; and talc.

Films

One or more of the foregoing polymers, such as the foregoing polyethylenes, polypropylenes, or blends thereof, may be used in a variety of end-use applications. Such applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble process and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, such as between 5 and 7, and in the Transverse Direction (TD) at a ratio of up to 15, such as 7 to 9. However, in at least one embodiment the film is oriented to the same extent in both the MD and TD directions.

The films may vary in thickness depending on the intended application; however, films of a thickness from 1 m to 50 m are usually suitable. Films intended for packaging are usually from 10 m to 50 m thick. The thickness of the sealing layer is typically 0.2 m to 50 m. There may be a sealing layer on both the inner and outer surfaces of the film or the sealing layer may be present on only the inner or the outer surface.

In at least one embodiment, one or more layers may be modified by corona treatment, electron beam irradiation, gamma irradiation, flame treatment, or microwave. In at least one embodiment, one or both of the surface layers is modified by corona treatment.

Overall, activators, catalyst systems, and methods of the present disclosure can provide improved solubility in aliphatic solvents, as compared to conventional activator compounds and catalyst systems. Activators, catalyst systems, and methods of the present disclosure can provide polyolefins having a weight average molecular weight (Mw) of about 25,000 to about 2,500,000 g/mol and a melt temperature (Tm) of about 100° C. or greater.

EXAMPLES EMBODIMENTS

Embodiments disclosed herein include:

A. Compounds represented by Formula (I):

$$[Ar(EHR^1R^2)(OR^3)]_d^+[M^{k+}Q_n]^{d-} \quad (I)$$

wherein:

Ar is an aryl group;

E is nitrogen or phosphorous;

$R^1$ is a $C_1$-$C_{30}$, optionally substituted, linear alkyl group;

$R^2$ is a $C_1$-$C_{30}$, optionally substituted, linear alkyl group;

$R^3$ is a $C_{10}$-$C_{30}$, optionally substituted, linear alkyl group;

M is an element selected from group 13 of the Periodic Table of the Elements;

d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Embodiment A may have one or more of the following additional elements in any combination:

Element 1: wherein $R^1$ is a $C_1$ to $C_{10}$ linear alkyl group.

Element 2: wherein $R^1$ is methyl, ethyl, propyl, butyl, pentyl, or hexyl.

Element 3: wherein $R^2$ is a $C_1$-$C_{20}$, optionally substituted, linear alkyl group.

Element 4: wherein $R^3$ is a $C_{10}$-$C_{20}$, optionally substituted, linear alkyl group.

Element 5: wherein $R^1$ is methyl.

Element 6: wherein $R^2$ is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

Element 7: wherein $R^3$ is n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

Element 8: wherein E is nitrogen.

Element 9: wherein M is boron and k is 3.

Element 10: wherein M is boron and E is nitrogen.

Element 11: wherein Q is an optionally substituted aryl group.

Element 12: wherein Q is a halogen substituted aryl group.

Element 13: wherein Q is a perfluoroaryl group.

Element 14: wherein Q is a perflurophenyl group.

Element 15: wherein Q is a perfluoronaphthyl group.

Element 16: wherein $R^1$, $R^2$, and $R^3$ together comprise 20 or more carbon atoms.

Element 17: wherein Ar is a phenyl group.

Illustrative combinations applicable to A include, but are not limited to, 1 or 5 and 3; 1 or 5 and 4; 5, 6, and 7; 1 or 5 and 3, 8, or 10; 8 and 9; 5-7 and 10; and 5-7, 10 and 12, 13, 14 or 15.

B. Compounds represented by Formula (II):

$$[Cat]^+[MQ_4]^- \quad (II)$$

wherein:

M is an element selected from group 13 of the Periodic Table of the Elements;

Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical; and $[Cat]^+$ is a cation represented by a structure selected from the group consisting of

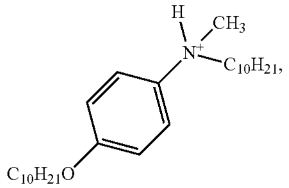

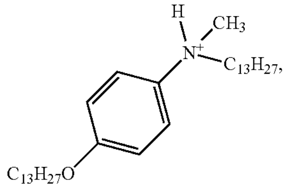

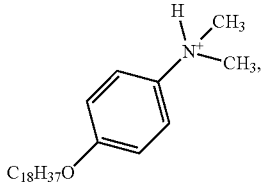

and

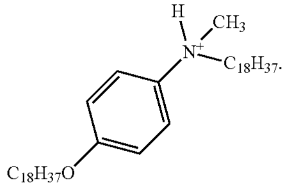

Embodiment B may have one or more of the following additional elements in any combination:

Element 18: wherein Q is an optionally substituted aryl group.

Element 19: wherein Q is a halogen substituted aryl group.

Element 20: wherein Q is a perfluoroaryl group.

Element 21: wherein Q is a perfluophenyl group.

Element 22: wherein Q is a perfluoronaphthyl group.

Element 23: wherein M is boron.

Illustrative combinations applicable to B include, but are not limited to, 18 and 23; 19 and 23; 20 and 23; 21 and 23; and 22 and 23.

C. Compounds represented by Formula (III):

$$[R^{11}R^{12}R^{13}EH]^+[BR^{14}R^{15}R^{16}R^{17}]^- \quad (III)$$

wherein:

E is nitrogen or phosphorous;

each of $R^{11}$, $R^{12}$, and $R^{13}$ is independently a $C_1$-$C_{30}$ linear alkyl group or an aryl group, wherein the aryl group is substituted with at least one $C_{10}$-$C_{30}$ alkoxy group, wherein $R^{11}$, $R^{12}$, and $R^{13}$ together comprise 26 or more carbon atoms; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

Embodiment C may have one or more of the following additional elements in any combination:

Element 24: wherein each of $R^{11}$ and $R^{12}$ is independently a $C_1$-$C_{30}$ linear alkyl, and $R^{13}$ is an aryl group substituted with a $C_{10}$-$C_{30}$ alkoxy group.

Element 25: wherein $R^{11}$, $R^{12}$ and $R^{13}$ together comprise 30 or more carbon atoms.

Element 26: wherein $R^{11}$, $R^{12}$, and $R^{13}$ together comprise 40 or more carbon atoms.

Element 27: wherein E is nitrogen.

Illustrative combinations applicable to C include, but are not limited to, 24 and 25 or 26; 24 and 27; and 25 or 26 and 27.

Each of embodiments A, B, and C in combination with one or more of Elements 1-17, Elements 18-23, or Elements 24-27, respectively, may have one or more of the following additional elements in any combination:

Element 28: wherein the compound has a solubility of at least 10 mM at 25° C. in methylcyclohexane.

Element 29: wherein the compound has a solubility of at least 10 mM at 25° C. in isohexane.

Element 30: wherein the compound has a solubility of at least 10 mM at 25° C. in methylcyclohexane and a solubility of at least 10 mM at 25° C. in isohexane.

Embodiment D: a catalyst system comprising a catalyst and an activator comprising the compound of embodiments A, B, and C in combination with one or more of Elements 1-17, Elements 18-23, or Elements 24-27, respectively, and one or more of Elements 28-30.

Embodiment D may have one or more of the following additional elements in any combination:

Element 31: further comprising a support material.

Element 32: wherein the support material is selected from $Al_2O_3$, $ZrO_2$, $SiO_2$, $SiO_2/Al_2O_3$, $SiO_2/TiO_2$, silica clay, silicon oxide/clay, and mixtures thereof.

Element 33: wherein the catalyst is represented by Formula (IV):

(IV)

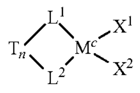

wherein in Formula (IV):

$M^c$ is an element selected from group 4 of the Periodic Table of the Elements;

n is 0 or 1;

T is an optional bridging group selected from S, O, PR', NR', SiR"$_2$, $CH_2$, CHR", or CR"$_2$, wherein R' is a $C_1$-$C_{30}$, optionally substituted, hydrocarbyl group and R" is hydrogen or a $C_1$-$C_{30}$, optionally substituted, hydrocarbyl group;

$L^1$ and $L^2$ are independently cyclopentadienyl, substituted cyclopentadienyl, indenyl, substituted indenyl, tetrahydroindenyl, substituted tetrahydroindenyl, fluorenyl, or substituted fluorenyl groups; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Element 34: wherein T is an optional bridging group selected from dialkylsilyl, diarylsilyl, dialkylmethyl, diarylmethyl, ethylenyl, or hydrocarbylethylenyl wherein one, two, three or four of the hydrogen atoms in ethylenyl are substituted by hydrocarbyl.

Element 35: wherein the catalyst is $C_2$ symmetrical.

Element 36: wherein the catalyst is one or more of:

dimethylsilyl bis(indenyl)$M^c(R)_2$;

dimethylsilyl bis(tetrahydroindenyl)$M^c(R)_2$;

bis(1-methyl, 3-n-butyl cyclopentadienyl)$M^c(R)_2$;

bis(indenyl)$M^c(R)_2$;

dimethylsilyl bis(tetrahydroindenyl)$M^c(R)_2$;

bis(n-propylcyclopentadienyl)$M^c(R)_2$;

dimethylsilyl (tetramethylcyclopentadienyl)(cyclododecylamido)$M^c(R)_2$;

dimethylsilyl (tetramethylcyclopentadienyl)(cyclododecylamido)$M^c(R)_2$;

dimethylsilyl (tetramethylcyclopentadienyl)(t-butylamido) $M^c(R)_2$;

dimethylsilyl (tetramethylcyclopentadienyl)(t-butylamido) $M^c(R)_2$;

1,1'-bis(4-triethylsilylphenyl)(methylene)(cyclopentadienyl)(fluorenyl)$M^c(R)_2$;

μ-$(CH_3)_2$Si(cyclopentadienyl)(1-adamantylamido)$M^c(R)_2$;

μ-$(CH_3)_2$Si(3-tertbutylcyclopentadienyl)(1-adamantylamido)$M^c(R)_2$;

μ-$(CH_3)_2$(tetramethylcyclopentadienyl)(1-adamantylamido) $M^c(R)_2$;

μ-$(CH_3)_2$Si(tetramethylcyclopentadienyl)(1-adamantylamido)$M^c(R)_2$;

μ-$(CH_3)_2$C(tetramethylcyclopentadienyl)(1-adamantylamido)$M^c(R)_2$;

μ-$(CH_3)_2$Si(tetramethylcyclopentadienyl)(1-tertbutylamido) $M^c(R)_2$;

μ-$(CH_3)_2$Si(fluorenyl)(1-tertbutylamido)$M^c(R)_2$;

μ-$(CH_3)_2$Si(tetramethylcyclopentadienyl)(1-cyclododecylamido)$M^c(R)_2$;

μ-$(C_6H_5)_2$C(tetramethylcyclopentadienyl)(1-cyclododecylamido)$M^c(R)_2$;

μ-$(CH_3)_2$Si($\eta^5$-2,6,6-trimethyl-1,5,6,7-tetrahydro-s-indacen-1-yl)(tertbutylamido)$M^c(R)_2$;

where $M^c$ is selected from Ti, Zr, and Hf; and R is selected from halogen or $C_1$ to $C_5$ alkyl.

Element 37: wherein the catalyst is rac-dimethylsilyl-bis (indenyl)hafnium dimethyl.

Element 38: wherein the catalyst is represented by Formula (CAT-2):

(CAT-2)

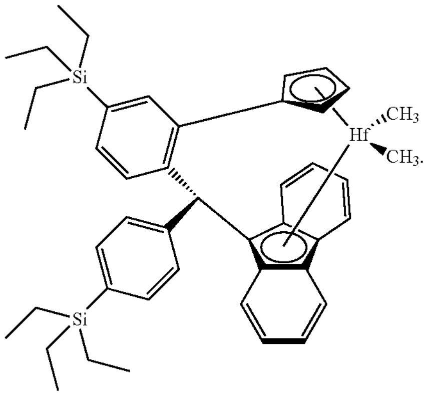

Element 39: wherein the catalyst is represented by Formula (CAT-3):

(CAT-3)

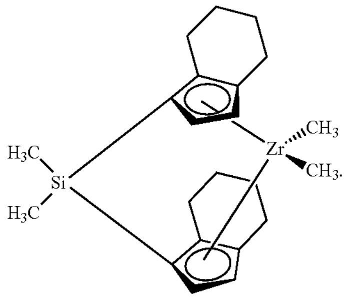

Element 40: wherein the catalyst is represented by Formula (CAT-4):

(CAT-4)

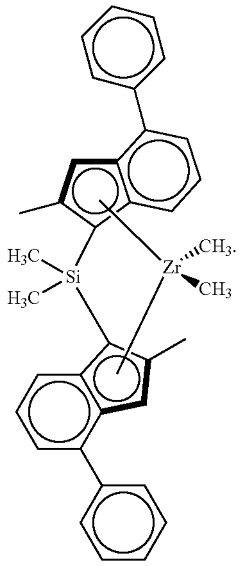

Element 41: wherein the catalyst is represented by Formula (V):

(V)

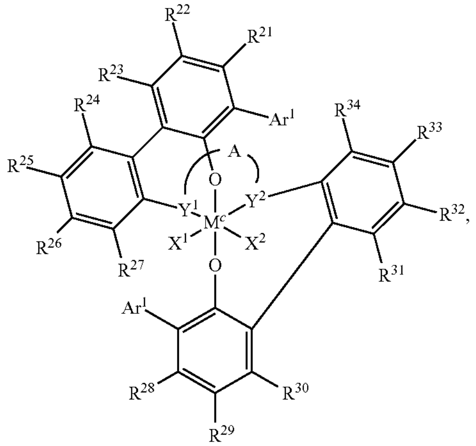

wherein in Formula (V):

$M^c$ is an element selected from group 4 of the Periodic Table of the Elements, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ are independently hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring:

A is a $C_1$-$C_{50}$ alkyl group;

$Y^1$ and $Y^2$ are independently selected from O, S, $NR^a$ and $PR^a$ herein $R^a$ is optionally substituted hydrocarbyl;

$Ar^1$ is phenyl, naphthyl, biphenyl, anthracenyl, or phenanthrenyl; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, alkylaryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Element 42: wherein $M^c$ is Zr.

Element 43: wherein $Y^1$ and $Y^2$ are O.

Element 44: wherein $X^1$ and $X^2$ are benzyl.

Element 45: wherein A is propyl or butyl.

Element 46: wherein the catalyst is represented by Formula (CAT-5):

(CAT-5)

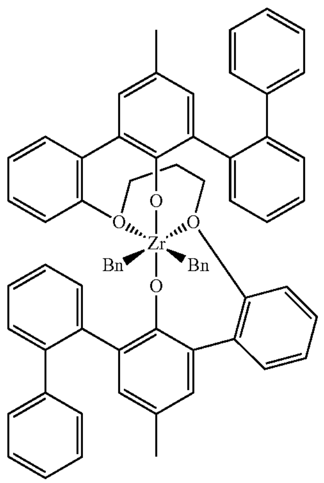

Element 47: wherein the catalyst is represented by Formula (CAT-6):

(CAT-6)

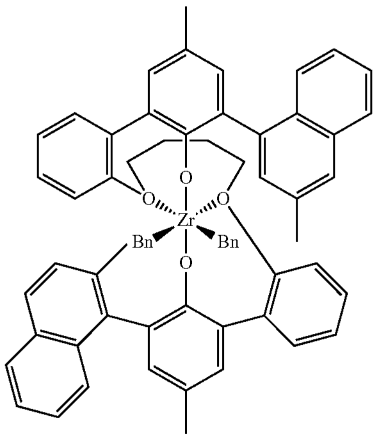

Element 48: wherein the catalyst is represented by Formulas (VIa) or (VIb):

(VIa)

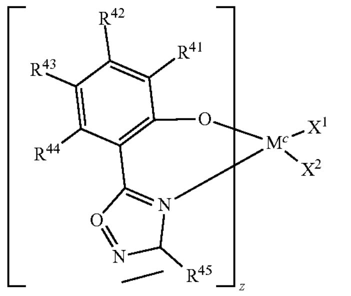

-continued (VIb)

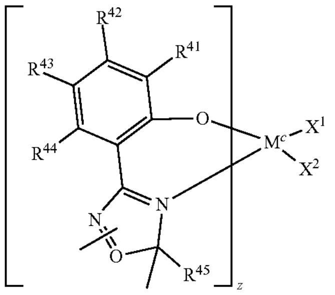

wherein in Formulas (VIa) or (VIb):

$M^c$ is an element selected from group 4 of the Periodic Table of the Elements $R^{41}$, $R^{42}$, $R^{43}$, $R^{44}$, $R^{45}$ are independently selected from the group consisting of hydrogen, alkyl, substituted alkyl, cycloalkyl, substituted cycloalkyl heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand; and z is 1, 2, 3, or 4.

Element 49: wherein $M^c$ is Zr.

Element 50: wherein $X^1$ and $X^2$ are benzyl.

Element 51: wherein the catalyst is represented by Formula (CAT-7):

(CAT-7)

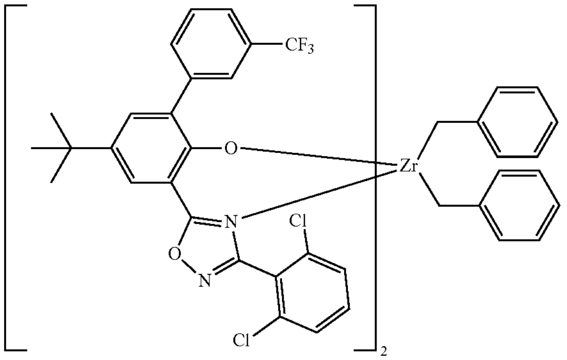

Element 52: wherein the catalyst is represented by Formula (VII):

(VII)

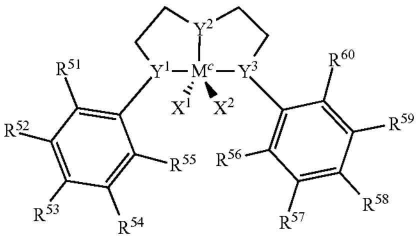

wherein in Formula (VII):

$M^c$ is an element selected from group 4 of the Periodic Table of the Elements $R^{51}$, $R^{52}$, $R^{53}$, $R^{54}$, $R^{55}$, $R^{56}$, $R^{57}$, $R^{58}$, $R^{59}$, $R^{60}$ are independently selected from the group consisting of hydrogen, alkyl, substituted alkyl, cycloalkyl, substituted, cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$Y^1$ and $Y^2$ are independently O, N, NH, or S; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

Element 53: wherein the catalyst is represented by Formula (CAT-8):

(CAT-8)

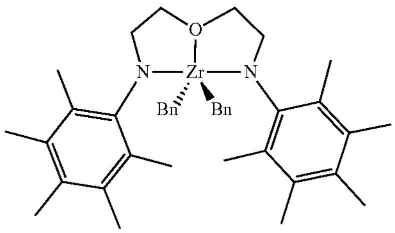

Element 54: wherein the catalyst is represented by Formula (CAT-9):

(CAT-9)

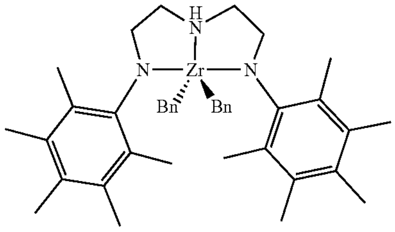

Illustrative combinations applicable to D include, but are not limited to, 31 and 33; 31 and 36; 31 and 38; 31 and 39; 31 and 40; 31 and 41; 31 and 46; 31 and 47; 31 and 48; 31 and 51; 31 and 52; and 31 and 53.

E: a method comprising contacting at least one olefin with a catalyst system of Embodiment D in combination with one or more of Elements 31-54, and obtaining a polyolefin.

Embodiment E may have one or more of the following additional elements in any combination:

Element 55: wherein the at least one olefin comprises propylene.

Element 56: wherein the polyolefin has an Mw of about 25,000 to about 300,000 g/mol and a melt temperature of about 100° C. to about 130° C.

Element 57: wherein the at least one olefin comprises ethylene.

Element 58: wherein the polyolefin has an Mw of about 250,000 to about 2,500,000 g/mol and a melt temperature of about 120° C. to about 140° C.

Illustrative combinations applicable to E include, but are not limited to, 55 and 56; and 57 and 58.

F: a method comprising contacting two or more different olefins with a catalyst system of Embodiment D in combination with one or more of Elements 31-54, and obtaining a polyolefin.

Embodiment F may have one or more of the following additional elements in any combination:

Element 59: wherein the two or more olefins are ethylene and octene.

Element 60: wherein the polyolefin has an Mw of from about 50,000 to about 1,500,000 g/mol and a melt temperature of from about 25° C. to about 100° C.

Embodiments E and F may have one or more of the following additional element:

Element 61: wherein contacting is performed in the gas phase or slurry phase.

G: a solution comprising a compound of any one of Embodiments A, B, or C, in combination with one or more of Elements 1-17, Elements 18-23, or Elements 24-27, and an aliphatic solvent; wherein aromatic solvents are absent.

H: a solution comprising a catalyst system of Embodiment D in combination with one or more of Elements 31-54 and an aliphatic solvent; wherein aromatic solvents are absent.

The present disclosure also relates to

1. A compound represented by Formula (I):

$$[Ar(EHR^1R^2)(OR^3)]_d^+[M^{k+}Q_n]^- \quad (I)$$

wherein:

Ar is an aryl group;

E is nitrogen or phosphorous;

$R^1$ is a $C_1$-$C_{30}$, optionally substituted, linear alkyl group;

$R^2$ is a $C_1$-$C_{30}$, optionally substituted, linear alkyl group;

$R^3$ is a $C_{10}$-$C_{30}$, optionally substituted, linear alkyl group;

M is an element selected from group 13 of the Periodic Table of the Elements;

d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

2. The compound of paragraph 1, wherein $R^1$ is a $C_1$ to $C_{10}$ linear alkyl group.

3. The compound of any of paragraph 1 or paragraph 2, wherein $R^1$ is methyl, ethyl, propyl, butyl, pentyl, or hexyl.
4. The compound of any one of paragraphs 1-3, wherein $R^2$ is a $C_1$-$C_{20}$, optionally substituted, linear alkyl group.
5. The compound of any one of paragraphs 1-4, wherein $R^3$ is a $C_{10}$-$C_{20}$, optionally substituted, linear alkyl group.
6. The compound of any one of paragraphs 1-5, wherein $R^1$ is methyl.
7. The compound of any one of paragraphs 1-6, wherein $R^2$ is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.
8. The compound of any one of paragraphs 1-7, wherein $R^3$ is n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.
9. The compound of any one of paragraphs 1-8, wherein E is nitrogen.
10. The compound of any one of paragraphs 1-9, wherein M is boron and k is 3.
11. The compound of any one of paragraphs 1-10, wherein M is boron and E is nitrogen.
12. The compound of any one of paragraphs 1-11, wherein Q is an optionally substituted aryl group.
13. The compound of any one of paragraphs 1-12, wherein Q is a halogen substituted aryl group.
14. The compound of any one of paragraphs 1-13, wherein Q is a perfluoroaryl group.
15. The compound of any one of paragraphs 1-14, wherein Q is a perflurophenyl group.
16. The compound of any one of paragraphs 1-14, wherein Q is a perfluoronaphthyl group.
17. The compound of any one of paragraphs 1-16, wherein $R^1$, $R^2$, and $R^3$ together comprise 20 or more carbon atoms.
18. The compound of any one of paragraphs 1-16, wherein Ar is a phenyl group.
19. A compound represented by Formula (II):

$$[Cat]^+[MQ_4]^- \quad (II)$$

wherein:

M is an element selected from group 13 of the Periodic Table of the Elements;

Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical; and $[Cat]^+$ is a cation represented by a structure selected from the group consisting of

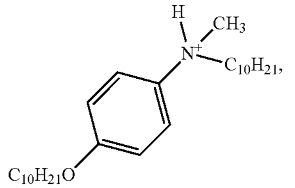

-continued

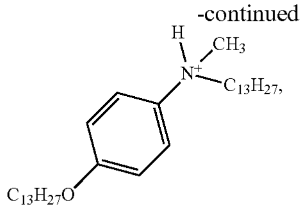

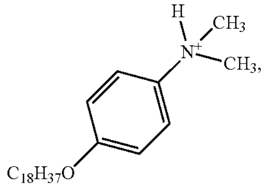
and

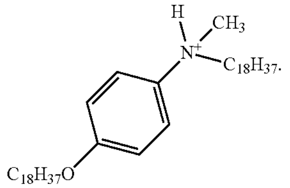

20. The compound of paragraph 19, wherein Q is an optionally substituted aryl group.
21. The compound of any one of paragraphs 19-20, wherein Q is a halogen substituted aryl group.
22. The compound of any one of paragraphs 19-21, wherein Q is a perfluoroaryl group.
23. The compound of any one of paragraphs 19-22, wherein Q is a perflurophenyl group.
24. The compound of any one of paragraphs 19-22, wherein Q is a perfluoronaphthyl group.
25. The compound of any one of paragraphs 19-24, wherein M is boron.
26. A compound represented by Formula (III):

$$[R^{11}R^{12}R^{13}EH]^+[BR^{14}R^{15}R^{16}R^{17}]^- \quad (III)$$

wherein:

E is nitrogen or phosphorous;

each of $R^{11}$, $R^{12}$, and $R^{13}$ is independently a $C_1$-$C_{30}$ linear alkyl group or an aryl group, wherein the aryl group is substituted with at least one $C_{10}$-$C_{30}$ alkoxy group, wherein $R^{11}$, $R^{12}$, and $R^{13}$ together comprise 26 or more carbon atoms; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

27. The compound of paragraph 26, wherein each of $R^{11}$ and $R^{12}$ is independently a $C_1$-$C_{30}$ linear alkyl, and $R^{13}$ is an aryl group substituted with a $C_{10}$-$C_{30}$ alkoxy group.
28. The compound of any one of paragraphs 26-27, wherein $R^{11}$, $R^{12}$, and $R^{13}$ together comprise 30 or more carbon atoms.
29. The compound of any one of paragraphs 26-28, wherein $R^{11}$, $R^{12}$, and $R^{13}$ together comprise 40 or more carbon atoms.
30. The compound of any one of paragraphs 26-29, wherein E is nitrogen.
31. The compound of any one of paragraphs 1-30, wherein the compound has a solubility of at least 10 mM at 25° C. in methylcyclohexane.
32. The compound of any one of paragraphs 1-30, wherein the compound has a solubility of at least 10 mM at 25° C. in isohexane.

33. The compound of any one of paragraphs 1-30, wherein the compound has a solubility of at least 10 mM at 25° C. in methylcyclohexane and a solubility of at least 10 mM at 25° C. in isohexane.
34. A catalyst system comprising a catalyst and an activator comprising the compound of any one of paragraphs 1-33.
35. The catalyst system of paragraph 34, further comprising a support material.
36. The catalyst system of paragraph 35, wherein the support material is selected from $Al_2O_3$, $ZrO_2$, $SiO_2$, $SiO_2/Al_2O_3$, $SiO_2/TiO_2$, silica clay, silicon oxide/clay, and mixtures thereof.
37. The catalyst system of any one of paragraphs 34-36, wherein the catalyst is represented by Formula (IV):

(IV)

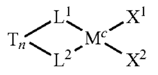

wherein in Formula (IV):
$M^c$ is an element selected from group 4 of the Periodic Table of the Elements:
n is 0 or 1:
T is an optional bridging group selected from S, O, PR', NR', SiR"$_2$, $CH_2$, CHR", or CR"$_2$, wherein R' is a $C_1$-$C_{30}$, optionally substituted, hydrocarbyl group and R" is hydrogen or a $C_1$-$C_{30}$, optionally substituted, hydrocarbyl group;
$L^1$ and $L^2$ are independently cyclopentadienyl, substituted cyclopentadienyl, indenyl, substituted indenyl, tetrahydroindenyl, substituted tetrahydroindenyl, fluorenyl, or substituted fluorenyl groups; and
$X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.
38. The catalyst system of paragraph 37, wherein T is an optional bridging group selected from dialkylsilyl, diarylsilyl, dialkylmethyl, diarylmethyl, ethylenyl, or hydrocarbylethylenyl wherein one, two, three or four of the hydrogen atoms in ethylenyl are substituted by hydrocarbyl.
39. The catalyst system of paragraph 37, wherein the catalyst is $C_2$ symmetrical.
40. The catalyst system of paragraph 37, wherein the catalyst is one or more of:
dimethylsilyl bis(indenyl)$M^c(R)_2$;
dimethylsilyl bis(tetrahydroindenyl)$M^c(R)_2$;
bis(1-methyl, 3-n-butyl cyclopentadienyl)$M^c(R)_2$;
bis(indenyl)$M^c(R)_2$;
dimethylsilyl bis(tetrahydroindenyl)$M^c(R)_2$;
bis(n-propylcyclopentadienyl)$M^c(R)_2$;
dimethylsilyl (tetramethylcyclopentadienyl)(cyclododecylamido)$M^c(R)_2$;
dimethylsilyl (tetramethylcyclopentadienyl)(cyclododecylamido)$M^c(R)_2$;
dimethylsilyl (tetramethylcyclopentadienyl)(t-butylamido) $M^c(R)_2$;
dimethylsilyl (tetramethylcyclopentadienyl)(t-butylamido) $M^c(R)_2$;
1,1'-bis(4-triethylsilylphenyl)(methylene)(cyclopentadienyl)(fluorenyl)$M^c(R)_2$;
μ-$(CH_3)_2$Si(cyclopentadienyl)(1-adamantylamido)$M^c(R)_2$;
μ-$(CH_3)_2$Si(3-tertbutylcyclopentadienyl)(1-adamantylamido)$M^c(R)_2$;
μ-$(CH_3)_2$(tetramethylcyclopentadienyl)(1-adamantylamido) $M^c(R)_2$;
μ-$(CH_3)_2$Si(tetramethylcyclopentadienyl)(1-adamantylamido)$M^c(R)_2$;
μ-$(CH_3)_2$C(tetramethylcyclopentadienyl)(1-adamantylamido)$M^c(R)_2$;
μ-$(CH_3)_2$Si(tetramethylcyclopentadienyl)(1-tertbutylamido) $M^c(R)_2$;
μ-$(CH_3)_2$Si(fluorenyl)(1-tertbutylamido)$M^c(R)_2$;
μ-$(CH_3)_2$Si(tetramethylcyclopentadienyl)(1-cyclododecylamido)$M^c(R)_2$;
μ-$(C_6H_5)_2$C(tetramethylcyclopentadienyl)(1-cyclododecylamido)$M^c(R)_2$;
μ-$(CH_3)_2$Si($\eta^5$-2,6,6-trimethyl-1,5,6,7-tetrahydro-s-indacen-1-yl)(tertbutylamido)$M^c(R)_2$; where $M^c$ is selected from Ti, Zr, and Hf; and R is selected from halogen or $C_1$ to $C_5$ alkyl.
41. The catalyst system of any of paragraphs 37-40, wherein the catalyst is rac-dimethylsilyl-bis(indenyl) hafnium dimethyl.
42. The catalyst system of paragraph 37, wherein the catalyst is represented by Formula (CAT-2):

(CAT-2)

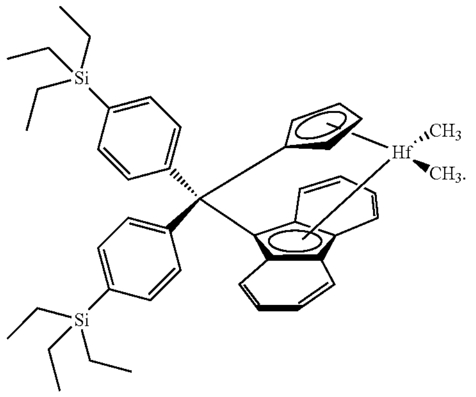

43. The catalyst system of paragraph 37, wherein the catalyst is represented by Formula (CAT-3):

(CAT-3)

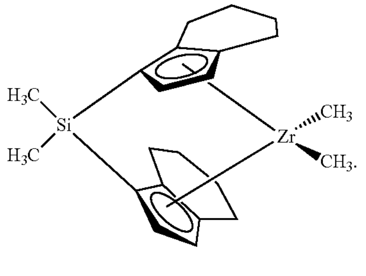

44. The catalyst system of paragraph 37, wherein the catalyst is represented by Formula (CAT-4):

(CAT-4)

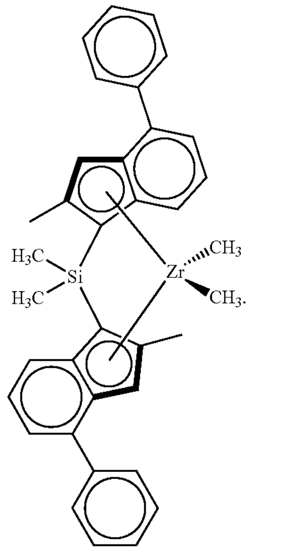

45. The catalyst system of paragraph 37, wherein the catalyst is represented by Formula (V):

(V)

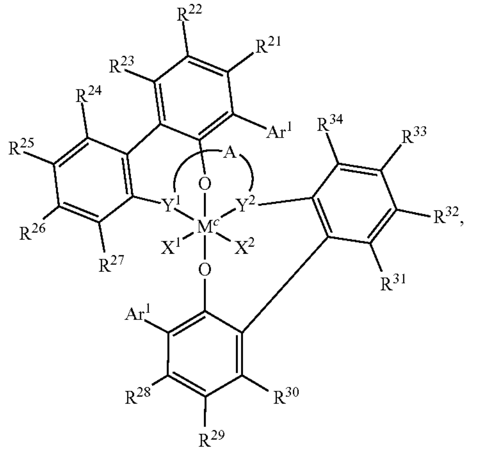

wherein in Formula (V):

$M^c$ is an element selected from group 4 of the Periodic Table of the Elements;

$R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ are independently hydride, halide, optionally substituted hydrocarbyl, heteroatom-containing optionally substituted hydrocarbyl, alkoxy, aryloxy, silyl, boryl, dialkyl amino, alkylthio, arylthio and seleno: optionally two or more R groups can combine together into ring structures with such ring structures having from 3 to 100 non-hydrogen atoms in the ring:

A is a $C_1$-$C_{50}$ alkyl group;

$Y^1$ and $Y^2$ are independently selected from O, S, $NR^a$ and $PR^a$ wherein $R^a$ is optionally substituted hydrocarbyl;

$Ar^1$ is phenyl, naphthyl, biphenyl, anthracenyl, or phenanthrenyl; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, alkylaryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

46. The catalyst system of paragraph 45, wherein $M^c$ is Zr.

47. The catalyst system of any one of paragraphs 45-46, wherein $Y^1$ and $Y^2$ are O.

48. The catalyst system of any one of paragraphs 45-47, wherein $X^1$ and $X^2$ are benzyl.

49. The catalyst system of any one of paragraphs 45-48, wherein A is propyl or butyl.

50. The catalyst system of any one of paragraphs 45-49, wherein the catalyst is represented by Formula (CAT-5):

(CAT-5)

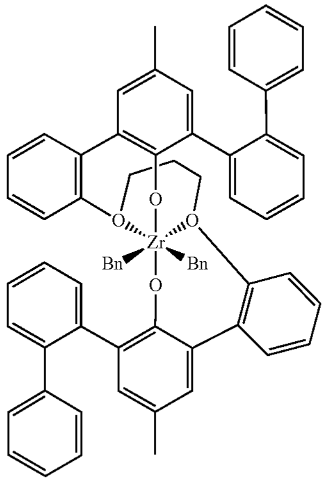

51. The catalyst system of any one of paragraphs 45-49, wherein the catalyst is represented by Formula (CAT-6):

(CAT-6)

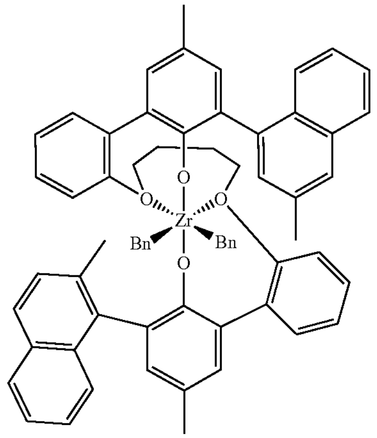

52. The catalyst system of any one of paragraphs 34-36, wherein the catalyst is represented by Formulas (VIa) or (VIb):

(VIa)

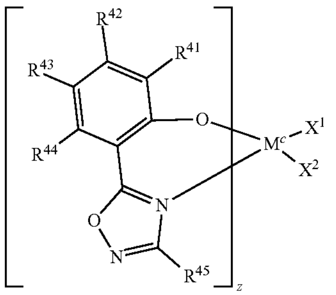

(VIb)

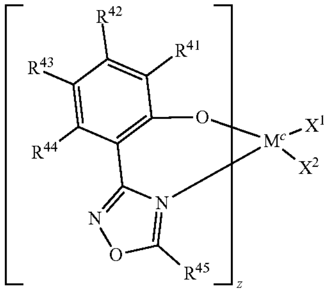

wherein in Formulas (VIa) or (VIb):

$M^c$ is an element selected from group 4 of the Periodic Table of the Elements $R^{41}$, $R^{42}$, $R^{43}$, $R^{44}$, $R^{45}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$X^3$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand: and z is 1, 2, 3, or 4.

53. The catalyst system of paragraph 52, wherein $M^c$ is Zr.

54. The catalyst system of any of paragraphs 52-53, wherein $X^1$ and $X^2$ are benzyl.

55. The catalyst system of any one of paragraphs 52-54, wherein the catalyst is represented by Formula (CAT-7):

(CAT-7)

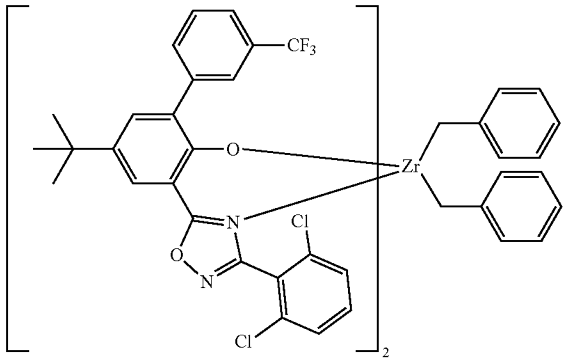

56. The catalyst system of any of paragraphs 34-36, wherein the catalyst is represented by Formula (VII):

(VII)

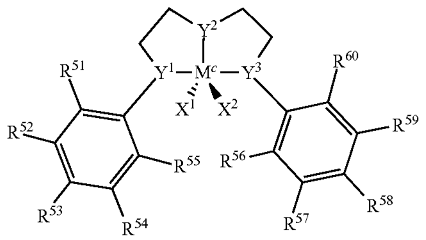

wherein in Formula (VII):

$M^c$ is an element selected from group 4 of the Periodic Table of the Elements $R^{51}$, $R^{52}$, $R^{53}$, $R^{54}$, $R^{55}$, $R^{56}$, $R^{57}$, $R^{58}$, $R^{59}$, $R^{60}$ are independency selected from the group consisting of hydrogen, alkyl, substituted alkyl, cycloalkyl, substituted, cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, $Y^1$ and $Y^2$ are independently O, N, NH, or S; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms: or both together can be an olefin, diolefin or aryne ligand.

57. The catalyst system of paragraph 56, wherein the catalyst is represented by Formula (CAT-8):

(CAT-8)

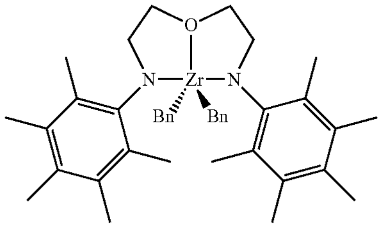

58. The catalyst system of paragraph 56, wherein the catalyst is represented by Formula (CAT-9):

(CAT-9)

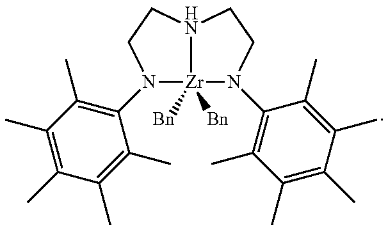

59. A method comprising contacting at least one olefin with the catalyst system of any one of paragraphs 34-58, and obtaining a polyolefin.

60. The method of paragraph 59, wherein the at least one olefin comprises propylene.

61. The method of paragraph 60, wherein the polyolefin has an Mw of about 25,000 to about 300,000 g/mol and a melt temperature of about 100° C. to about 130° C.

62. The method of paragraph 59, wherein the at least one olefin comprises ethylene.

63. The method of paragraph 62, wherein the polyolefin has an Mw of about 250,000 to about 2,500,000 g/mol and a melt temperature of about 120° C. to about 140° C.

64. A method comprising contacting two or more different olefins with the catalyst system of any one of paragraphs 34-58; and obtaining a polyolefin.

65. The method of paragraph 64, wherein the two or more olefins are ethylene and octene.

66. The method of paragraph 65, wherein the polyolefin has an Mw of from about 50,000 to about 1,500,000 g/mol and a melt temperature of from about 25° C. to about 100° C.

67. The method of any one of paragraphs 59-66, wherein contacting is performed in the gas phase or slurry phase.

68. A solution comprising the compound of any one of paragraphs 1-33 and an aliphatic solvent; wherein aromatic solvents are absent.

69. A solution comprising the catalyst system of any one of paragraphs 34-57 and an aliphatic solvent; wherein aromatic solvents are absent.

The present disclosure further relates to

1A. A compound represented by Formula (I):

$$[Ar(EHR^1R^2)(OR^3)]_d^+[M^{k+}Q_n]^{d-} \quad (I)$$

wherein:

Ar is an aryl group;

E is nitrogen or phosphorous;

$R^1$ is a $C_1$-$C_{30}$, optionally substituted, linear alkyl group;

$R^2$ is a $C_1$-$C_{30}$, optionally substituted, linear alkyl group;

$R^3$ is a $C_{10}$-$C_{30}$, optionally substituted, linear alkyl group;

M is an element selected from group 13 of the Periodic Table of the Elements;

d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

2A. The compound of paragraph 1A, wherein $R^1$ is a $C_1$ to $C_{10}$ linear alkyl group.

3A. The compound of paragraph 1A or paragraph 2A, wherein $R^1$ is methyl, ethyl, propyl, butyl, pentyl, or hexyl.

4A. The compound of paragraph 1A or paragraph 2A, wherein $R^2$ is a $C_1$-$C_{20}$, optionally substituted, linear alkyl group.

5A. The compound of paragraph 1A or paragraph 2A, wherein $R^3$ is a $C_{10}$-$C_{20}$, optionally substituted, linear alkyl group.

6A. The compound of paragraph 1A, wherein $R^1$ is methyl.

7A. The compound of paragraph 6A, wherein $R^2$ is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

8A. The compound of paragraph 7A, wherein $R^3$ is n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

9A. The compound of any one of paragraph 1A, 2A or 6A-8A, wherein E is nitrogen.

10A. The compound of any one of paragraph 1A, 2A or 6A-8A, wherein M is boron and k is 3.

11A. The compound of any one of paragraph 1A, 2A or 6A-8A, wherein M is boron and E is nitrogen.

12A. The compound of any one of paragraph 1A, 2A or 6A-8A, wherein Q is an optionally substituted aryl group.

13A. The compound of any one of paragraph 1A, 2A or 6A-8A, wherein Q is a halogen substituted aryl group.

14A. The compound of any one of paragraph 1A, 2A or 6A-8A, wherein Q is a perfluoroaryl group.

15A. The compound of any one of paragraph 1A, 2A or 6A-8A, wherein Q is a perflurophenyl group.

16A. The compound of any one of paragraph 1A, 2A or 6A-8A, wherein Q is a perfluoronaphthyl group.

17A. The compound of any one of paragraph 1A, 2A or 6A-8A, wherein $R^1$, $R^2$, and $R^3$ together comprise 20 or more carbon atoms.

18A. The compound of any one of paragraph 1A, 2A or 6A-8A, wherein Ar is a phenyl group.

19A. A compound represented by Formula (II):

$$[Cat]^+[MQ_4]^- \quad (II)$$

wherein:

M is an element selected from group 13 of the Periodic Table of the Elements;

Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical; and $[Cat]^+$ is a cation represented by a structure selected from the group consisting of

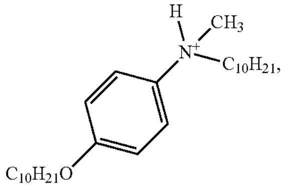

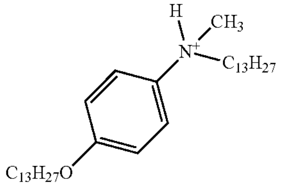

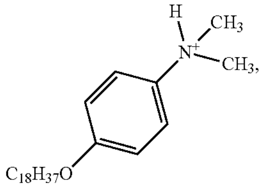

and

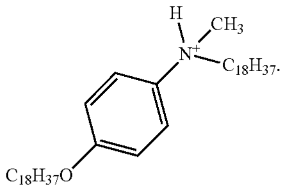

20A. The compound of paragraph 19A, wherein Q is an optionally substituted aryl group.

21A. The compound of paragraph 20A, wherein Q is a halogen substituted aryl group.

22A. The compound of any one of paragraphs 19A-21A, wherein Q is a perfluoroaryl group.

23A. The compound of any one of paragraphs 19A-21A, wherein Q is a perfluophenyl group.

24A. The compound of any one of paragraphs 19A-21A, wherein Q is a perfluoronaphthyl group.

25A. The compound of any one of paragraphs 19A-21A, wherein M is boron.

26A. A compound represented by Formula (III):

$$[R^{11}R^{12}R^{13}EH]^+[BR^{14}R^{15}R^{16}R^{17}]^- \quad (II)$$

wherein:

E is nitrogen or phosphorous;

each of $R^{11}$, $R^{12}$, and $R^{13}$ is independently a $C_1$-$C_{30}$ linear alkyl group or an aryl group, wherein the aryl group is substituted with at least one $C_{10}$-$C_{30}$ alkoxy group, wherein $R^{11}$, $R^{12}$, and $R^{13}$ together comprise 26 or more carbon atoms; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

27A. The compound of paragraph 26A, wherein each of $R^{11}$ and $R^{12}$ is independently a $C_1$-$C_{30}$ linear alkyl, and $R^{13}$ is an aryl group substituted with a $C_{10}$-$C_{30}$ alkoxy group.

28A. The compound of paragraph 27A, wherein $R^{11}$, $R^{12}$, and $R^{13}$ together comprise 30 or more carbon atoms.

29A. The compound of paragraph 27A, wherein $R^{11}$, $R^{12}$, and $R^{13}$ together comprise 40 or more carbon atoms.

30A. The compound of any one of paragraphs 26A-29A, wherein E is nitrogen.

31A. The compound of any one of paragraphs 1A, 2A, 6A-8A, or 19A-29A, wherein the compound has a solubility of at least 10 mM at 25° C. in methylcyclohexane.

32A. The compound of any one of paragraphs 1A, 2A, 6A-8A, or 19A-29A, wherein the compound has a solubility of at least 10 mM at 25° C. in isohexane.

33A. The compound of any one of paragraphs 1A, 2A, 6A-8A, or 19A-29A, wherein the compound has a solubility of at least 10 mM at 25° C. in methylcyclohexane and a solubility of at least 10 mM at 25° C. in isohexane.

34A. A catalyst system comprising a catalyst and an activator comprising the compound of any one of paragraphs any one of paragraphs 1A, 2A, 6A-8A, or 19A-29A.

35A. The catalyst system of paragraph 34A, further comprising a support material.

36A. The catalyst system of paragraph 35A, wherein the support material is selected from $Al_2O_3$, $ZrO_2$, $SiO_2$, $SiO_2/Al_2O_3$, $SiO_2/TiO_2$, silica clay, silicon oxide/clay, and mixtures thereof.

37A. The catalyst system of any one of paragraphs 34A-36A, wherein the catalyst is represented by Formula (IV):

(IV)

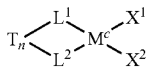

wherein in Formula (IV):

$M^c$ is an element selected from group 4 of the Periodic Table of the Elements;

n is 0 or 1;

T is an optional bridging group selected from S, O, PR', NR', $SiR''_2$, $CH_2$, CHR'', or $CR''_2$, wherein R' is a $C_1$-$C_{30}$, optionally substituted, hydrocarbyl group and R'' is hydrogen or a $C_1$-$C_{30}$, optionally substituted, hydrocarbyl group;

$L^1$ and $L^2$ are independently cyclopentadienyl, substituted cyclopentadienyl, indenyl, substituted indenyl, tetrahydroindenyl, substituted tetrahydroindenyl, fluorenyl, or substituted fluorenyl groups; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

38A. The catalyst system of paragraph 37A, wherein T is an optional bridging group selected from dialkylsilyl, diarylsilyl, dialkylmethyl, diarylmethyl, ethylenyl, or hydrocarbylethylenyl wherein one, two, three or four of the hydrogen atoms in ethylenyl are substituted by hydrocarbyl.

39A. The catalyst system of paragraph 37A, wherein the catalyst is $C_2$ symmetrical.

40A. The catalyst system of paragraph 37A, wherein the catalyst is one or more of:

dimethylsilyl bis(indenyl)$M^c(R)_2$;

dimethylsilyl bis(tetrahydroindenyl)$M^c(R)_2$;

bis(1-methyl, 3-n-butyl cyclopentadienyl)$M^c(R)_2$;

bis(indenyl)$M^c(R)_2$;

dimethylsilyl bis(tetrahydroindenyl)$M^c(R)_2$;

bis(n-propylcyclopentadienyl)$M^c(R)_2$;

dimethylsilyl (tetramethylcyclopentadienyl)(cyclododecylamido)$M^c(R)_2$;

dimethylsilyl (tetramethylcyclopentadienyl)(cyclododecylamido)$M^c(R)_2$;

dimethylsilyl (tetramethylcyclopentadienyl)(t-butylamido) $M^c(R)_2$;

dimethylsilyl (tetramethylcyclopentadienyl)(t-butylamido) $M^c(R)_2$;

1,1'-bis(4-triethylsilylphenyl)(methylene)(cyclopentadienyl)(fluorenyl)$M^c(R)_2$;

μ-$(CH_3)_2$Si(cyclopentadienyl)(1-adamantylamido)$M^c(R)_2$;

μ-$(CH_3)_2$Si(3-tertbutylcyclopentadienyl)(1-adamantylamido)$M^c(R)_2$;

μ-$(CH_3)_2$(tetramethylcyclopentadienyl)(1-adamantylamido) $M^c(R)_2$;

μ-$(CH_3)_2$Si(tetramethylcyclopentadienyl)(1-adamantylamido)$M^c(R)_2$;

μ-$(CH_3)_2$C(tetramethylcyclopentadienyl)(1-adamantylamido)$M^c(R)_2$;

μ-$(CH_3)_2$Si(tetramethylcyclopentadienyl)(1-tertbutylamido) $M^c(R)_2$;

μ-$(CH_3)_2$Si(fluorenyl)(1-tertbutylamido)$M^c(R)_2$;

μ-$(CH_3)_2$Si(tetramethylcyclopentadienyl)(1-cyclododecylamido)$M^c(R)_2$;

μ-$(C_6H_5)_2$C(tetramethylcyclopentadienyl)(1-cyclododecylamido)$M^c(R)_2$;

μ-$(CH_3)_2$Si($\eta^5$-2,6,6-trimethyl-1,5,6,7-tetrahydro-s-indacen-1-yl)(tertbutylamido)$M^c(R)_2$; where $M^c$ is selected from Ti, Zr, and Hf; and R is selected from halogen or $C_1$ to $C_5$ alkyl.

41A. The catalyst system of paragraph 37A, wherein the catalyst is rac-dimethylsilyl-bis(indenyl)hafnium dimethyl.

42A. The catalyst system of paragraph 37A, wherein the catalyst is represented by Formula (CAT-2):

(CAT-2)

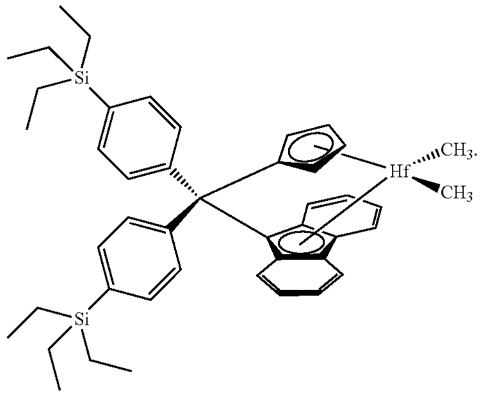

43A. The catalyst system of paragraph 37A, wherein the catalyst is represented by Formula (CAT-3):

(CAT-3)

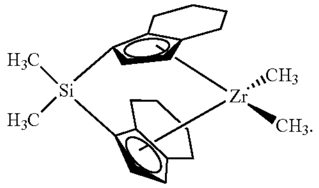

44A. The catalyst system of paragraph 37A, wherein the catalyst is represented by Formula (CAT-4):

(CAT-4)

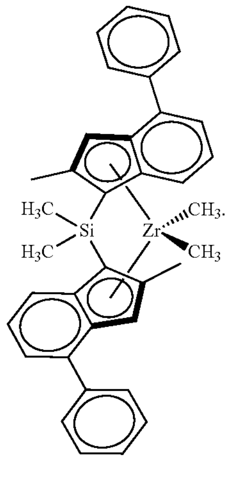

45A. The catalyst system of paragraph 37A, wherein the catalyst is represented by Formula (V):

(V)

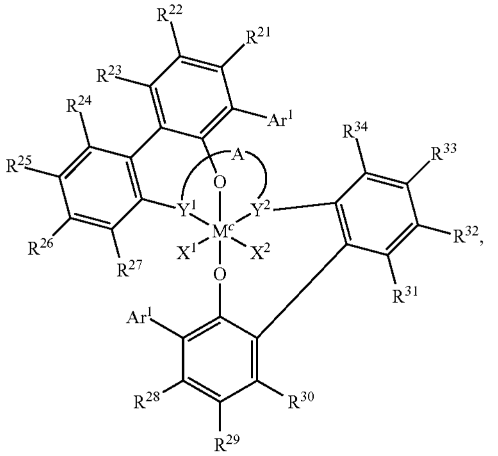

wherein in Formula (V):

$M^c$ is an element selected from group 4 of the Periodic Table of the Elements;

$R^{21}$, $R^{22}$, $R^{23}$, $R^{24}$, $R^{25}$, $R^{26}$, $R^{29}$, $R^{30}$, $R^{31}$, $R^{32}$, $R^{33}$ and $R^{34}$ are independently hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more P groups can combine together into ring structures with such ring structures having from 3 to 100 non-hydrogen atoms in the ring;

A is a $C_1$-$C_{50}$ alkyl group;

$Y^1$ and $Y^2$ are independently selected from O, S, $NR^a$ and $PR^a$ wherein $R^a$ is optionally substituted hydrocarbyl;

$Ar^1$ is phenyl, naphthyl, biphenyl, anthracenyl, or phenanthrenyl; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, alkylaryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

46A. The catalyst system of paragraph 45A, wherein $M^c$ is Zr.

47A. The catalyst system of paragraph 45A, wherein $Y^1$ and $Y^2$ are O.

48A. The catalyst system of paragraph 45A, wherein $X^1$ and $X^2$ are benzyl

49A. The catalyst system of paragraph 45A, wherein A is propyl or butyl.

50A. The catalyst system of paragraph 45A, wherein the catalyst is represented by Formula (CAT-5):

(CAT-5)

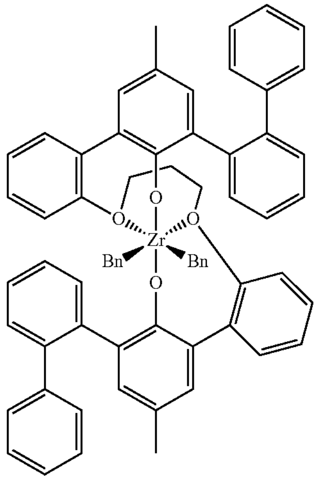

51A. The catalyst system of paragraph 45A, wherein the catalyst is represented by Formula (CAT-6):

(CAT-6)

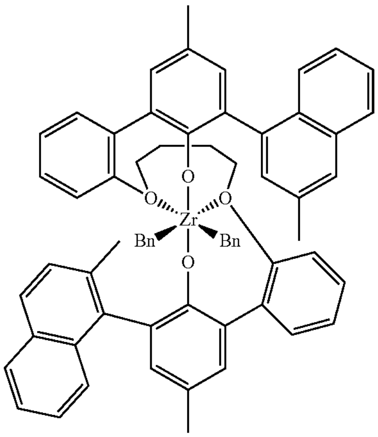

52A. The catalyst system of paragraph 34A, wherein the catalyst is represented by Formulas (VIa) or (VIb):

(VIa)

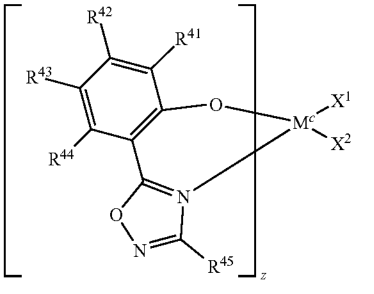

-continued (VIb)

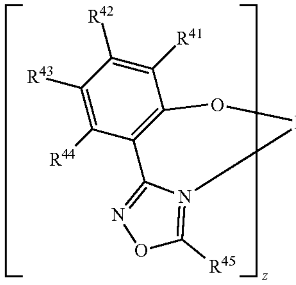

wherein in Formulas (VIa) or (VIb):

$M^c$ is an element selected from group 4 of the Periodic Table of the Elements $R^{41}$, $R^{42}$, $R^{43}$, $R^{44}$, $R^{45}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand; and z is 1, 2, 3, or 4.

53A. The catalyst system of paragraph 52A, wherein $M^c$ is Zr.

54A. The catalyst system of paragraph 52A, wherein $X^1$ and $X^2$ are benzyl.

55A. The catalyst system of paragraph 52A, wherein the catalyst is represented by Formula (CAT-7):

(CAT-7)

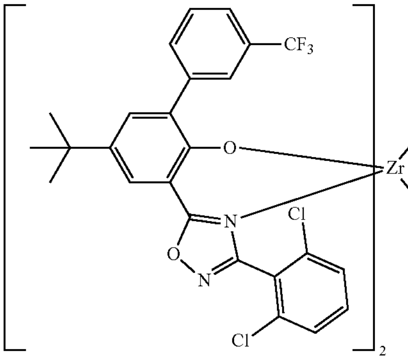

56A. The catalyst system of paragraph 34A, wherein the catalyst is represented by Formula (VII):

(VII)

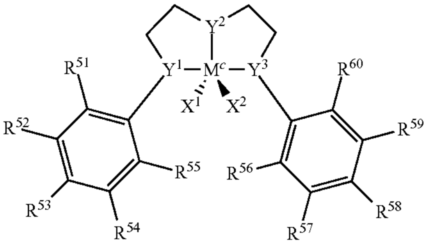

wherein in Formula (VII):

$M^c$ is an element selected from group 4 of the Periodic Table of the Elements $R^{51}$, $R^{52}$, $R^{53}$, $R^{54}$, $R^{55}$, $R^{56}$, $R^{57}$, $R^{58}$, $R^{59}$, $R^{60}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$Y^1$ and $Y^2$ are independently O, N, NH, or S; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxyl, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

57A. The catalyst system of paragraph 56A, wherein the catalyst is represented by Formula (CAT-8):

(CAT-8)

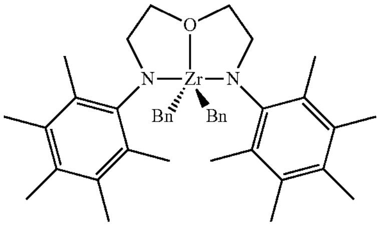

58A. The catalyst system of paragraph 56A, wherein the catalyst is represented by Formula (CAT-9):

(CAT-9)

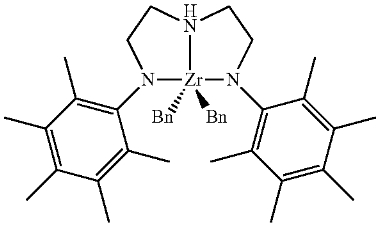

59A. A method comprising contacting at least one olefin with the catalyst system of paragraph 34A, and obtaining a polyolefin.

60A. The method of paragraph 59A, wherein the at least one olefin comprises propylene.

61A. The method of paragraph 60A, wherein the polyolefin has an Mw of about 25,000 to about 300,000 g/mol and a melt temperature of about 100° C. to about 130° C.

62A. The method of paragraph 59A, wherein the at least one olefin comprises ethylene.

63A. The method of paragraph 62A, wherein the polyolefin has an Mw of about 250,000 to about 2,500,000 g/mol and a melt temperature of about 120° C. to about 140° C.

64A. A method comprising contacting two or more different olefins with the catalyst system of paragraph 34A; and obtaining a polyolefin.

65A. The method of paragraph 64A, wherein the two or more olefins are ethylene and octene.

66A. The method of paragraph 65A, wherein the polyolefin has an Mw of from about 50,000 to about 1,500,000 g/mol and a melt temperature of from about 25° C. to about 100° C.

67A. The method of paragraph 59A, wherein contacting is performed in the gas phase or slurry phase.

68A. The method of paragraph 64A, wherein contacting is performed in the gas phase or slurry phase.

69A. A solution comprising the compound of any one of paragraphs 1A, 2A, 6A-8A, or 19A-29A and an aliphatic solvent; wherein aromatic solvents are absent.

70A. A solution comprising the catalyst system of paragraph 34A and an aliphatic solvent; wherein aromatic solvents are absent.

The present disclosure still further relates to

1B. A compound represented by Formula (I):

$$[Ar(EHR^1R^2)(OR^3)]_d^+[M^{k+}Q_n]^{d-} \quad (I)$$

wherein:

Ar is an aryl group;

E is nitrogen or phosphorous;

$R^1$ is a $C_1$-$C_{30}$, optionally substituted, linear alkyl group;

$R^2$ is a $C_1$-$C_{30}$, optionally substituted, linear alkyl group;

$R^3$ is a $C_{10}$-$C_{30}$, optionally substituted, linear alkyl group;

M is an element selected from group 13 of the Periodic Table of the Elements;

d is 1, 2 or 3; k is 1, 2, or 3; n is 1, 2, 3, 4, 5, or 6; n−k=d; and each Q is independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

2B. The compound of paragraph 1B, wherein $R^1$ is a $C_1$ to $C_{10}$ linear alkyl group.

3B. The compound of paragraph 1B, wherein $R^1$ is methyl, ethyl, propyl, butyl, pentyl, or hexyl.

4B. The compound of paragraph 2B, wherein $R^2$ is a $C_1$-$C_{20}$, optionally substituted, linear alkyl group.

5B. The compound of paragraph 2B, wherein $R^3$ is a $C_{10}$-$C_{20}$, optionally substituted, linear alkyl group.

6B. The compound of paragraph 1B, wherein $R^1$ is methyl.

7B. The compound of paragraph 6B, wherein $R^2$ is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

8B. The compound of paragraph 7B, wherein $R^3$ is n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

9B. The compound of paragraph 1B, wherein E is nitrogen.

10B. The compound of paragraph 1B, wherein M is boron and k is 3.

11B. The compound of paragraph 1B, wherein M is boron and E is nitrogen.

12B. The compound of paragraph 11B, wherein Q is an optionally substituted aryl group.

13B. The compound of paragraph 11B, wherein Q is a halogen substituted aryl group.

14B. The compound of paragraph 11B, wherein Q is a perfluoroaryl group.

15B. The compound of paragraph 11B, wherein Q is a perflurophenyl group.

16B. The compound of paragraph 11B, wherein Q is a perfluoronaphthyl group.

17B. The compound of paragraph 11B, wherein $R^1$, $R^2$, and $R^3$ together comprise 20 or more carbon atoms.

18B. The compound of paragraph 1B, wherein Ar is a phenyl group.

19B. A compound represented by Formula (II):

$$[Cat]^+[MQ_4]^- \quad (II)$$

wherein:

M is an element selected from group 13 of the Periodic Table of the Elements;

Q is a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical; and $[Cat]^-$ is a cation represented by a structure selected from the group consisting of

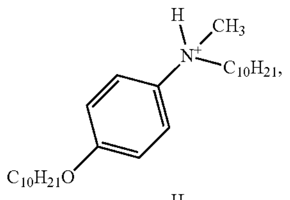

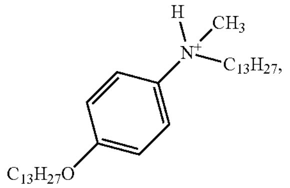

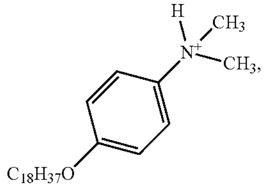

and

-continued

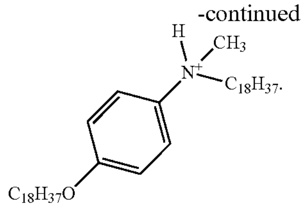

20B. The compound of paragraph 19B, wherein Q is an optionally substituted aryl group.

21B. The compound of paragraph 20B, wherein Q is a halogen substituted aryl group.

22B. The compound of paragraph 19B, wherein Q is a perfluoroaryl group.

23B. The compound of paragraph 19B, wherein Q is a perfluophenyl group.

24B. The compound of paragraph 19B, wherein Q is a perfluoronaphthyl group.

25B. The compound of paragraph 19B, wherein M is boron.

26B. A compound represented by Formula (III):

$$[R^{11}R^{12}R^{13}EH]^{+}[BR^{14}R^{15}R^{16}R^{17}]^{-} \quad \text{(II)}$$

wherein:

E is nitrogen or phosphorous;

each of $R^{11}$, $R^{12}$, and $R^{13}$ is independently a $C_1$-$C_{30}$ linear alkyl group or an aryl group, wherein the aryl group is substituted with at least one $C_{10}$-$C_{30}$ alkoxy group, wherein $R^{11}$, $R^{12}$, and $R^{13}$ together comprise 26 or more carbon atoms; and each of $R^{14}$, $R^{15}$, $R^{16}$, and $R^{17}$ is independently an aryl group, wherein at least one of $R^{14}$, $R^{15}$, $R^{16}$, and $R^{17}$ is substituted with from one to seven fluorine atoms.

27B. The compound of paragraph 26B, wherein each of $R^{11}$ and $R^{12}$ is independently a $C_1$-$C_{30}$ linear alkyl, and $R^{13}$ is an aryl group substituted with a $C_{10}$-$C_{30}$ alkoxy group.

28B. The compound of paragraph 27B, wherein $R^{11}$, $R^{12}$, and $R^{13}$ together comprise 30 or more carbon atoms.

29B. The compound of paragraph 27B, wherein $R^{11}$, $R^{12}$, and $R^{13}$ together comprise 40 or more carbon atoms.

30B. The compound of paragraph 26B, wherein E is nitrogen.

31B. The compound of paragraph 1B, wherein the compound has a solubility of at least 10 mM at 25° C. in methylcyclohexane.

32B. The compound of paragraph 1B, wherein the compound has a solubility of at least 10 mM at 25° C. in isohexane.

33B. The compound of paragraph 1B, wherein the compound has a solubility of at least 10 mM at 25° C. in methylcyclohexane and a solubility of at least 10 mM at 25° C. in isohexane.

34B. A catalyst system comprising a catalyst and an activator comprising the compound of paragraph 1B.

35B. The catalyst system of paragraph 34B, further comprising a support material.

36B. The catalyst system of paragraph 35B, wherein the support material is selected from $Al_2O_3$, $ZrO_2$, $SiO_2$, $SiO_2/Al_2O_3$, $SiO_2/TiO_2$, silica clay, silicon oxide/clay, and mixtures thereof.

37B. The catalyst system of paragraph 34B, wherein the catalyst is represented by Formula (IV):

(IV)

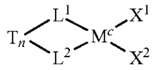

wherein in Formula (IV):

$M^c$ is an element selected from group 4 of the Periodic Table of the Elements;

n is 0 or 1;

T is an optional bridging group selected from S, O, PR', NR', SiR"$_2$, $CH_2$, CHR", or CR"$_2$, wherein R' is a $C_1$-$C_{30}$, optionally substituted, hydrocarbyl group and R" is hydrogen or a $C_1$-$C_{30}$, optionally substituted, hydrocarbyl group;

$L^1$ and $L^2$ are independently cyclopentadienyl, substituted cyclopentadienyl, indenyl, substituted indenyl, tetrahydroindenyl, substituted tetrahydroindenyl, fluorenyl, or substituted fluorenyl groups; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

38B. The catalyst system of paragraph 37B, wherein T is an optional bridging group selected from dialkylsilyl, diarylsilyl, dialkylmethyl, diarylmethyl, ethylenyl, or hydrocarbylethylenyl wherein one, two, three or four of the hydrogen atoms in ethylenyl are substituted by hydrocarbyl.

39B. The catalyst system of paragraph 37B, wherein the catalyst is $C_2$ symmetrical.

40B. The catalyst system of paragraph 37B, wherein the catalyst is one or more of:

dimethylsilyl bis(indenyl)$M^c(R)_2$;
dimethylsilyl bis(tetrahydroindenyl)$M^c(R)_2$;
bis(1-methyl, 3-n-butyl cyclopentadienyl)$M^c(R)_2$;
bis(indenyl)$M^c(R)_2$;
dimethylsilyl bis(tetrahydroindenyl)$M^c(R)_2$;
bis(n-propylcyclopentadienyl)$M^c(R)_2$;
dimethylsilyl (tetramethylcyclopentadienyl)(cyclododecylamido)$M^c(R)_2$;
dimethylsilyl (tetramethylcyclopentadienyl)(cyclododecylamido)$M^c(R)_2$;
dimethylsilyl (tetramethylcyclopentadienyl)(t-butylamido) $M^c(R)_2$;
dimethylsilyl (tetramethylcyclopentadienyl)(t-butylamido) $M^c(R)_2$;
1,1'-bis(4-triethylsilylphenyl)(methylene)(cyclopentadienyl)(fluorenyl)$M^c(R)_2$;
μ-$(CH_3)_2$Si(cyclopentadienyl)(1-adamantylamido)$M^c(R)_2$;
μ-$(CH_3)_2$Si(3-tertbutylcyclopentadienyl)(1-adamantylamido)$M^c(R)_2$;
μ-$(CH_3)_2$(tetramethylcyclopentadienyl)(1-adamantylamido) $M^c(R)_2$;
μ-$(CH_3)_2$Si(tetramethylcyclopentadienyl)(1-adamantylamido)$M^c(R)_2$;
μ-$(CH_3)_2$C(tetramethylcyclopentadienyl)(1-adamantylamido)$M^c(R)_2$;

$\mu$-$(CH_3)_2$Si(tetramethylcyclopentadienyl)(1-tertbutylamido)$M^c(R)_2$;

$\mu$-$(CH_3)_2$Si(fluorenyl)(1-tertbutylamido)$M^c(R)_2$;

$\mu$-$(CH_3)_2$Si(tetramethylcyclopentadienyl)(1-cyclododecylamido)$M^c(R)_2$;

$\mu$-$(C_6H_5)_2$C(tetramethylcyclopentadienyl)(1-cyclododecylamido)$M^c(R)_2$;

$\mu$-$(CH_3)_2$Si($\eta^5$-2,6,6-trimethyl-1,5,6,7-tetrahydro-s-indacen-1-yl)(tertbutylamido)$M^c(R)_2$; where $M^c$ is selected from Ti, Zr, and Hf; and R is selected from halogen or $C_1$ to $C_5$ alkyl.

41B. The catalyst system of paragraph 37B, wherein the catalyst is rac-dimethylsilyl-bis(indenyl)hafnium dimethyl.

42B. The catalyst system of paragraph 37B, wherein the catalyst is represented by Formula (CAT-2):

(CAT-2)

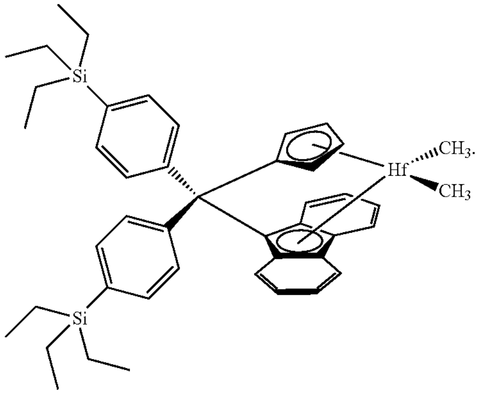

43B. The catalyst system of paragraph 37B, wherein the catalyst is represented by Formula (CAT-3):

(CAT-3)

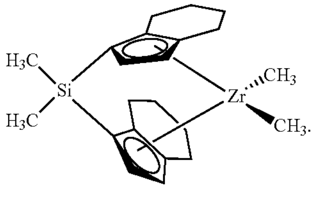

44B. The catalyst system of paragraph 37B, wherein the catalyst is represented by Formula (CAT-4):

(CAT-4)

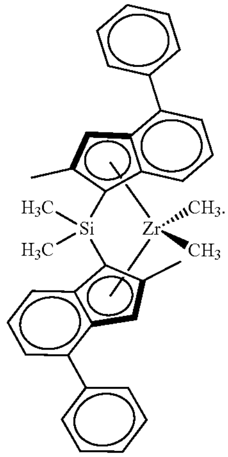

45B. The catalyst system of paragraph 37B, wherein the catalyst is represented by Formula (V):

(V)

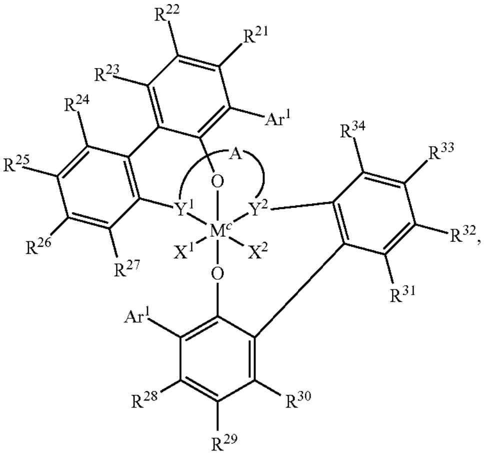

wherein in Formula (V);

$M^c$ is an element selected from group 4 of the Periodic Table of the Elements;

$R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$ are independently hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring;

A is a $C_1$-$C_{50}$ alkyl group;

$Y^1$ and $Y^2$ are independently selected from O, S, $NR^a$ and $PR^a$ wherein $R^a$ is optionally substituted hydrocarbyl;

$Ar^1$ is phenyl, naphthyl, biphenyl, anthracenyl, or phenanthrenyl; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, alkylaryl, heteroaryl, substituted heteroaryl, alkoxy, substituted, alkoxy, aryloxy, substituted aryloxy, boryl amino, phosphine, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

46B. The catalyst system of paragraph 45B, wherein M is Zr.

47B. The catalyst system of paragraph 45B, wherein $Y^1$ and $Y^2$ are O.

48B. The catalyst system of paragraph 45B, wherein $X^1$ and $X^2$ are benzyl.

49B. The catalyst system of paragraph 45B, wherein A is propyl or butyl.

50B. The catalyst system of paragraph 45B, wherein the catalyst is represented by Formula (CAT-5):

(CAT-5)

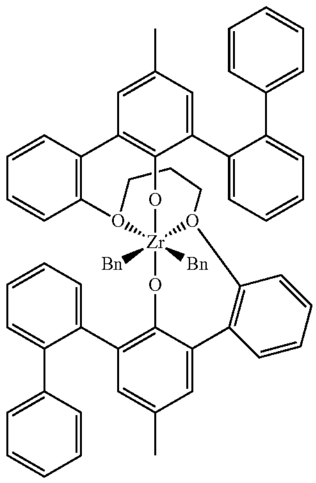

51B. The catalyst system of paragraph 45B, wherein the catalyst is represented by Formula (CAT-6):

(CAT-6)

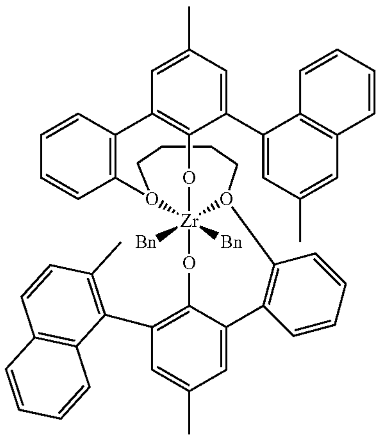

52B. The catalyst system of paragraph 34B, wherein the catalyst is represented by Formulas (VIa) or (VIb):

(VIa)

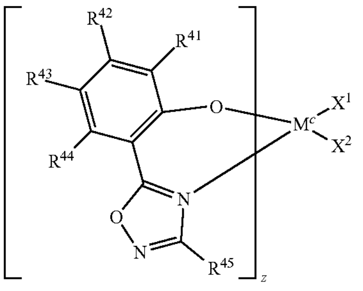

(VIb)

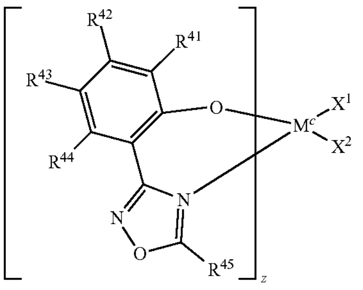

wherein in Formulas (VIa) or (VIb):

$M^c$ is an element selected from group 4 of the Periodic Table of the Elements $R^{41}$, $R^{42}$, $R^{43}$, $R^{44}$, $R^{45}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand; and z is 1, 2, 3, or 4, 53B. The catalyst system of paragraph 52B, wherein $M^c$ is Zr.

54B. The catalyst system of paragraph 52B, wherein $X^1$ and $X^2$ are benzyl.

55B. The catalyst system of paragraph 52B, wherein the catalyst is represented by Formula (CAT-7):

(CAT-7)

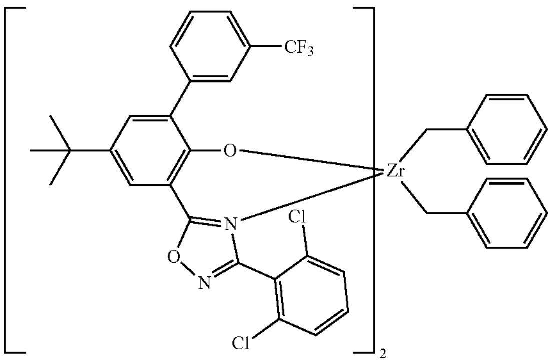

56B. The catalyst system of paragraph 34B, wherein the catalyst is represented by Formula (VII):

(VII)

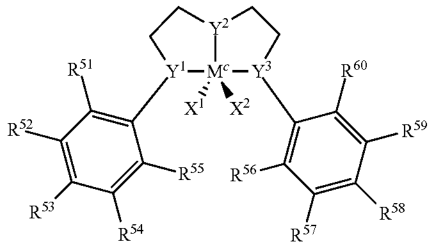

wherein in Formula (VII):

$M^c$ is an element selected from group 4 of the Periodic Table of the Elements $R^{51}$, $R^{52}$, $R^{53}$, $R^{54}$, $R^{55}$, $R^{56}$, $R^{57}$, $R^{58}$, $R^{59}$, $R^{60}$ are independently selected from the group consisting of hydrogen, alkyl, substituted alkyl cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof;

$Y^1$ and $Y^2$ are independently O, N, NH, or S; and $X^1$ and $X^2$ are, independently, hydrogen, halogen, hydrocarbyl, substituted hydrocarbyl, halocarbyl, substituted halocarbyl, silyl, silylcarbyl, substituted silylcarbyl, germylcarbyl, substituted germylcarbyl, aryl, substituted aryl, heteroaryl, substituted heteroaryl, alkoxy, substituted alkoxy, aryloxy, substituted aryloxy, boryl, amino, phosphino, ether, thioether, phosphine, amine, carboxylate, alkylthio, arylthio, 1,3-dionate, oxalate, carbonate, nitrate, or sulphate, or both $X^1$ and $X^2$ are joined and bound to the metal atom to form a metallacycle ring containing from about 3 to about 20 carbon atoms; or both together can be an olefin, diolefin or aryne ligand.

57B. The catalyst system of paragraph 56B, wherein the catalyst is represented by Formula (CAT-8):

(CAT-8)

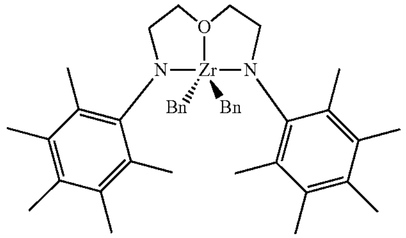

58B. The catalyst system of paragraph 56B, wherein the catalyst is represented by Formula (CAT-9):

(CAT-9)

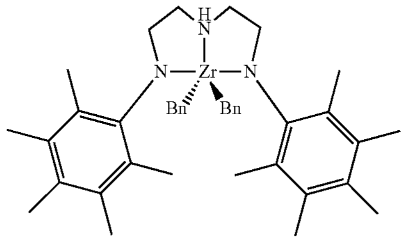

59B. A method comprising contacting at least one olefin with the catalyst system of paragraph 34B, and obtaining a polyolefin.

60B. The method of paragraph 59B, wherein the at least one olefin comprises propylene.

61B. The method of paragraph 60B, wherein the polyolefin has an Mw of about 25,000 to about 300,000 g/mol and a melt temperature of about 100° C. to about 130° C.

62B. The method of paragraph 59B, wherein the at least one olefin comprises ethylene.

63B. The method of paragraph 62B, wherein the polyolefin has an Mw of about 250,000 to about 2,500,000 g/mol and a melt temperature of about 120° C. to about 140° C.

64B. A method comprising contacting two or more different olefins with the catalyst system of paragraph 34B; and obtaining a polyolefin.

65B. The method of paragraph 64B, wherein the two or more olefins are ethylene and octene.

66B. The method of paragraph 65B, wherein the polyolefin has an Mw of from about 50,000 to about 1,500,000 g/mol and a melt temperature of from about 25° C. to about 100° C.

67B. The method of paragraph 59B, wherein contacting is performed in the gas phase or slurry phase.

68B. The method of paragraph 64B, wherein contacting is performed in the gas phase or slurry phase.

69B. A solution comprising the compound of paragraph 1B and an aliphatic solvent; wherein aromatic solvents are absent.

70B. A solution comprising the catalyst system of paragraph 34B and an aliphatic solvent; wherein aromatic solvents are absent.

To facilitate a better understanding of the embodiments of the present invention, the following example of preferred or representative embodiments are given. In no way should the following example be read to limit, or to define, the scope of the invention.

EXAMPLES

Experimental

Lithium tetrakis(pentafluorophenyl)borate etherate (Li—BF20) was purchased from Boulder Scientific. N,N-Dimethylanilinium tetrakis(pentafluorophenyl)borate (DMAH-A1) was purchased from Grace Davison and converted to sodium tetrakis(heptafluoronaphthalen-2-yl)borate (Na—BF28) by reaction with sodium hydride in toluene. N,N-dimethylanilinium tetrakis(heptafluoronaphthalen-2-yl)borate (DMAH-A2) was purchased from Grace Davison. EXXAL™ 13 is an oxo alcohol produced by ExxonMobil Chemical Company, Houston, Texas, and is a mixture of isomers. All other reagents were purchased from Sigma-Aldrich and used as received. All anhydrous solvents were purchased from Sigma-Aldrich. Solvents (Sigma-Aldrich) were sparged with nitrogen and stored over molecular sieves.

$^{1}H$ NMR for Compound Characterization: Chemical structures were determined by $^{1}H$ NMR. $^{1}H$ NMR data are collected at room temperature (e.g., 23° C.) in a 5 mm probe. The $^{1}H$ NMR measurements were recorded on a 400 MHz or 500 MHz Bruker spectrometer with chemical shifts referenced to residual solvent peaks ($CDCl_3$: 7.27 ppm for $^{1}H$, 77.23 ppm for $^{13}C$).

EXAMPLES

Borate anions and ammonium cations used as activator components are shown in Table 3.

TABLE 3

Borate Anions and Ammonium Cations used as Activator Components

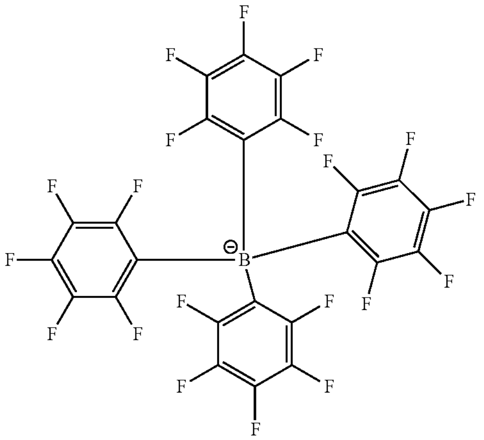 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

A1

TABLE 3-continued

Borate Anions and Ammonium Cations used as Activator Components

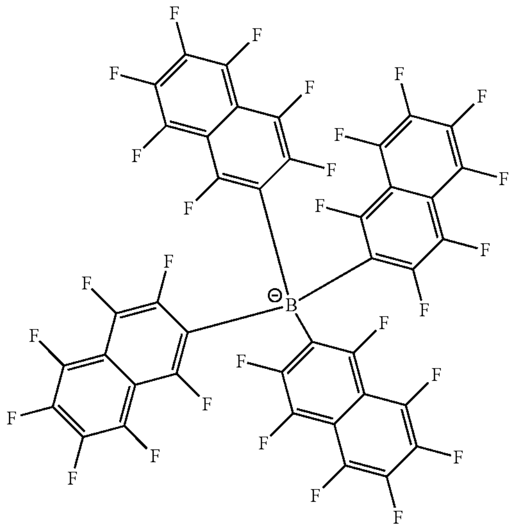 [SMILES: Fc1c(F)c(F)c2c(F)c([B-](c3c(F)c(F)c4c(F)c(F)c(F)c(F)c4c3F)(c3c(F)c(F)c4c(F)c(F)c(F)c(F)c4c3F)c3c(F)c(F)c4c(F)c(F)c(F)c(F)c4c3F)c(F)c(F)c2c1F]

A2

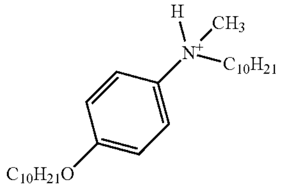

C1

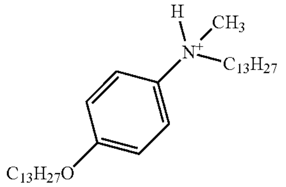

C2

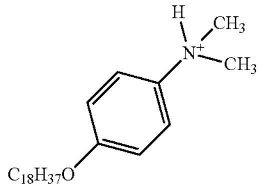

C3

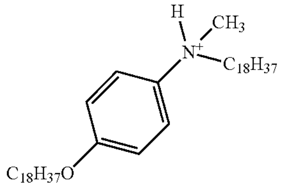

C4

Synthesis of Activators

General Synthesis of Ammonium Borate Activators: Ammonium borate activators were prepared using a three-step process. In the first step, an alkylated amine containing an ether group was prepared from an aminophenol and a bromoalkane in the presence of sodium hydride in a solvent (e.g., tetrahydrofuran). The resulting alkylated amine was then dissolved in a solvent (e.g., hexane, cyclohexane, methylcyclohexane, ether, dichloromethane, toluene) and an excess (ca. 1.2 molar equivalents) of hydrogen chloride was added to form an ammonium chloride salt. This salt was isolated by filtration from the reaction medium and dried under reduced pressure. The isolated ammonium chloride was then heated to reflux with one molar equivalent of an alkali metal borate in a solvent (e.g. cyclohexane, dichloromethane, methylcyclohexane) to form the ammonium borate along with byproduct alkali metal chloride, the latter which typically is removed by filtration. Examples describing the synthetic details for selected ammonium borates are given below.

N-methyl-N-octadecyl-4-(octadecyloxy)aniline

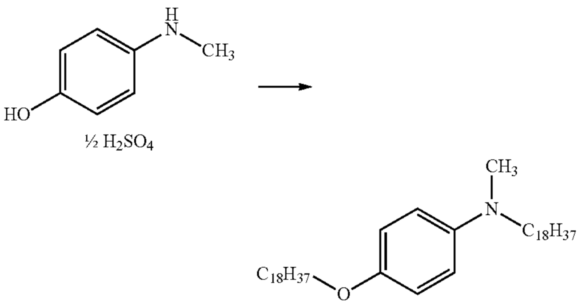

4-(methylamino)phenol hemisulfate and bromooctadecane were dissolved in THF. Sodium hydride was added slowly. The reaction was allowed to stir overnight, then quenched with ice water and ether. The ether portion was concentrated and the residue purified by passage through a silica gel plug (0-10% acetone/isohexane) to give the alkyl product as a fluffy white solid in 60% yield: $^1$H NMR (500 MHz, $C_6D_6$, δ): 0.90 (m, 6H), 1.33 (m, 58H), 1.45 (m, 4H), 1.71 (m, 2H), 2.64 (s, 3H), 3.08 (m, 2H), 3.80 (m, 2H), 6.72 (m, 2H), 6.98 (m, 2H); $^{13}$C NMR: 14.0 (2C), 22.8 (2C), 26.2-32.0 (30C), 38.6, 53.9, 68.2, 114.7 (2C), 115.6 (2C), 144.8, 151.9.

N-methyl-N-octadecyl-4-(octadecyloxy)anilinium chloride: The above oxyaniline (3.0 g, 4.77 mmol) was dissolved in 50 mL of hexane. Ethereal HCl (2.86 mL, 2M) was added and a white precipitate formed within 10 minutes. The reaction was stirred overnight before collecting the solid salt.

N-methyl-N-octadecyl-4-(octadecyloxy)anilinium tetrakis(pentafluorophenyl)borate (C4-A1): The above N-methyl-N-octadecyl-4-(octadecyloxy)anilinium chloride salt (0.5 g, 0.75 mmol) was slurried with Li—BF20 (0.52 g, 0.75 mmol) in 20 mL of isohexane at heated at 55° C. for 1.5 hours. When cooled to ambient, the solution was filtered and concentrated to a clear colorless oil. The borate salt was obtained in 89% yield.

N-methyl-N-octadecyl-4-(octadecyloxy)anilinium tetrakis(heptafluoronaphthalen-2-yl)borate (C4-A2): The above N-methyl-N-octadecyl-4-(octadecyloxy)anilinium chloride salt (0.5 g, 0.75 mmol) was slurried with Na—BF28 (0.78 g, 0.75 mmol) in 20 mL of isohexane heated at 55° C. for 1.5 hours. When cooled to ambient, the solution was filtered and concentrated to a brown oil. The borate salt was obtained in 89% yield.

Tridecylbromide: Oxo alcohol EXXAL® 13 (available from ExxonMobil) (45.0 g, 225 mmol) and triphenylphosphine (117.8 g, 449 mmol) were dissolved in methylene chloride (200 mL). Carbon tetrabromide (89.3 g, 270 mmol) was added at a slow rate to prevent reflux. Upon completion, diethyl ether was added to cause a white precipitate, which was filtered away. The filtrate was concentrated to a white solid and the solid extracted with pentane. The pentane fractions were concentrated to a colorless oil. NMR analysis indicated the presence of triphenylphosphine oxide, thus the oil was extracted with pentane twice more. The bromide was obtained in 60% yield as a pale yellow oil.

N-methyl-N-tridecyl-4-(tridecyloxy)aniline

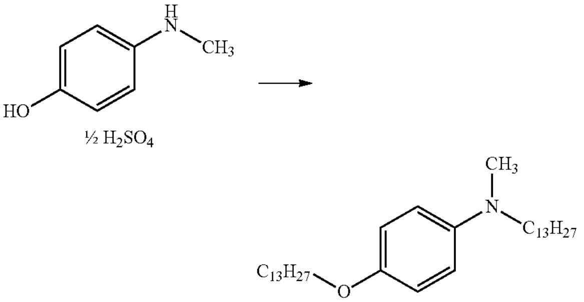

4-(methylamino)phenol hemisulfate (2.0 g, 11.6 mmol) and tridecylbromide (6.42 g, 24.4 mmol) were dissolved in 200 mL of THF. Sodium hydride (95%, 0.95 g, 37.7 mmol) was added slowly and the reaction warmed at 70° C. overnight. Upon cooling, ether was added and the reaction quenched with ice water. The ether layer was concentrated to a dark oil which was purified by passage through a silica gel plug (10% acetone/isohexane). $^1$H NMR (500 MHz, $C_6D_6$, δ): 1.25 (m, 50H), 2.64 (s, 3H), 3.08 (m, 2H), 3.79 (m, 2H), 6.73 (m, 2H), 6.99 (m, 2H).

N-methyl-N-tridecyl-4-(tridecyloxy)anilinium chloride: The alkylated oxyaniline (0.47 g, 0.96 mmol) was dissolved in 5 mL of isohexane and ethereal HCl (0.57 mL, 2M) was added. The reaction was stirred overnight then concentrated to a pale yellow oil. $^1$H NMR (500 MHz, $CDCl_3$, δ): 1.26 (m, 50H), 3.12 (s, 3H), 3.42 (m, 2H), 3.97 (m, 2H), 6.98 (m, 2H), 7.67 (m, 2H).

N-methyl-N-tridecyl-4-(tridecyloxy)anilinium tetrakis(pentafluorophenyl)borate (C2-A1): The above N-methyl-N-tridecyl-4-(tridecyloxy)anilinium chloride salt (0.27 g, 0.52 mmol) was slurried with Li—BF20 (0.39 g, 0.52 mmol) in 20 mL of isohexane at heated at 80° C. for 1.5 hours. When cooled to ambient, the solution was filtered and concentrated to a light tan solid. The borate salt was obtained in 56% yield. $^1$H NMR (400 MHz, $CDCl_3$, δ): 0.89-1.68 (m, 46H), 3.28 (s, 3H), 3.57 (m, 4H), 4.03 (m, 2H), 7.05 (m, 2H), 7.15 (m, 2H).

N-methyl-N-decyl-4-(decyloxy)aniline

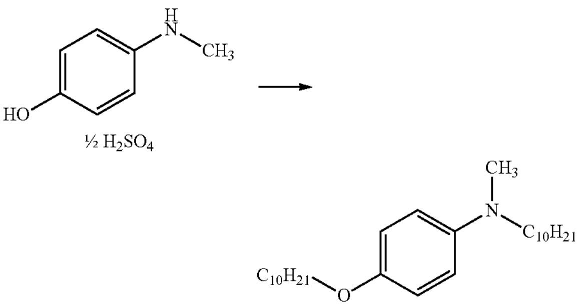

4-(methylamino)phenol hemisulfate (5.0 g) and iododecane (13.9 mL, 65.33 mmol) were dissolved in THF. Sodium hydride (1.8 g, 72.5 mmol) was added slowly. The reaction was allowed to stir overnight, then quenched with ice water and ether. The ether portion was concentrated and the residue purified by passage through a silica gel plug (0-10% acetone/isohexane) to give the alkyl product as a clear colorless oil. $^1$H NMR (500 MHz, $CDCl_3$, δ): 0.90 (m, 6H), 1.25 (m, 26H), 1.46 (m, 4H), 1.70 (m, 2H), 2.63 (s, 3H), 3.07 (m, 2H), 3.79 (t, J=6.5 Hz, 2H), 6.72 (d, J=9 Hz, 2H), 6.98 (d, J=9 Hz, 2H); $^{13}$C NMR: 14.0 (2C), 22.7 (2C), 26.2, 26.7, 27.2, 29.4-29.7 (9C), 31.9 (2C), 38.6, 53.8 (2C), 68.2 (2C), 114.7 (2C), 115.6 (2C), 144.7, 151.6.

N-methyl-N-decyl-4-(decyloxy)anilinium chloride: To the above aniline (1.47 g, 3.64 mmol) dissolved in 100 mL of isohexane was added 2M ethereal HCl (2.18 mL, 4.37 mmol). The solution was allowed to stir at ambient temperature overnight, then concentrated to a clear viscous oil. The HCl salt was obtained 99% crude yield.

N-methyl-N-decyl-4-(decyloxy)anilinium tetrakis(pentafluorophenyl)borate (C1-A1): The above N-methyl-N-decyl-4-(decyloxy)anilinium chloride salt (0.25 g, 0.56 mmol) was slurried with Li—BF20 (0.43 g, 0.56 mmol) in 20 mL of cyclohexane at heated at 80° C. for 1.5 hours. When cooled to ambient, additional cyclohexane was added and the solution filtered and concentrated to a clear colorless oil. The borate salt was obtained in 28% yield. $^1$H NMR (400 MHz, $CDCl_3$, δ): 0.88 (m, 6H), 1.27 (m, 30H), 1.81 (m, 2H), 3.22 (s, 3H), 3.48 (m, 2H), 3.98 (m, 2H), 7.01 (d, J=8.0 Hz, 2H), 7.19 (d, J=8.0 Hz, 2H).

N-methyl-N-decyl-4-(decyloxy)anilinium tetrakis(heptafluoronaphthalen-2-yl)borate (C1-A2): The above N-methyl-N-decyl-4-(decyloxy)anilinium chloride salt (0.25 g, 0.56 mmol) was slurried with Na—BF28 (0.59 g, 0.56 mmol) in 20 mL of cyclohexane at heated at 80° C. for 1.5 hours. When cooled to ambient, an oil separated from the solution, which was dissolved in methylene chloride, filtered and concentrated to the borate salt in 66% yield.

N,N-dimethyl-4-(octadecyloxy)aniline

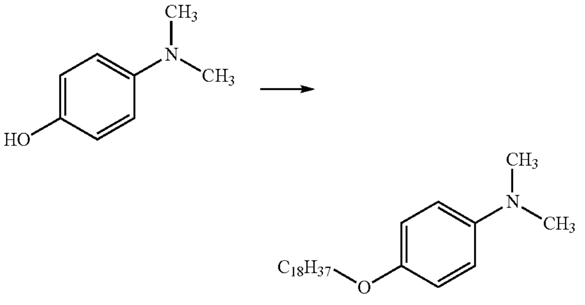

4-(dimethylamino)phenol (1.0 g, 7.3 mmol) and bromooctadecane (2.9 g, 8.7 mmol) were dissolved in 200 mL of THF. Sodium hydride (95%, 0.24 g, 9.4 mmol) was added slowly and the solution heated at reflux for over 2 days. The reaction was quenched with saturated ammonium chloride and extracted with 2 portions of ether. The combined organic fractions were dried ($MgSO_4$), filtered, and concentrated to a brownish solid. Purification by column chromatography (10% acetone/isohexane), gave the aniline in 98% yield as a pale brownish yellow solid. $^1$H NMR (500 MHz, $C_6D_6$, δ): 0.90 (m, 3H), 1.33 (m, 26H), 1.52 (m, 2H), 1.70 (m, 2H), 2.55 (s, 6H), 3.77 (m, 2H), 6.66 (d, J=9.0 Hz, 2H), 6.95 (d, J=9.0 Hz, 2H); $^1$H NMR (500 MHz, $C_6D_6$, δ): 14.0, 22.7-32.0 (16C), 41.1 (2C), 68.1, 114.7 (2C), 115.4 (2C), 145.7, 151.9.

N,N-dimethyl-4-(octadecyloxy)anilinium chloride: To the above aniline (2.8 g, 7.18 mmol) dissolved in 100 mL of isohexane was added ethereal HCl (4.3 mL, 8.62 mmol). A precipitate formed immediately and the mixture was allowed to stir at ambient temperature overnight. It was then filtered and washed with fresh isohexane to give the HCl salt in 68% yield.

N,N-dimethyl-4-(octadecyloxy)anilinium tetrakis(pentafluorophenyl)borate (C3-A1): The above N,N-dimethyl-4-(octadecyloxy)anilinium chloride salt (1.16 g, 2.72 mmol) was slurried with Li—BF20 (2.07 g, 2.72 mmol) in 50 mL of cyclohexane at heated at 80° C. for 1.5 hours. When cooled to ambient, the solution was filtered through Celite and concentrated to a viscous oil. This oil was redissolved in methylene chloride, filtered, and concentrated, giving the borate salt in 81% yield. $^1$H NMR (400 MHz, $C_6D_6$, δ): 0.88 (m, 3H), 1.25 (m, 30H), 1.81 (m, 2H), 3.29 (m, 5H), 3.99 (m, 2H), 7.01 (d, J=8.0 Hz, 2H), 7.21 (d, J=8.0 Hz, 2H).

N,N-dimethyl-4-(octadecyloxy)anilinium tetrakis(heptafluoronaphthalen-2-yl)borate (C3-A2): The above N,N-dimethyl-4-(octadecyloxy)anilinium chloride salt (0.50 g, 1.17 mmol) was slurried with Na—BF28 (1.22 g, 1.17 mmol) in 50 mL of isohexane at heated at 80° C. for 1.5 hours. When cooled to ambient, the oil that separated from the solution was dissolved in methylene chloride, filtered and concentrated to a gray solid. The borate salt was obtained in 57% yield. $^1$H NMR (400 MHz, $C_6D_6$, δ): 0.87 (m, 3H), 1.25 (m, 30H), 1.78 (m, 2H), 3.22 (s, 6H), 3.87 (m, 2H), 6.84 (d, J=8.0 Hz, 2H), 7.25 (m, 2H).

Metal Salts of Tetrakis(Heptafluoronaphthalenyl)Borate Anion

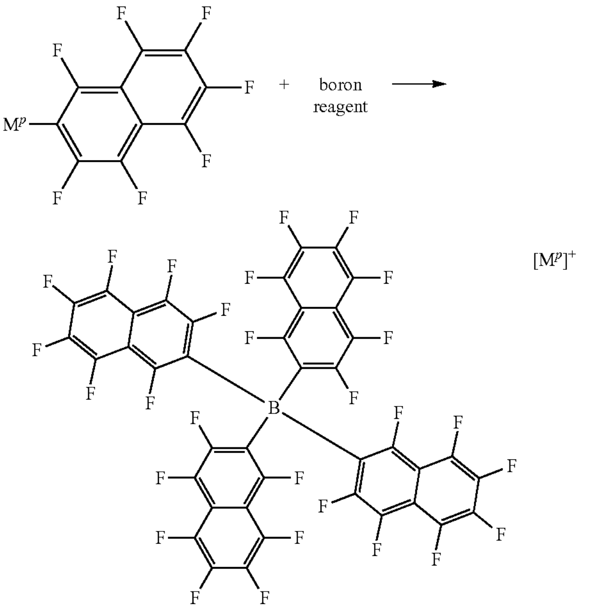

Tetrakis(heptafluoronaphthalenyl)borate salts may be prepared by reaction of a heptafluoronaphthalenyl nucleophile with an appropriate boron reagent. These metal tetrakis (heptafluoronaphthalenyl)borate salts (wherein $M^p$ may be a metal-containing cationic group) are useful intermediates for the preparation of olefin polymerization catalyst components as exemplified in U.S. Pat. No. 9,834,569. These catalyst components that contain the tetrakis(heptafluoronaphthalenyl)borate group are useful for the industrial polymerization of olefins as described in US 2002/0137959 and US 2002/0007025.

Heptafluoronaphthalenyl Nucleophiles

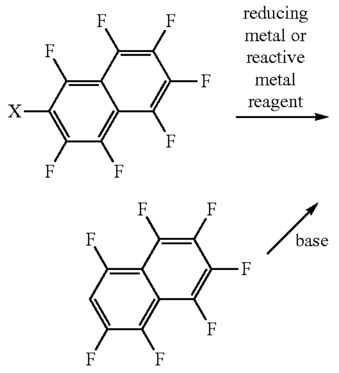

Heptafluoronaphthalenyl nucleophiles (with $M^P$ being a metal-containing cationic group) may be prepared by reaction of 2-X-1,3,4,5,6,7,8-heptafluoronaphthalene (X=chloro, bromo, or iodo) with either a reducing metal or reactive metal reagent. Suitable reducing metals may include group 1, group 2, group 11, group 12, or group 13 metals or combinations of two or more different metals. Reducing metals include Li, Na, K, Mg, Ca, Zn, Cd, Al, and Cu. Reactive metal reagents include group 1 alkyls, Grignard reagents, Grignard reagents in combination with lithium halide, and alkali metal naphthalenides. Reactive metal reagents include BuLi, $^i$PrMgBr, $^i$PrMgCl, $^i$PrMgCl—LiCl, $Bu_2Mg$, EtMgCl, EtMgBr, BnK, K(naphthalene), and K(graphite). Heptafluoronaphthalenyl nucleophiles may also be prepared by reaction of 1,2,3,4,5,6,8-heptafluoronaphthalene with a strong base, such as BuLi, LiO$^t$Bu, or BuNa. The reactions of 2-X-1,3,4,5,6,7,8-heptafluoronaphthalene with a reducing metal or reactive metal reagent may be performed in the presence of an additive. Additives may include lithium halides, magnesium halides, zinc halides, copper halides, fused aromatics, or Lewis bases. For example, the addition of 2-bromo-1,3,4,5,6,7,8-heptafluoronaphthalene to a mixture containing Mg metal, CuBr, and boron trifluoride etherate forms a useful tetrakis(heptafluoronaphthalenyl)borate nucleophile as described by Mathur and Strickler in U.S. Pat. No. 9,738,662. In this example, cuprous bromide was used as an additive. Presumably the reaction proceeds by the initial formation of the Grignard reagent followed by a transmetalation with the CuBr to form a Cu-containing product.

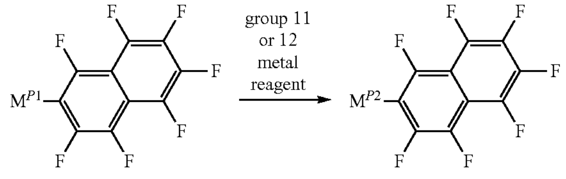

Heptafluoronaphthalenyl metal species that contain a group 1 or 2 metal containing cationic group $M^{P1}$ may be reacted with a group 11 or 12 metal reagent to form a group 11 or 12 metal heptafluoronaphthanenyl species where $M^{P2}$ is a group 11 or 12 metal containing cationic group. The group 1 or group 2 metal containing cationic group $M^{P1}$ may be Li, Na, K, Rb, Cs, magnesium halide, magnesium alkyl, magnesium aryl, magnesium alkoxide, magnesium carboxylate, MgCl, MgBr, calcium halide, or strontium halide. The transition metal containing cationic group $M^{P2}$ may be copper, zinc halide, zinc alkyl, or zinc aryl. For example, heptafluoronaphthalenyl magnesium chloride may be reacted with copper halide, such as CuBr, to form heptafluoronaphthanenyl copper.

Heptafluoronaphthanenyl nucleophiles that may be prepared by the aforementioned methods may include (perfluoronaphthalen-2-yl)lithium, (perfluoronaphthalen-2-yl)sodium, (perfluoronaphthalen-2-yl)potassium, (perfluoronaphthalen-2-yl)rubidium, (perfluoronaphthalen-2-yl)cesium, (perfluoronaphthalen-2-yl)magnesium fluoride, (perfluoronaphthalen-2-yl)magnesium chloride, (perfluoronaphthalen-2-yl)magnesium bromide, (perfluoronaphthalen-2-yl)magnesium iodide, bis(perfluoronaphthalen-2-yl)magnesium, (perfluoronaphthalen-2-yl) calcium fluoride, (perfluoronaphthalen-2-yl)calcium chloride, (perfluoronaphthalen-2-yl)calcium bromide, (perfluoronaphthalen-2-yl)calcium iodide, bis(perfluoronaphthalen-2-yl)calcium, (perfluoronaphthalen-2-yl)zinc fluoride, (perfluoronaphthalen-2-yl)zinc chloride, (perfluoronaphthalen-2-yl)zinc bromide, (perfluoronaphthalen-2-yl) zinc iodide, bis(perfluoronaphthalen-2-yl)zinc, lithium dichloro(perfluoronaphthalen-2-yl)zincate, lithium tris(perfluoronaphthalen-2-yl)zincate, chloromagnesium tris(perfluoronaphthalen-2-yl)zincate, (perfluoronaphthalen-2-yl) copper, lithium bis(perfluoronaphthalen-2-yl)cuprate, chloromagnesium bis(perfluoronaphthalen-2-yl)cuprate, bromomagnesium bis(perfluoronaphthalen-2-yl)cuprate, bis (perfluoronaphthalen-2-yl)cadmium.

Boron Reagents

Boron reagents that may be reacted with heptafluoronaphthalenyl nucleophiles to produce tetrakis(heptafluoronaphthalenyl)borate salts include boron halides, trialkylborates, and alkali metal tetrahaloborates. Boron reagents that may be reacted with heptafluoronaphthalenyl nucleophiles to produce tetrakis(heptafluoronaphthalenyl)borate salts include complexes of the general formula $B(X)_3(L)$, where each X is independently selected from halogens, alkoxides, carboxylates, alkylsulfonates, and hydride, and L is a Lewis base. Boron reagents that may be reacted with heptafluoronaphthalenyl nucleophiles to produce tetrakis(heptafluoronaphthalenyl)borate salts include complexes of the general formula $J[B(X)_4]$, where each X is independently selected from halogens, alkoxides, carboxylates, alkylsulfonates, and hydride, and J is a cationic group containing a group 1 or 2 metal. Boron reagents that may be reacted with heptafluoronaphthalenyl nucleophiles to produce tetrakis(heptafluoronaphthalenyl)borate salts include $BCl_3$, $BBr_3$, $BF_3$, $BF_3(OEt_2)$, $B(OMe)_3$, $B(OEt)_3$, $B(O^iPr)_3$, $B(OBu)_3$, $B(OMe)_2Cl$, $B(O^iPr)_2Cl$, $LiBF_4$, $NaBF_4$, $LiBCl_4$, $NaBCl_4$.

Synthesis of Tetrakis(Heptafluoronaphthalenyl)Borate Salts

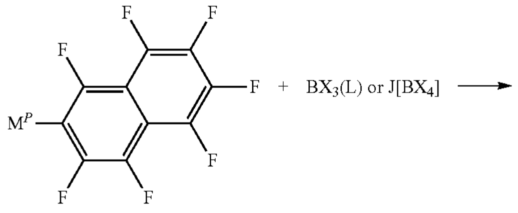

-continued

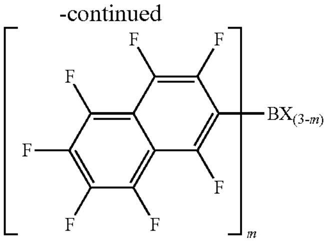

and/or

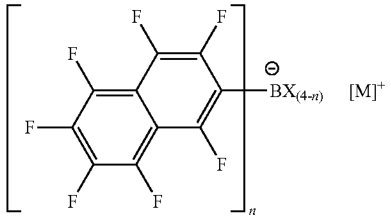

The reaction of a heptafluoronaphthalenyl nucleophile with a boron reagent to produce tetrakis(heptafluoronaphthalenyl)borate salt may be performed in a variety of ways. The heptafluoronaphthalenyl nucleophile may be isolated prior to reaction with the boron reagent. Alternatively, the heptafluoronaphthalenyl nucleophile may be generated in situ and then reacted with the boron reagent. Further alternately, the heptafluoronaphthalenyl nucleophile may be generated in the presence of the boron reagent.

The reaction between a heptafluoronaphthalenyl nucleophile (with $M^p$ being a metal-containing cationic group) and a boron reagent (such as $BX_3(L)$ or $J[BX_4]$) may produce a variety of products that include boranes (m=1 to 3) and borate salts (n=1 to 4). Several of these products may be considered to be intermediates that can be subsequently converted to the desired tetrakis(heptafluoronaphthalenyl) borate salt by further reaction with heptafluoronaphthalenyl nucleophile. A variety of factors will affect the yield and selectivity of each product formed in the reaction. These include the stoichiometry of the reactants, the reaction conditions (e.g. temperature, concentration, duration of reaction), the solvent(s) used, the choice of reagents, the presence of additives and/or catalysts. Ideally the molar ratio of heptafluoronaphthalenylborate nucleophile to boron used in the reaction will be approximately 4. Solvents that may be useful for the reaction include toluene, hexane, isopar C, heptane, pentane, diethyl ether, tetrahydrofuran, methylene chloride, N,N-dimethylfuran, fluorobenzene, aliphatic hydrocarbons, and mixtures of the aforementioned solvents.

Tetrakis(Heptafluoronaphthalenyl)Borate Mixed Metal Salt

Diethyl ether and isopropylmagnesium chloride lithium chloride complex are combined to form a solution. 2-Bromo-1,3,4,5,6,7,8-heptafluoronaphthalene is added and the mixture and it are stirred to form lithium bromochloro (heptafluoronaphthalenyl)magnesate. Boron trichloride is then added to the mixture to form tetrakis(heptafluoronaphthalenyl)borate as a mixed metal salt.

Lithium Tetrakis(Heptafluoronaphthalenyl)Borate

Toluene and butyllithium are combined to form a solution that is cooled to −20° C. 2-Bromo-1,3,4,5,6,7,8-heptafluoronaphthalene is added and the mixture and it is stirred to form heptafluorohaphthalenyllithium. Boron trichloride is then added to the mixture to form lithium tetrakis(heptafluoronaphthalenyl)borate.

Tetrakis(Heptafluoronaphthalenyl)Borate Salt

Magnesium metal, diethyl ether, and a small crystal of iodine are combined. The mixture is stirred for 1 hour then a solution of 2-bromo-1,3,4,5,6,7,8-heptafluoronaphthalene in diethyl ether is added dropwise to form heptafluoronaphthalenylmagnesium bromide. Triisopropylborate is then added to the mixture to form the tetrakis(heptafluoronaphthalenyl)borate salt.

Lithium Tetrakis(Heptafluoronaphthalenyl)Borate

Tetrahydrofuran and 1,2,3,4,5,6,8-heptafluoronaphthalene are combined to form a solution. To this mixture is added lithium tert-butoxide and the mixture is heated to form heptafluorohaphthalenyllithium. Boron trichloride is then added to the mixture to form lithium tetrakis(heptafluoronaphthalenyl)borate.

Tetrakis(Heptafluoronaphthalenyl)Borate Metal Salt

Toluene, 2-bromo-1,3,4,5,6,7,8-heptafluoronaphthalene and cuprous chloride are combined. Then butyllithium is added dropwise and the mixture and it are stirred. Boron trichloride are then added to the mixture to form tetrakis (heptafluoronaphthalenyl)borate as a metal salt.

Tetrakis(Heptafluoronaphthalenyl)Borate as a Mixed Metal Salt

Hexane and dibutylmagnesium are combined to form a solution. 2-Bromo-1,3,4,5,6,7,8-heptafluoronaphthalene is added and the mixture and it are stirred to form bis(heptafluoronaphthalenyl)magnesium. Cuprous bromide and boron trichloride are then added to the mixture to form tetrakis(heptafluoronaphthalenyl)borate as a mixed metal salt.

Polymerization in Parallel Pressure Reactor

Solvents, polymerization-grade toluene, and isohexane were supplied by ExxonMobil Chemical Company and purified by passing through a series of columns: two 500 cc Oxyclear cylinders in series from Labclear (Oakland, Calif.), followed by two 500 cc columns in series packed with dried 3 Å molecular sieves (8-12 mesh; Aldrich Chemical Company), and two 500 cc columns in series packed with dried 5 Å mole sieves (8-12 mesh; Aldrich Chemical Company). 1-octene ($C_8$) and 1-hexene ($C_6$) (98%, Aldrich Chemical Company) were dried by stirring over NaK overnight followed by filtration through basic alumina (Aldrich Chemical Company, Brockman Basic 1).

Polymerization-grade ethylene ($C_2$) was used and further purified by passing the gas through a series of columns: 500 cc Oxyclear cylinder from Labclear (Oakland, CA) followed by a 500 cc column packed with dried 3 Å molecular sieves (8-12 mesh; Aldrich Chemical Company) and a 500 cc column packed with dried 5 Å mole sieves (8-12 mesh; Aldrich Chemical Company).

Polymerization grade propylene ($C_3$) was used and further purified by passing it through a series of columns: 2,250 cc Oxiclear cylinder from Labclear followed by a 2,250 cc column packed with 3 Å mole sieves (8-12 mesh; Aldrich Chemical Company), then two 500 cc columns in series packed with 5 Å mole sieves (8-12 mesh; Aldrich Chemical Company), then a 500 cc column packed with Selexsorb CD (BASF), and finally a 500 cc column packed with Selexsorb COS (BASF).

Solutions of the metal complexes and activators were prepared in a drybox using toluene or methylcyclohexane. Concentrations were typically 0.2 mmol/L. Tri-n-octylaluminum (TNOAL, neat, AkzoNobel) was typically used as a scavenger. Concentration of the TNOAL solution in toluene ranged from 0.5 to 2.0 mmol/L.

Polymerizations were carried out in a parallel pressure reactor, as generally described in U.S. Pat. Nos. 6,306,658; 6,455,316; 6,489,168; WO 2000/009255; and Murphy, V. et al. (2003) “A Fully Integrated High-Throughput Screening Methodology for the Discovery of New Polyolefin Catalysts: Discovery of a New Class of High Temperature Single-Site Group (IV) Copolymerization Catalysts," *J. Am. Chem. Soc.*, v.125, pp. 4306-4317, each of which is fully incorporated herein by reference. The experiments were conducted in an inert atmosphere ($N_2$) drybox using autoclaves equipped with an external heater for temperature control, glass inserts (internal volume of reactor=23.5 mL for $C_2$ and $C_2/C_8$; 22.5 mL for $C_3$ runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours. Although the specific quantities, temperatures, solvents, reactants, reactant ratios, pressures, and other variables are frequently changed from one polymerization run to the next, the following describes a typical polymerization performed in a parallel pressure reactor.

Catalyst systems dissolved in solution were used in the polymerization examples below, unless specified otherwise.

Catalysts. Catalysts used in the polymerization examples below include metallocene and non-metallocene catalysts having the structures CAT-1-CAT-9 shown below.

CAT-1

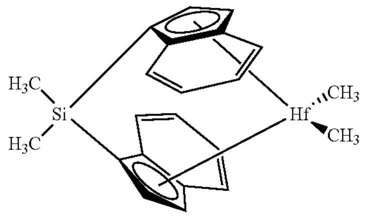

CAT-2

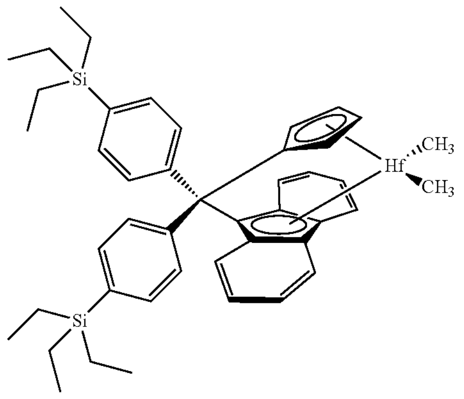

CAT-3

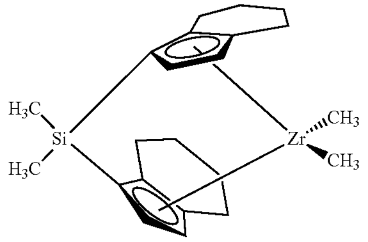

-continued

CAT-4

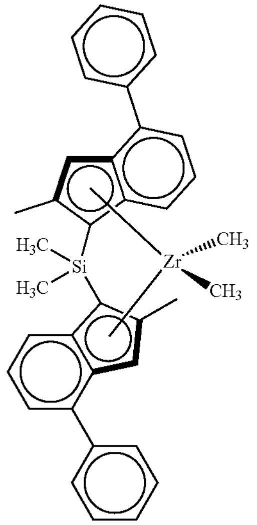

CAT-5

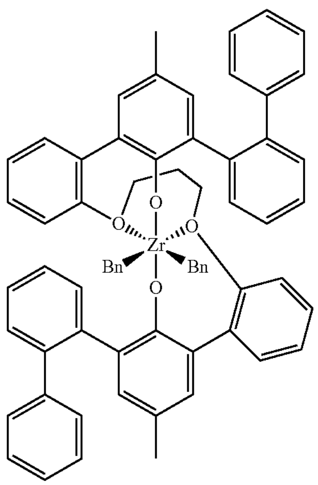

CAT-6

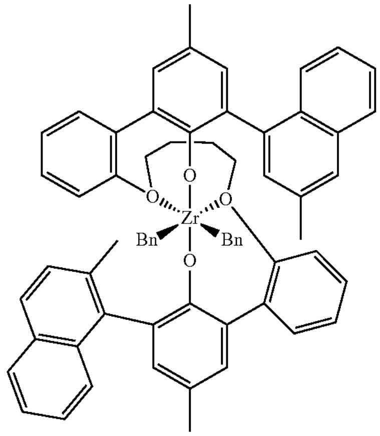

-continued

CAT-7

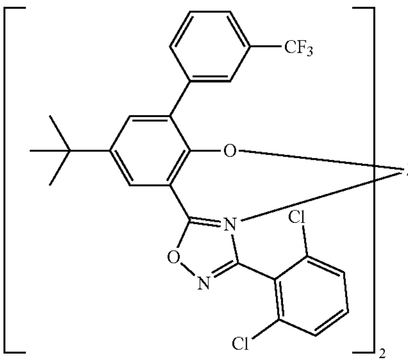

CAT-8

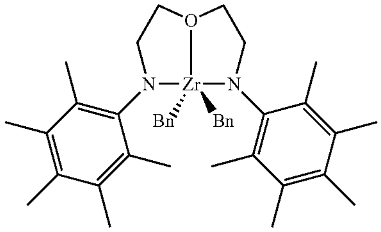

CAT-9

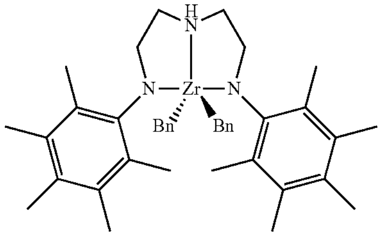

Ethylene-Octene Copolymerization (EO). A series of ethylene-octene polymerizations were performed in the parallel pressure reactor. In these studies catalysts were used along with ammonium borate activators. In a typical experiment an automated syringe 10 was used to introduce into the reactor the following reagents, if utilized, in the following order: isohexane (0.50 mL), 1-octene (100 μL), additional isohexane (0.50 mL), an isohexane solution of TNOAL scavenger injected into cells containing ammonium borate activators (0.005 M, 100 μL), additional isohexane (0.50 mL), a toluene solution of the respective polymerization catalyst (50 μL, 0.4 mM), additional isohexane (0.50 mL), a toluene solution of the respective activator (55 μL, 0.4 mM), then additional isohexane so that the total solvent volume for each run was 5 mL. Catalyst and ammonium borate activators were used in a 1:1.1 ratio. Each reaction was performed at a specified temperature range between 50 and 120° C., typically 100° C., while applying about 100 psig of ethylene (monomer) gas. Each reaction was allowed to run for about 20 minutes (~1,200 seconds) or until approximately 20 psig of ethylene gas uptake was observed, at which point the reactions were quenched with air (~300 psig). When sufficient polymer yield was attained (e.g., at least ~10 mg), the polyethylene product was analyzed by Rapid GPC, described below. Run conditions and data are reported in the Tables below.

Ethylene homopolymerization (PE). The parallel pressure reactor was prepared as described above and purged with ethylene. In these polymerizations a catalyst was used along with several different ammonium borate activators. The activators were prepared in solutions of toluene. Isohexane was then injected into each vessel at room temperature followed by ethylene gas. The reactor was heated to the set temperature while stirring at 800 rpm, and the scavenger, activator and catalyst solutions were injected sequentially to each vessel. The polymerization was allowed to proceed as described previously. Each reaction was allowed to run for about 20 minutes (~1,200 seconds) or until approximately 20 psig of ethylene gas uptake was observed. Run conditions and data are reported in the Tables below.

Propylene homopolymerization (PP). The parallel pressure reactor was prepared as described above and purged with propylene. In these polymerizations a catalyst was used along with several different ammonium borate activators. The activators were prepared in solutions of toluene. Isohexane was then injected into each vessel at room temperature followed by a predetermined amount of propylene gas. The reactor was heated to the set temperature while stirring at 800 rpm, and the scavenger, activator and catalyst solutions were injected sequentially to each vessel. The polymerization was allowed to proceed as described previously. Each reaction was allowed to run for about 20 minutes (~1,200 seconds) or until approximately 4 psig of propylene gas uptake was observed. Run conditions and data are reported in the Tables below.

Polymer Characterization. Polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference. This apparatus has a series of three 30 cm×7.5 mm linear columns, each containing PLgel 10 μm, Mix B. The GPC system was calibrated using polystyrene standards ranging from 580 to 3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.28 mg/mL and 400 uL of a polymer solution was injected into the system. The concentration of the polymer in the eluent was monitored using an evaporative light scattering detector. The molecular weights presented are relative to linear polystyrene standards and are uncorrected, unless indicated otherwise.

Differential Scanning Calorimetry (DSC—Procedure 1) measurements were performed on a TA-Q100 instrument to determine the melting point ($T_m$) of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period.

The weight percent of ethylene incorporated in polymers was determined by rapid FT-IR spectroscopy on a Bruker Equinox 55+IR in reflection mode. Samples were prepared in a thin film format by evaporative deposition techniques. FT-IR methods were calibrated using a set of samples with a range of known wt % ethylene content. For ethylene-1-octene copolymers, the wt % octene in the copolymer was determined via measurement of the methyl deformation band at ~1,375 $cm^{-1}$. The peak height of this band was normalized by the combination and overtone band at ~4,321 $cm^{-1}$, which corrects for path length differences.

Polymerization with CAT-1 Catalyst and C4 Activators

A series of polymerizations and co-polymerization were performed in parallel pressure reactors (PPRs) developed by Symyx Technologies, Inc. In these polymerizations, the metallocene rac-dimethylsilyl-bis(indenyl)hafnium dimethyl (CAT-1) was used along with several different ammonium borate activators. Polymerizations were performed at 100° C. and at 100 psi. The data and run conditions are shown in Tables 4-6.

TABLE 4

Data for the ethylene-octene copolymerization with CAT-1 catalyst and DMAH and C4 activators.

General conditions: CAT-1 = 20 nmol; activator = 22 nmol; 1-octene = 100 μL; solvent = isohexane; total volume = 5 mL; tri(n-octyl)aluminum = 500 nmol; T = 100° C.; P = 100 psi.

| Run | Activator | Time (s) | Yield (g) | Activity (kg/mmol * h) | Mw (g/mol) | Mn (g/mol) | PDI | Octene incorporation (wt %) | $T_m$ (° C.) |
|---|---|---|---|---|---|---|---|---|---|
| 1 | DMAH-A1 | 20.2 | 0.075 | 668 | 213,996 | 109,520 | 2.0 | 4.1 | 45.9 |
| 2 | DMAH-A1 | 18.3 | 0.070 | 689 | 203,689 | 118,987 | 1.7 | 31.9 | 45.0 |
| 3 | DMAH-A1 | 22.6 | 0.066 | 526 | 255,979 | 146,513 | 1.7 | 22.0 | 64.1 |
| 4 | DMAH-A1 | 25.6 | 0.051 | 359 | 292,671 | 148,073 | 2.0 | 25.7 | 73.0 |
| 5 | DMAH-A2 | 27.2 | 0.069 | 457 | 380,061 | 213,127 | 1.8 | 2.4 | 51.6 |
| 6 | DMAH-A2 | 27.9 | 0.065 | 419 | 384,224 | 222,601 | 1.7 | 28.2 | 56.1 |
| 7 | DMAH-A2 | 27.7 | 0.064 | 416 | 418,110 | 223,004 | 1.9 | 9.8 | 64.9 |
| 8 | DMAH-A2 | 29.4 | 0.059 | 361 | 456,087 | 246,798 | 1.8 | 21.6 | 73.2 |
| 9 | C4-A1 | 28.7 | 0.075 | 470 | 251,018 | 138,956 | 1.8 | 26.8 | 50.1 |
| 10 | C4-A1 | 21.0 | 0.063 | 540 | 260,449 | 132,173 | 2.0 | 29.5 | 55.6 |
| 11 | C4-A1 | 35.5 | 0.054 | 274 | 297,621 | 155,158 | 1.9 | 3.6 | 68.4 |
| 12 | C4-A1 | 32.9 | 0.057 | 312 | 350,734 | 181,401 | 1.9 | 16.0 | 77.7 |
| 13 | C4-A2 | 29.2 | 0.070 | 432 | 389,082 | 217,703 | 1.8 | 31.0 | 49.8 |
| 14 | C4-A2 | 26.7 | 0.066 | 445 | 442,184 | 259,415 | 1.7 | 27.8 | 59.0 |
| 15 | C4-A2 | 28.0 | 0.059 | 379 | 404,740 | 222,390 | 1.8 | 2.5 | 64.1 |
| 16 | C4-A2 | 40.9 | 0.056 | 246 | 481,914 | 260,788 | 1.8 | 22.7 | 69.1 |

FIG. 1 illustrates the differences in catalyst activity observed for the examples of Table 4.

TABLE 5

Data for the ethylene homopolymerization with CAT-1 catalyst and DMAH and C4 activators.
General conditions: CAT-1 = 20 nmol; activator = 22 nmol; solvent = isohexane; total volume = 5 mL; tri(n-octyl)aluminum = 500 nmol; T = 100° C.; P = 100 psi.

| Run | Activator | Time (s) | Yield (g) | Activity (kg/mmol *h) | Mw(g/mol) | Mn(g/mol) | PDI | $T_m$ (° C.) |
|---|---|---|---|---|---|---|---|---|
| 1 | DMAH-A1 | 24.6 | 0.052 | 380 | 532,719 | 259,194 | 2.1 | 134.7 |
| 2 | DMAH-A1 | 19.9 | 0.057 | 516 | 465,599 | 217,830 | 2.1 | 134.7 |
| 5 | DMAH-A1 | 20.2 | 0.051 | 454 | 496,760 | 224,010 | 2.2 | 134.4 |
| 6 | DMAH-A1 | 23.1 | 0.047 | 366 | 483,392 | 235,608 | 2.1 | 134.8 |
| 9 | DMAH-A2 | 46.6 | 0.065 | 251 | 691,837 | 362,479 | 1.9 | 134.5 |
| 10 | DMAH-A2 | 25.4 | 0.061 | 432 | 644,765 | 313,730 | 2.1 | 134.7 |
| 13 | DMAH-A2 | 22.4 | 0.055 | 442 | 511,907 | 248,632 | 2.1 | 134.9 |
| 14 | DMAH-A2 | 22.5 | 0.052 | 416 | 579,071 | 300,489 | 1.9 | 135.1 |
| 17 | C4-A1 | 34.2 | 0.059 | 311 | 622,243 | 314,097 | 2.0 | 134.6 |
| 18 | C4-A1 | 20.5 | 0.060 | 527 | 609,204 | 286,449 | 2.1 | 134.7 |
| 19 | C4-A1 | 20.7 | 0.047 | 409 | 493,438 | 255,849 | 1.9 | 134.7 |
| 20 | C4-A1 | 23.9 | 0.047 | 354 | 517,890 | 245,371 | 2.1 | 135.1 |
| 21 | C4-A2 | 40.0 | 0.061 | 275 | 708,758 | 347,116 | 2.0 | 135.2 |
| 22 | C4-A2 | 26.5 | 0.056 | 380 | 688,509 | 321,192 | 2.1 | 135.2 |
| 23 | C4-A2 | 22.7 | 0.053 | 420 | 641,058 | 315,285 | 2.0 | 135.4 |
| 24 | C4-A2 | 23.7 | 0.045 | 342 | 592,378 | 308,006 | 1.9 | 135.2 |

TABLE 6

Data for the propylene homopolymerization with CAT-1 catalyst and DMAH and C4 activators. General conditions: CAT-1 = 20 nmol; activator = 22 nmol; solvent = isohexane; total volume = 5 mL; tri(n-octyl)aluminum = 500 nmol; T = 100° C.; P = 100 psi.

| Run | Activator | Time (s) | Yield (g) | Activity (kg/mmol *h) | Mw (g/mol) | Mn (g/mol) | PDI | $T_m$ (° C.) |
|---|---|---|---|---|---|---|---|---|
| 1 | DMAH-A1 | 63.9 | 0.074 | 208 | 46,838 | 26,867 | 1.7 | 120 |
| 2 | DMAH-A1 | 84.4 | 0.083 | 177 | 53,488 | 33,956 | 1.6 | 115 |
| 3 | DMAH-A1 | 85.9 | 0.076 | 159 | 48,339 | 29,541 | 1.6 | 114 |
| 4 | DMAH-A1 | 114.5 | 0.069 | 108 | 58,165 | 36,066 | 1.6 | 122 |
| 5 | DMAH-A1 | 92.5 | 0.065 | 126 | 55,911 | 33,355 | 1.7 | 121 |
| 6 | DMAH-A1 | 102.3 | 0.056 | 99 | 51,967 | 26,257 | 2.0 | 121 |
| 7 | DMAH-A2 | 72.6 | 0.070 | 174 | 104,441 | 65,509 | 1.6 | 125 |
| 8 | DMAH-A2 | 100.7 | 0.068 | 122 | 117,743 | 73,932 | 1.6 | 126 |
| 9 | DMAH-A2 | 180.6 | 0.072 | 72 | 111,191 | 69,544 | 1.6 | 126 |
| 10 | DMAH-A2 | 133.7 | 0.065 | 88 | 114,496 | 65,644 | 1.7 | 126 |
| 11 | DMAH-A2 | 155.1 | 0.065 | 75 | 153,830 | 96,426 | 1.6 | 129 |
| 12 | DMAH-A2 | 458.3 | 0.052 | 20 | 124,708 | 74,048 | 1.7 | 126 |
| 13 | DMAH-A2 | 144.6 | 0.066 | 82 | 141,317 | 79,382 | 1.8 | 126 |
| 14 | DMAH-A2 | 107.7 | 0.061 | 102 | 127,730 | 78,854 | 1.6 | 127 |
| 15 | C4-A1 | 107.7 | 0.072 | 120 | 49,847 | 30,569 | 1.6 | 116 |
| 16 | C4-A1 | 104.3 | 0.072 | 124 | 50,940 | 31,673 | 1.6 | 115 |
| 17 | C4-A1 | 111 | 0.073 | 118 | 56,502 | 33,541 | 1.7 | 122 |
| 18 | C4-A1 | 158.4 | 0.053 | 60 | 54,221 | 33,643 | 1.6 | 115 |
| 19 | C4-A1 | 262.2 | 0.052 | 36 | 44,486 | 25,729 | 1.7 | 113 |
| 20 | C4-A1 | 121.9 | 0.068 | 100 | 55,056 | 34,151 | 1.6 | 115 |
| 21 | C4-A1 | 106.4 | 0.066 | 112 | 52,066 | 33,038 | 1.6 | 115 |
| 22 | C4-A1 | 133.1 | 0.057 | 77 | 59,804 | 38,114 | 1.6 | 117 |
| 23 | C4-A2 | 92.8 | 0.068 | 132 | 94,539 | 55,458 | 1.7 | 126 |
| 24 | C4-A2 | 146.9 | 0.060 | 74 | 104,303 | 63,437 | 1.6 | 126 |
| 25 | C4-A2 | 198.3 | 0.052 | 47 | 112,229 | 67,457 | 1.7 | 126 |
| 26 | C4-A2 | 164.9 | 0.058 | 63 | 111,252 | 71,031 | 1.6 | 126 |
| 27 | C4-A2 | 121.9 | 0.066 | 97 | 124,056 | 71,476 | 1.7 | 126 |
| 28 | C4-A2 | 130.3 | 0.057 | 79 | 116,560 | 71,581 | 1.6 | 126 |
| 29 | C4-A2 | 186.4 | 0.051 | 49 | 119,668 | 70,798 | 1.7 | 126 |
| 30 | C4-A2 | 214.7 | 0.047 | 39 | 137,381 | 86,735 | 1.6 | 127 |

Figure 2:
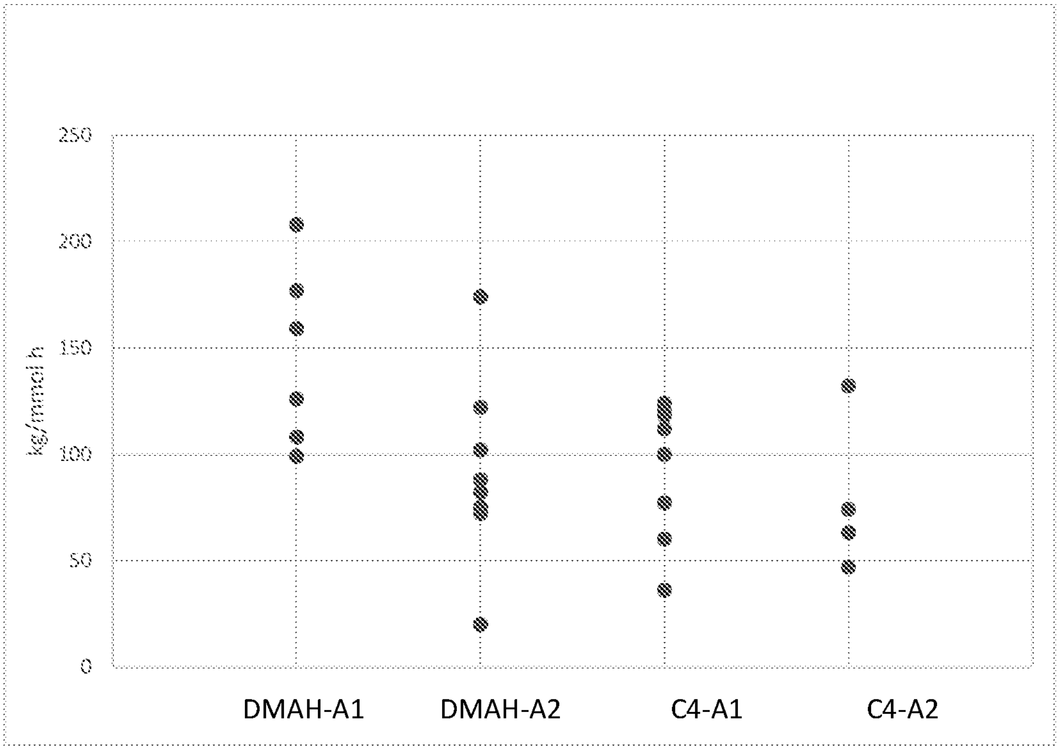
FIG. 2 is a graph illustrating the catalyst activity data for examples in Table 3.

FIG. 2 illustrates the differences in catalyst activity observed for the examples of Table 6.

Polymerization with CAT-2 Catalyst and C2 and C4 Activators

Another series of polymerizations and co-polymerization were performed. In these polymerizations, the catalyst used was CAT-2. Polymerizations were performed at 100° C. and at 100 psi. The data and run conditions are shown in Tables 7 and 8.

TABLE 7

Data for the ethylene-octene copolymerization with CAT-2 catalyst. General conditions: catalyst = 20 nmol; activator = 22 nmol; 1-octene = 100 μL; solvent = isohexane; total volume = 5 mL; tri(n-octyl)aluminum = 500 nmol; T = 100° C.; P = 100 psi.

| Run | Activator | Time (s) | Yield (g) | Activity (kg/mmol *h) | Mw(g/mol) | Mn(g/mol) | PDI | Octene incorporation (wt %) | $T_m$ (° C.) |
|---|---|---|---|---|---|---|---|---|---|
| 1 | DMAH-A1 | 49.8 | 0.080 | 289.2 | 775,794 | 405,592 | 1.9 | 45.3 | 47.5 |
| 2 | DMAH-A1 | 44.8 | 0.077 | 309.4 | 771,453 | 373,196 | 2.1 | 47.8 | 45.3 |
| 3 | DMAH-A1 | 38.9 | 0.073 | 337.8 | 841,312 | 413,308 | 2.0 | 38.5 | 49.8 |
| 4 | DMAH-A1 | 41.7 | 0.073 | 315.1 | 808,394 | 428,758 | 1.9 | 42.6 | 41.7 |
| 5 | DMAH-A1 | 39.8 | 0.067 | 303.0 | 924,538 | 427,211 | 2.2 | 34.2 | 48.1 |
| 6 | DMAH-A1 | 40.9 | 0.066 | 290.5 | 814,322 | 428,091 | 1.9 | 38.3 | 43.5 |
| 7 | DMAH-A1 | 45.6 | 0.067 | 264.5 | 878,150 | 444,480 | 2.0 | 35.1 | 58.1 |
| 8 | DMAH-A1 | 41.3 | 0.067 | 292.0 | 953,042 | 464,601 | 2.1 | 36.1 | 57.1 |
| 9 | C2-A1 | 60.0 | 0.061 | 183.0 | 817,235 | 430,336 | 1.9 | 43.9 | 46.4 |
| 10 | C2-A1 | 64.2 | 0.065 | 182.2 | 834,803 | 423,342 | 2.0 | 39.0 | 45.1 |
| 11 | C2-A1 | 51.5 | 0.060 | 209.7 | 950,536 | 446,763 | 2.1 | 37.6 | 50.1 |
| 12 | C2-A1 | 62.6 | 0.068 | 195.5 | 961,233 | 498,099 | 1.9 | 38.5 | 49.8 |
| 13 | C2-A1 | 61.7 | 0.061 | 178.0 | 999,210 | 491,800 | 2.0 | 41.3 | 51.0 |
| 14 | C2-A1 | 57.3 | 0.058 | 182.2 | 1,033,033 | 485,998 | 2.1 | 41.9 | 51.3 |
| 15 | C2-A1 | 71.9 | 0.049 | 122.7 | 1,224,276 | 609,743 | 2.0 | 32.4 | 60.4 |
| 16 | C2-A1 | 115.5 | 0.041 | 63.9 | 1,474,194 | 687,770 | 2.1 | 36.7 | 64.5 |
| 17 | C4-A1 | 55.0 | 0.074 | 242.2 | 824,626 | 393,843 | 2.1 | 44.1 | 42.0 |

TABLE 7-continued

Data for the ethylene-octene copolymerization with CAT-2 catalyst. General conditions: catalyst = 20 nmol; activator = 22 nmol; 1-octene = 100 μL; solvent = isohexane; total volume = 5 mL; tri(n-octyl)aluminum = 500 nmol; T = 100° C.; P = 100 psi.

| Run | Activator | Time (s) | Yield (g) | Activity (kg/mmol *h) | Mw(g/mol) | Mn(g/mol) | PDI | Octene incorporation (wt %) | $T_m$ (° C.) |
|---|---|---|---|---|---|---|---|---|---|
| 18 | C4-A1 | 51.9 | 0.077 | 267.1 | 856,979 | 417,154 | 2.1 | 40.3 | 46.9 |
| 19 | C4-A1 | 51.2 | 0.070 | 246.1 | 857,482 | 395,944 | 2.2 | 42.6 | 48.6 |
| 20 | C4-A1 | 43.4 | 0.065 | 269.6 | 899,535 | 476,742 | 1.9 | 39.1 | 49.1 |
| 21 | C4-A1 | 49.2 | 0.058 | 212.2 | 847,615 | 431,219 | 2.0 | 36.9 | 50.0 |
| 22 | C4-A1 | 44.8 | 0.064 | 257.1 | 892,636 | 464,593 | 1.9 | 55.1 | 52.6 |
| 23 | C4-A1 | 46.1 | 0.063 | 246.0 | 918,951 | 463,658 | 2.0 | 35.4 | 61.3 |
| 24 | C4-A1 | 44.3 | 0.061 | 247.9 | 952,051 | 467,974 | 2.0 | 37.4 | 54.4 |

The control conditions using CAT-2 and DMAH-A1 in runs 1-8 yield high Mw polymer (846,000±67,000 g/mol) with a high percent of octene incorporation (39.7±5.0 wt %), with a high degree of error across the replicates. The control conditions in runs 1-8 also produce polymer with an activity of 300.1±21.7 kg/mmol*hr. As seen in runs 9-24, the catalyst systems using activators C2-A1 and C4-A1 produce polymer at a lower activity, 164.7 kg/(mmol*hr) and 248.5 kg/(mmol*hr), respectively. However, the polymers produced by the C2-A1 system do vary. The polymer molecular weight is higher at 1,037,000±217,000 g/mol, but poor reproducibility between cells prevents this from being significantly different. The polymers produced by C4-A1 are consistent with those produced by the control system, with similar Mw, % octene incorporation and $T_m$.

TABLE 8

Data for the ethylene homopolymerization with CAT-2 catalyst. General conditions: catalyst = 20 nmol; activator = 22 nmol; solvent = isohexane; total volume = 5 mL; tri(n-octyl)aluminum = 500 nmol; T = 100° C.; P = 100 psi.

| Run | Activator | Time (s) | Yield (g) | Activity (kg/mmol *h) | Mw (g/mol) | Mn (g/mol) | PDI | $T_m$ (° C.) |
|---|---|---|---|---|---|---|---|---|
| 1 | DMAH-A1 | 136.0 | 0.063 | 83.4 | 1,927,117 | 637,816 | 3.0 | 133.0 |
| 2 | DMAH-A1 | 134.7 | 0.067 | 89.5 | 1,925,977 | 709,329 | 2.7 | 133.1 |
| 3 | DMAH-A1 | 39.3 | 0.061 | 279.4 | 1,646,320 | 604,603 | 2.7 | 132.8 |
| 4 | DMAH-A1 | 88.2 | 0.065 | 132.7 | 1,866,168 | 674,941 | 2.8 | 133.1 |
| 5 | DMAH-A1 | 19.0 | 0.054 | 511.6 | 1,632,842 | 615,080 | 2.7 | 132.9 |
| 6 | DMAH-A1 | 26.5 | 0.055 | 373.6 | 1,681,747 | 654,660 | 2.6 | 132.6 |
| 7 | DMAH-A1 | 27.9 | 0.056 | 361.3 | 1,789,786 | 635,288 | 2.8 | 133.0 |
| 8 | DMAH-A1 | 30.8 | 0.055 | 321.4 | 1,643,106 | 591,994 | 2.8 | 132.8 |
| 9 | C2-A1 | 104.0 | 0.061 | 105.6 | 1,991,575 | 727,165 | 2.7 | 133.7 |
| 10 | C2-A1 | 134.5 | 0.054 | 72.3 | 1,921,683 | 673,422 | 2.9 | 133.1 |
| 11 | C2-A1 | 104.1 | 0.055 | 95.1 | 2,009,485 | 699,144 | 2.9 | 133.3 |
| 12 | C2-A1 | 70.1 | 0.054 | 138.7 | 1,909,002 | 663,731 | 2.9 | 133.3 |
| 13 | C2-A1 | 74.7 | 0.050 | 120.5 | 2,075,255 | 784,378 | 2.6 | 133.6 |
| 14 | C2-A1 | 60.6 | 0.048 | 142.6 | 2,143,453 | 811,357 | 2.6 | 133.5 |
| 15 | C2-A1 | 38.8 | 0.047 | 218.0 | 1,934,248 | 749,646 | 2.6 | 133.4 |
| 16 | C2-A1 | 30.2 | 0.049 | 292.1 | 1,846,193 | 803,119 | 2.3 | 133.4 |

As shown in Tables 7 and 8, changing the anilinium borate has minimal effect on the activity of the catalysts, given the margin of error in the reproducibility between cells. High molecular weight polyethylene was produced by all systems, with consistent melting points between 132.8-133.7° C. The polymers produced by the catalyst system containing C2-A1 did produce polymer with higher molecular weight (1,963,000±97,000 g/mol) than DMAH-A1 (1,764,000±129,000).

Polymerization with CAT-1 and CAT-2 Catalysts and C3 Activators

Another series of co-polymerization reactions were performed in parallel pressure reactors. In these polymerizations, CAT-1 and CAT-2 were used along with DMAH-A1, DMAH-A2, C3-A1, and C3-A2 activators. Polymerizations were performed at 100° C. and at 100 psi. The data and run conditions are shown in Table 9.

TABLE 9

Data for the ethylene-octene copolymerization with CAT-1 and CAT-2 catalysts and C3 activators. General conditions: catalyst = 20 nmol; activator = 22 nmol; 1-octene = 100 μL; solvent = isohexane; total volume = 5 mL; tri(n-octyl)aluminum = 500 nmol; T = 100° C.; P = 100 psi.

| Run | Catalyst | Activator | Time (s) | Yield (g) | Activity (kg/mmol *h) | Mw (g/mol) | Mn (g/mol) | PDI | Octene incorp. (wt %) | $T_m$ (° C.) |
|---|---|---|---|---|---|---|---|---|---|---|
| 1 | CAT-1 | DMAH-A1 | 35.2 | 0.094 | 480.7 | 192,596 | 94,141 | 2.0 | 32.8 | 52.6 |
| 2 | CAT-1 | DMAH-A1 | 36.4 | 0.094 | 464.8 | 214,142 | 117,365 | 1.8 | 28.2 | 47.4 |
| 3 | CAT-1 | DMAH-A1 | 36.7 | 0.093 | 456.1 | 210,944 | 111,186 | 1.9 | 33.0 | 51.1 |
| 4 | CAT-1 | DMAH-A1 | 40.9 | 0.073 | 321.3 | 235,202 | 131,832 | 1.8 | 27.9 | 51.1 |
| 5 | CAT-1 | DMAH-A1 | 42.1 | 0.075 | 320.7 | 233,765 | 134,563 | 1.7 | 27.4 | 51.1 |
| 6 | CAT-1 | DMAH-A1 | 38.0 | 0.080 | 378.9 | 244,784 | 133,194 | 1.8 | 27.3 | 51.6 |
| 7 | CAT-1 | DMAH-A2 | 59.0 | 0.090 | 274.6 | 411,588 | 246,908 | 1.7 | 33.8 | 48.3 |
| 8 | CAT-1 | DMAH-A2 | 48.8 | 0.089 | 328.3 | 381,164 | 204,945 | 1.9 | 30.4 | 49.1 |
| 9 | CAT-1 | DMAH-A2 | 58.4 | 0.085 | 262.0 | 429,142 | 253,575 | 1.7 | 25.8 | 54.1 |
| 10 | CAT-1 | DMAH-A2 | 56.6 | 0.073 | 232.2 | 422,975 | 236,884 | 1.8 | 25.0 | 64.6 |
| 11 | CAT-1 | DMAH-A2 | 57.5 | 0.073 | 228.5 | 394,834 | 220,091 | 1.8 | 28.1 | 64.8 |
| 12 | CAT-1 | DMAH-A2 | 60.1 | 0.078 | 233.6 | 433,538 | 245,158 | 1.8 | 27.7 | 65.1 |
| 13 | CAT-1 | C3-A1 | 95.5 | 0.065 | 122.5 | 455,168 | 281,144 | 1.6 | 26.6 | 57.7 |
| 14 | CAT-1 | C3-A1 | 65.6 | 0.073 | 200.3 | 435,483 | 284,140 | 1.5 | 29.6 | 54.1 |
| 15 | CAT-1 | C3-A1 | 89.9 | 0.066 | 132.1 | 439,034 | 264,123 | 1.7 | 28.7 | 61.0 |
| 16 | CAT-1 | C3-A1 | 80.2 | 0.056 | 125.7 | 465,712 | 294,010 | 1.6 | 22.8 | 66.8 |
| 17 | CAT-1 | C3-A1 | 89.2 | 0.062 | 125.1 | 480,276 | 300,886 | 1.6 | 25.4 | 64.2 |
| 18 | CAT-1 | C3-A1 | 86.8 | 0.061 | 126.5 | 462,905 | 263,614 | 1.8 | 25.6 | 68.4 |
| 19 | CAT-1 | C3-A2 | 32.6 | 0.082 | 452.8 | 243,620 | 130,811 | 1.9 | 26.1 | 43.9 |
| 20 | CAT-1 | C3-A2 | 32.8 | 0.078 | 428.0 | 230,022 | 124,994 | 1.8 | 26.0 | 52.5 |
| 21 | CAT-1 | C3-A2 | 51.2 | 0.069 | 242.6 | 234,078 | 123,154 | 1.9 | 29.0 | 52.5 |
| 22 | CAT-1 | C3-A2 | 53.0 | 0.059 | 200.4 | 288,673 | 163,814 | 1.8 | 26.9 | 65.6 |
| 23 | CAT-1 | C3-A2 | 48.6 | 0.064 | 237.0 | 275,518 | 159,138 | 1.7 | 23.0 | 73.6 |
| 24 | CAT-1 | C3-A2 | 54.9 | 0.057 | 186.9 | 319,028 | 188,576 | 1.7 | 22.7 | 73.2 |
| 25 | CAT-2 | DMAH-A1 | 107.2 | 0.115 | 193.1 | 498,194 | 281,772 | 1.8 | 30.0 | 45.0 |
| 26 | CAT-2 | DMAH-A1 | 97.5 | 0.109 | 201.2 | 501,738 | 250,685 | 2.0 | 26.9 | 42.5 |
| 27 | CAT-2 | DMAH-A1 | 125.4 | 0.083 | 119.1 | 507,170 | 266,208 | 1.9 | 36.3 | 41.7 |
| 28 | CAT-2 | DMAH-A1 | 66.9 | 0.088 | 236.8 | 584,331 | 343,326 | 1.7 | 21.1 | 52.0 |
| 29 | CAT-2 | DMAH-A1 | 64.7 | 0.086 | 239.3 | 633,457 | 386,529 | 1.6 | 26.3 | 50.9 |
| 30 | CAT-2 | DMAH-A1 | 67.3 | 0.091 | 243.4 | 572,412 | 350,261 | 1.6 | 26.5 | 48.6 |
| 31 | CAT-2 | DMAH-A2 | 152.8 | 0.104 | 122.5 | 653,484 | 388,460 | 1.7 | 22.9 | 46.4 |
| 32 | CAT-2 | DMAH-A2 | 139.5 | 0.100 | 129.0 | 660,990 | 414,456 | 1.6 | 30.6 | 47.6 |
| 33 | CAT-2 | DMAH-A2 | 123.7 | 0.100 | 145.5 | 674,729 | 425,966 | 1.6 | 31.2 | 49.9 |
| 34 | CAT-2 | DMAH-A2 | 90.4 | 0.082 | 163.3 | 886,907 | 485,220 | 1.8 | 32.7 | 53.6 |
| 35 | CAT-2 | DMAH-A2 | 88.9 | 0.079 | 160.0 | 958,500 | 518,492 | 1.8 | 25.3 | 56.3 |
| 36 | CAT-2 | DMAH-A2 | 137.8 | 0.070 | 91.4 | 1,151,409 | 608,277 | 1.9 | 22.3 | 60.3 |
| 37 | CAT-2 | C3-A1 | 679.4 | 0.051 | 13.5 | 1,147,654 | 759,768 | 1.5 | 27.6 | 55.9 |
| 38 | CAT-2 | C3-A1 | 162.7 | 0.085 | 94.0 | 834,167 | 521,799 | 1.6 | 38.5 | 51.0 |
| 39 | CAT-2 | C3-A1 | 166.2 | 0.088 | 95.3 | 936,155 | 499,958 | 1.9 | 26.8 | 52.9 |
| 40 | CAT-2 | C3-A1 | 121.1 | 0.064 | 95.1 | 1,415,697 | 749,558 | 1.9 | 26.2 | 66.4 |
| 41 | CAT-2 | C3-A1 | 119.7 | 0.063 | 94.7 | 1,352,756 | 717,543 | 1.9 | 25.5 | 66.8 |
| 42 | CAT-2 | C3-A1 | 207.4 | 0.055 | 47.7 | 1,305,524 | 724,244 | 1.8 | 24.7 | 67.6 |
| 43 | CAT-2 | C3-A2 | 77.5 | 0.087 | 202.1 | 601,982 | 343,238 | 1.8 | 27.4 | 48.3 |
| 44 | CAT-2 | C3-A2 | 77.8 | 0.087 | 201.3 | 629,767 | 382,184 | 1.6 | 30.8 | 49.8 |
| 45 | CAT-2 | C3-A2 | 92.5 | 0.088 | 171.2 | 677,442 | 394,428 | 1.7 | 26.0 | 52.5 |
| 46 | CAT-2 | C3-A2 | 76.9 | 0.071 | 166.2 | 820,686 | 445,414 | 1.8 | 25.2 | 72.7 |

In runs 1-46 of Table 9, four activators were tested with two catalysts. Generally, the activities of the comparative activators show that DMAH-A1 operates at higher values than DMAH-A2, as seen here. However, the experimental C3-A1 operated at a lower rate than C3-A2. The activity values were higher overall for the CAT-1 catalyst versus CAT-2.

For the molecular weight, opposite trends were also seen versus the trends from the comparative activators. Higher molecular weight polymers were produced by the DMAH-A2 activator vs DMAH-A1. However, higher molecular weight polymers were produced by C3-A1 activator vs C3-A2. Comparing the two catalysts, CAT-1 produced lower molecular weight polymers, with a more narrow distribution. CAT-2 produced higher molecular weight polymers, with a large standard deviation.

The octene incorporation was not affected by the anilinium or borate component of the activator, or by the catalyst. Average incorporation values ranged from 25.6-29.4 wt %.

Large standard deviation prevented any further conclusions. Melting points generally agreed with trends in molecular weight and comonomer incorporation.

Polymerization with CAT-1 and CAT-2 Catalysts and C1 Activators

Another series of co-polymerization were performed in parallel pressure reactors. In these polymerizations, CAT-1 and CAT-2 were used along with DMAH-A1, DMAH-A2, C1-A1, and C1-A2 activators. Polymerizations were performed at 100° C. and at 100 psi. The data and run conditions are shown in Table 10.

TABLE 10

Data for the ethylene-octene copolymerization with CAT-1 and CAT-2 catalysts and C1 activators. General conditions: catalyst = 20 nmol; activator = 22 nmol; 1-octene = 100 μL; solvent = isohexane; total volume = 5 mL; tri(n-octyl)aluminum = 500 nmol; T = 100° C.; P = 100 psi.

| Run | Catalyst | Activator | Time (s) | Yield (g) | Activity (kg/mmol *h) | Mw (g/mol) | Mn (g/mol) | PDI | Octene incorp. (wt %) | $T_m$ (° C.) |
|---|---|---|---|---|---|---|---|---|---|---|
| 1 | CAT-1 | DMAH-A1 | 1200 | 0.034 | 4.6 | 350,380 | 197,686 | 1.8 | 27.3 | 62.0 |
| 2 | CAT-1 | DMAH-A1 | 50.8 | 0.078 | 251.3 | 234,263 | 137,028 | 1.7 | 33.4 | 50.9 |
| 3 | CAT-1 | DMAH-A1 | 33.6 | 0.086 | 418.8 | 238,364 | 135,434 | 1.8 | 34.6 | 52.6 |
| 4 | CAT-1 | DMAH-A1 | 36.8 | 0.081 | 360.2 | 224,314 | 135,233 | 1.7 | 32.7 | 51.8 |
| 5 | CAT-1 | DMAH-A2 | 69.5 | 0.083 | 195.4 | 444,769 | 246,674 | 1.8 | 29.7 | 60.2 |
| 6 | CAT-1 | DMAH-A2 | 46.9 | 0.092 | 321.0 | 440,392 | 232,492 | 1.9 | 31.5 | 57.5 |
| 7 | CAT-1 | DMAH-A2 | 45.5 | 0.078 | 280.5 | 419,488 | 237,192 | 1.8 | 27.3 | 60.5 |
| 8 | CAT-1 | DMAH-A2 | 53.8 | 0.074 | 225.1 | 432,075 | 229,916 | 1.9 | 30.0 | 63.0 |
| 9 | CAT-1 | C1-A1 | 70.5 | 0.071 | 164.8 | 346,594 | 183,899 | 1.9 | 26.5 | 62.0 |
| 10 | CAT-1 | C1-A1 | 73.6 | 0.073 | 162.3 | 345,264 | 181,600 | 1.9 | 31.8 | 61.8 |
| 11 | CAT-1 | C1-A1 | 50.1 | 0.070 | 228.6 | 284,404 | 160,300 | 1.8 | 28.1 | 63.3 |
| 12 | CAT-1 | C1-A1 | 81.2 | 0.055 | 110.8 | 356,041 | 191,165 | 1.9 | 27.3 | 66.6 |
| 13 | CAT-1 | C1-A2 | 52.7 | 0.099 | 307.4 | 403,522 | 215,897 | 1.9 | 30.3 | 51.9 |
| 14 | CAT-1 | C1-A2 | 51.8 | 0.094 | 296.9 | 406,578 | 216,145 | 1.9 | 33.2 | 51.6 |
| 15 | CAT-1 | C1-A2 | 52.0 | 0.080 | 251.7 | 459,433 | 261,309 | 1.8 | 28.9 | 64.3 |
| 16 | CAT-1 | C1-A2 | 82.0 | 0.069 | 137.7 | 540,865 | 291,887 | 1.9 | 29.3 | 63.9 |
| 17 | CAT-2 | DMAH-A1 | 83.0 | 0.098 | 193.2 | 785,913 | 419,575 | 1.9 | 32.1 | 46.2 |
| 18 | CAT-2 | DMAH-A1 | 73.4 | 0.100 | 222.9 | 831,419 | 401,732 | 2.1 | 33.3 | 50.4 |
| 19 | CAT-2 | DMAH-A1 | 74.9 | 0.087 | 190.1 | 934,650 | 485,078 | 1.9 | 30.6 | 55.2 |
| 20 | CAT-2 | DMAH-A1 | 74.8 | 0.071 | 155.3 | 1,266,033 | 748,671 | 1.7 | 25.7 | 69.1 |
| 21 | CAT-2 | DMAH-A2 | 123.8 | 0.100 | 132.2 | 1,005,907 | 490,419 | 2.1 | 32.2 | 48.7 |
| 22 | CAT-2 | DMAH-A2 | 74.5 | 0.089 | 195.5 | 1,231,977 | 643,294 | 1.9 | 30.1 | 55.7 |
| 23 | CAT-2 | DMAH-A2 | 82.4 | 0.078 | 154.9 | 1,107,697 | 612,652 | 1.8 | 33.5 | 52.9 |
| 24 | CAT-2 | DMAH-A2 | 76.1 | 0.074 | 159.1 | 1,495,045 | 854,710 | 1.7 | 25.8 | 71.1 |
| 25 | CAT-2 | C1-A1 | 117.1 | 0.095 | 132.8 | 908,017 | 463,412 | 2.0 | 31.0 | 50.6 |
| 26 | CAT-2 | C1-A1 | 91.6 | 0.089 | 159.0 | 962,042 | 522,663 | 1.8 | 34.2 | 52.9 |
| 27 | CAT-2 | C1-A1 | 78.7 | 0.081 | 168.4 | 912,319 | 488,200 | 1.9 | 32.4 | 51.5 |
| 28 | CAT-2 | C1-A1 | 89.4 | 0.078 | 142.8 | 1,022,942 | 578,917 | 1.8 | 32.2 | 65.5 |
| 29 | CAT-2 | C1-A2 | 104.4 | 0.092 | 144.2 | 1,075,652 | 467,189 | 2.3 | 34.0 | 50.1 |
| 30 | CAT-2 | C1-A2 | 92.7 | 0.085 | 150.0 | 1,112,592 | 623,523 | 1.8 | 35.8 | 51.3 |
| 31 | CAT-2 | C1-A2 | 100.9 | 0.077 | 124.9 | 1,238,603 | 615,679 | 2.0 | 28.0 | 66.6 |
| 32 | CAT-2 | C1-A2 | 85.7 | 0.075 | 143.2 | 1,413,690 | 795,868 | 1.8 | 25.2 | 69.5 |

Table 10 shows that the activity values for the experimental C1 activators (runs 9-16 and 25-32) were similar to that of the comparative DMAH examples (runs 1-8 and 17-24). Polymer molecular weights followed general trends, with the activators containing the BF28 borate producing polymers of slightly higher molecular weight. Comonomer incorporation was not affected by activator or catalyst, with average octene incorporation around 30 wt %. The standard deviation in melt temperatures between polymers produced by the CAT-2 catalysts systems prevented any conclusions from being drawn. For polymers produced by CAT-1, melt temperature followed trends in molecular weight.

Polymerization with CAT-3 Catalyst and C4 Activators

Another series of propylene homopolymerization reactions were performed in parallel pressure reactors. In these polymerizations, CAT-3 and OMC1 were used as catalysts. DMAH-A1, C4-A1, and M2HTH-A1 (di(hydrogenated tallow)methylamine-BF20) were uses as activators. Polymerizations were performed at 100° C. and at 160 psi. The data and run conditions are shown in Table 11.

TABLE 11

Data for the propylene homopolymerization. General conditions: catalyst = 20 nmol; activator = 22 nmol; solvent = isohexane; total volume = 5 mL; tri(n-octyl)aluminum = 500 nmol; T = 100° C.; P = 160 psi

| Run | Catalyst | Activator | Time (s) | Yield (g) | activity (kg/mmol *h) | Mw (g/mol) | Mn (g/mol) | PDI |
|---|---|---|---|---|---|---|---|---|
| 1 | OMC1 | DMAH-A1 | 1200 | 0.022 | 3.3 | 48,228 | 32,094 | 1.5 |
| 2 | OMC1 | DMAH-A1 | 189.8 | 0.040 | 37.9 | 48,767 | 30,962 | 1.6 |
| 3 | OMC1 | DMAH-A1 | 1201 | 0.036 | 5.4 | 49,986 | 28,587 | 1.7 |
| 4 | OMC1 | DMAH-A1 | 298.9 | 0.052 | 31.3 | 51,811 | 31,509 | 1.6 |
| 5 | OMC1 | DMAH-A1 | 184.3 | 0.049 | 47.9 | 57,979 | 33,083 | 1.8 |
| 6 | OMC1 | DMAH-A1 | 1201 | 0.040 | 6.0 | 55,872 | 33,487 | 1.7 |
| 7 | OMC1 | C4-A1 | 98.4 | 0.077 | 140.9 | 42,175 | 22,671 | 1.9 |
| 8 | OMC1 | C4-A1 | 103.8 | 0.075 | 130.1 | 51,745 | 25,808 | 2.0 |
| 9 | OMC1 | C4-A1 | 123.8 | 0.071 | 103.2 | 45,604 | 26,688 | 1.7 |
| 10 | OMC1 | C4-A1 | 121.3 | 0.065 | 96.5 | 47,522 | 28,748 | 1.7 |
| 11 | OMC1 | C4-A1 | 98.1 | 0.067 | 122.9 | 46,284 | 29,836 | 1.6 |
| 12 | OMC1 | C4-A1 | 108.0 | 0.066 | 110.0 | 50,921 | 30,560 | 1.7 |
| 13 | OMC1 | M2HTH-A1 | 255.4 | 0.050 | 35.2 | 45,424 | 28,479 | 1.6 |

TABLE 11-continued

Data for the propylene homopolymerization.
General conditions: catalyst = 20 nmol; activator = 22 nmol; solvent = isohexane; total volume = 5 mL; tri(n-octyl)aluminum = 500 nmol; T = 100° C.; P = 160 psi

| Run | Catalyst | Activator | Time (s) | Yield (g) | activity (kg/mmol *h) | Mw (g/mol) | Mn (g/mol) | PDI |
|---|---|---|---|---|---|---|---|---|
| 14 | OMC1 | M2HTH-A1 | 228.6 | 0.051 | 40.2 | 46,646 | 27,437 | 1.7 |
| 15 | OMC1 | M2HTH-A1 | 260.1 | 0.041 | 28.4 | 51,033 | 27,801 | 1.8 |
| 16 | OMC1 | M2HTH-A1 | 192.2 | 0.041 | 38.4 | 51,515 | 33,161 | 1.6 |
| 17 | OMC1 | M2HTH-A1 | 195.2 | 0.035 | 32.3 | 50,007 | 30,853 | 1.6 |
| 18 | OMC1 | M2HTH-A1 | 209.7 | 0.039 | 33.5 | 53,376 | 34,611 | 1.5 |
| 19 | CAT-3 | DMAH-A1 | 238.3 | 0.031 | 23.4 | 512 | 384 | 1.3 |
| 20 | CAT-3 | DMAH-A1 | 344.1 | 0.023 | 12.0 | 481 | 365 | 1.3 |
| 21 | CAT-3 | DMAH-A1 | 1201 | 0.011 | 1.6 | 480 | 365 | 1.3 |
| 22 | CAT-3 | DMAH-A1 | 443.1 | 0.026 | 10.6 | 452 | 354 | 1.3 |
| 23 | CAT-3 | DMAH-A1 | 274.4 | 0.029 | 19.0 | 507 | 381 | 1.3 |
| 24 | CAT-3 | DMAH-A1 | 382.6 | 0.029 | 13.6 | 494 | 363 | 1.4 |
| 25 | CAT-3 | C4-A1 | 128.9 | 0.052 | 72.6 | 442 | 335 | 1.3 |
| 26 | CAT-3 | C4-A1 | 108.9 | 0.051 | 84.3 | 472 | 342 | 1.4 |
| 27 | CAT-3 | C4-A1 | 143.8 | 0.040 | 50.1 | 492 | 358 | 1.4 |
| 28 | CAT-3 | C4-A1 | 96.7 | 0.051 | 94.9 | 456 | 351 | 1.3 |
| 29 | CAT-3 | C4-A1 | 112.1 | 0.048 | 77.1 | 495 | 363 | 1.4 |
| 30 | CAT-3 | C4-A1 | 112.4 | 0.054 | 86.5 | 488 | 354 | 1.4 |
| 31 | CAT-3 | M2HTH-A1 | 126.2 | 0.046 | 65.6 | 458 | 343 | 1.3 |
| 32 | CAT-3 | M2HTH-A1 | 149.2 | 0.046 | 55.5 | 508 | 362 | 1.4 |
| 33 | CAT-3 | M2HTH-A1 | 176.4 | 0.043 | 43.9 | 492 | 363 | 1.4 |

Polymerization with CAT-4 Catalyst and C4-A2 Activator

Another series of propylene homopolymerization reactions were performed in parallel pressure reactors. In these polymerizations, CAT-4 was used as catalyst. DMAH-A2 and C4-A2 was used as activator. Polymerizations were performed at 100° C. and at 160 psi. The data and run conditions are shown in Table 12.

TABLE 12

Data for the propylene homopolymerization with CAT-4 catalyst and DMAH-A2 and C4 activators.
General conditions: catalyst = 20 nmol; activator = 22 nmol; solvent = isohexane; total volume = 5 mL; tri(n-octyl)aluminum = 500 nmol; T = 100° C.; P = 160 psi.

| Run | Activator | Time (s) | Yield (g) | Activity (kg/mmol/h) | Mw (g/mol) | Mn (g/mol) | PDI | $T_m$ (° C.) |
|---|---|---|---|---|---|---|---|---|
| 1 | DMAH-A2 | 42.7 | 0.132 | 556 | 100,439 | 54,510 | 1.8 | 151.6 |
| 2 | DMAH-A2 | 46.7 | 0.138 | 532 | 100,053 | 54,548 | 1.8 | 151.0 |
| 3 | DMAH-A2 | 36.8 | 0.160 | 783 | 112,539 | 57,992 | 1.9 | 150.4 |
| 4 | DMAH-A2 | 38.8 | 0.142 | 659 | 111,994 | 63,777 | 1.8 | 150.3 |
| 5 | C4-A2 | 39.9 | 0.168 | 758 | 95,401 | 46,167 | 2.1 | 149.3 |
| 6 | C4-A2 | 34.2 | 0.157 | 826 | 93,988 | 47,651 | 2.0 | 148.7 |
| 7 | C4-A2 | 41.6 | 0.153 | 662 | 81,793 | 39,753 | 2.1 | 148.3 |
| 8 | C4-A2 | 35.8 | 0.176 | 885 | 97,534 | 46,457 | 2.1 | 149.2 |

Changing the anilinium borate has minimal effect on the activity of the catalysts. Changing the borate also insignificantly affected the polymers produced in terms of molecular weight, PDI and melting point. The catalyst produced low molecular weight polypropylene (20K-30K g/mol).

Polymerization with CAT-5 and CAT-6 Catalysts and C2 and C4 Activators

Another series of ethylene-octene copolymerization reactions were performed in parallel pressure reactors. In these polymerizations, CAT-5 and CAT-6 were used as catalysts. Polymerizations were performed at 100° C. and at 100 psi. The data and run conditions are shown in Table 13.

TABLE 13

Data for the ethylene-octene copolymerization with CAT-5 and CAT-6 catalysts. General conditions: catalyst = 20 nmol; ammonium borate activator = 22 nmol; MAO activator = 10,000 nmol; 1-octene = 100 μL; solvent = isohexane; total volume = 5 mL; tri(n-octyl)aluminum = 500 nmol; T = 100° C.; P = 100 psi.

| Run | Catalyst | Activator | Time (s) | Yield (g) | Activity (kg/ mmol/h) | Mw (g/mol) | Mn (g/mol) | PDI | Octene incorp. (wt %) | $T_m$ (° C.) |
|---|---|---|---|---|---|---|---|---|---|---|
| 1 | CAT-5 | DMAH-A1 | 1201 | 0.012 | 2.1 | 320,021 | 186,762 | 1.7 | 8.4 | 109.8 |
| 2 | CAT-5 | DMAH-A1 | 1200 | 0.009 | 1.6 | — | — | — | — | — |
| 3 | CAT-5 | DMAH-A1 | 1200 | 0.006 | 1.1 | — | — | — | — | — |
| 4 | CAT-5 | DMAH-A1 | 1201 | 0.006 | 1.1 | — | — | — | — | — |
| 5 | CAT-5 | DMAH-A2 | 1201 | 0.013 | 2.3 | 322,584 | 192,154 | 1.7 | 8.6 | 107.5 |
| 6 | CAT-5 | DMAH-A2 | 1200 | 0.009 | 1.6 | — | — | — | — | — |
| 7 | CAT-5 | DMAH-A2 | 1201 | 0.007 | 1.2 | — | — | — | — | — |
| 8 | CAT-5 | DMAH-A2 | 1200 | 0.005 | 0.9 | — | — | — | — | — |
| 9 | CAT-5 | C4-A1 | 1200 | 0.008 | 1.4 | — | — | — | — | — |
| 10 | CAT-5 | C4-A1 | 1201 | 0.008 | 1.4 | — | — | — | — | — |
| 11 | CAT-5 | C4-A1 | 1201 | 0.006 | 1.1 | — | — | — | — | — |
| 12 | CAT-5 | C4-A1 | 1200 | 0.006 | 1.1 | — | — | — | — | — |
| 13 | CAT-5 | C4-A2 | 1200 | 0.012 | 2.1 | 300,935 | 187,559 | 1.6 | 7.4 | 108.7 |
| 14 | CAT-5 | C4-A2 | 1200 | 0.010 | 1.8 | — | — | — | — | — |
| 15 | CAT-5 | C4-A2 | 1200 | 0.010 | 1.8 | — | — | — | — | — |
| 16 | CAT-5 | C4-A2 | 1201 | 0.007 | 1.2 | — | — | — | — | — |
| 17 | CAT-6 | DMAH-A1 | 82.4 | 0.071 | 182.5 | 1,050,074 | 544,855 | 1.9 | 9.4 | 110.9 |
| 18 | CAT-6 | DMAH-A1 | 66.0 | 0.071 | 227.8 | 1,141,821 | 501,648 | 2.3 | 8.7 | 111.2 |
| 19 | CAT-6 | DMAH-A1 | 58.3 | 0.064 | 232.5 | 999,770 | 398,292 | 2.5 | 8.9 | 111.1 |
| 20 | CAT-6 | DMAH-A1 | 48.8 | 0.063 | 273.4 | 1,083,362 | 517,622 | 2.1 | 7.8 | 112.2 |
| 21 | CAT-6 | DMAH-A2 | 90.9 | 0.073 | 170.1 | 1,193,672 | 584,419 | 2.0 | 10.9 | 109.5 |
| 22 | CAT-6 | DMAH-A2 | 69.1 | 0.071 | 217.6 | 1,175,287 | 580,789 | 2.0 | 9.5 | 110.2 |
| 23 | CAT-6 | DMAH-A2 | 62.3 | 0.066 | 224.3 | 1,081,252 | 532,293 | 2.0 | 9.1 | 110.4 |
| 24 | CAT-6 | DMAH-A2 | 66.6 | 0.067 | 213.0 | 1,176,921 | 504,728 | 2.3 | 7.6 | 112.6 |
| 25 | CAT-6 | C4-A1 | 62.3 | 0.064 | 217.5 | 1,119,010 | 505,574 | 2.2 | 8.3 | 111.4 |
| 26 | CAT-6 | C4-A1 | 69.4 | 0.065 | 198.3 | 1,150,596 | 556,509 | 2.1 | 8.2 | 111.2 |
| 27 | CAT-6 | C4-A1 | 62.8 | 0.058 | 195.6 | 1,192,220 | 604,433 | 2.0 | 7.4 | 112.2 |
| 28 | CAT-6 | C4-A1 | 63.9 | 0.050 | 165.7 | 1,089,271 | 509,895 | 2.1 | 6.4 | 114.5 |
| 29 | CAT-6 | C4-A2 | 81.3 | 0.072 | 187.5 | 1,093,419 | 526,300 | 2.1 | 9.5 | 110.2 |
| 30 | CAT-6 | C4-A2 | 60.3 | 0.067 | 235.3 | 1,227,052 | 653,494 | 1.9 | 8.1 | 110.5 |
| 31 | CAT-6 | C4-A2 | 62.9 | 0.064 | 215.5 | 1,190,333 | 499,598 | 2.4 | 7.4 | 111.8 |
| 32 | CAT-6 | C4-A2 | 68.3 | 0.061 | 189.1 | 1,101,482 | 513,843 | 2.1 | 7.4 | 112.8 |

Runs 1-16 in Table 13 show the results obtained with catalyst CAT-S. Only a few cells provided enough polymer for full characterization. Generally, polymers of molecular weight 300,000-320,000 g/mol were produced. Octene was incorporated with weight percent ranging from 7.1-8.6 wt %. Melting points ranged from 108.0-109.8° C.

Runs 17-32 in Table 13 shows the results obtained with catalyst CAT-6. This catalyst with C4 activators performed well, producing high molecular weight polymers around 1,000,000-1,100,000 g/mol. Octene incorporation in polymers was similar to those produced by CAT-4, ranging from 6.4-10.9 wt %. The melting points were correspondingly higher due to the higher molecular weights, from 109.5-115.3° C.

Polymerization with Oxadiazole CAT-7 Catalyst and C2 and C4 Activators

Another series of propylene homopolymerization reactions were performed in parallel pressure reactors. In these polymerizations, oxadiazole CAT-7 was used as catalyst with C2 and C4 as activators. Polymerizations were performed at 100° C. and at 160 psi. The data and run conditions are shown in Table 14.

TABLE 14

Data for the propylene homopolymerization with oxadiazole CAT-6 catalyst. General conditions: catalyst = 20 nmol; activator = 22 nmol; solvent = isohexane; total volume = 5 mL; tri(n-octyl)aluminum = 500 nmol; T = 100° C.; P = 160 psi

| Run | Catalyst | Activator | Time (s) | Yield (g) | Activity (kg/ mmol/h) | Mw (g/mol) | Mn (g/mol) | PDI |
|---|---|---|---|---|---|---|---|---|
| 1 | DMAH-A1 | 255 | 0.033 | 23.3 | 591 | 342 | 1.7 | 1 |
| 2 | DMAH-A1 | 178 | 0.030 | 30.3 | 610 | 387 | 1.6 | 2 |
| 3 | DMAH-A1 | 164 | 0.035 | 38.4 | 589 | 363 | 1.6 | 3 |
| 4 | DMAH-A1 | 183 | 0.040 | 39.3 | 573 | 347 | 1.7 | 4 |
| 5 | DMAH-A1 | 157 | 0.034 | 38.9 | 576 | 361 | 1.6 | 5 |
| 6 | DMAH-A1 | 169 | 0.031 | 33.0 | 642 | 360 | 1.8 | 6 |
| 7 | C2-A1 | 244 | 0.041 | 30.2 | 605 | 383 | 1.6 | 7 |
| 8 | C2-A1 | 298 | 0.041 | 24.8 | 623 | 348 | 1.8 | 8 |
| 9 | C2-A1 | 275 | 0.036 | 23.6 | 567 | 349 | 1.6 | 9 |
| 10 | C2-A1 | 1200 | 0.027 | 4.0 | 627 | 372 | 1.7 | 10 |
| 11 | C2-A1 | 989 | 0.032 | 5.8 | 614 | 381 | 1.6 | 11 |

TABLE 14-continued

Data for the propylene homopolymerization with oxadiazole CAT-6 catalyst.
General conditions: catalyst = 20 nmol; activator = 22 nmol; solvent = isohexane; total volume = 5 mL; tri(n-octyl)aluminum = 500 nmol; T = 100° C.; P = 160 psi

| Run | Catalyst | Activator | Time (s) | Yield (g) | Activity (kg/ mmol/h) | Mw (g/mol) | Mn (g/mol) | PDI |
|---|---|---|---|---|---|---|---|---|
| 12 | C2-A1 | 347 | 0.035 | 18.1 | 612 | 364 | 1.7 | 12 |
| 13 | C2-A2 | 364 | 0.041 | 20.3 | 629 | 375 | 1.7 | 13 |
| 14 | C2-A2 | 226 | 0.041 | 32.7 | 623 | 362 | 1.7 | 14 |
| 15 | C2-A2 | 522 | 0.034 | 11.7 | 615 | 344 | 1.8 | 15 |
| 16 | C2-A2 | 1200 | 0.032 | 4.8 | 613 | 354 | 1.7 | 16 |
| 17 | C2-A2 | 368 | 0.038 | 18.6 | 634 | 377 | 1.7 | 17 |
| 18 | C2-A2 | 256 | 0.035 | 24.6 | 659 | 396 | 1.7 | 18 |
| 19 | C4-A1 | 972 | 0.035 | 6.5 | 589 | 352 | 1.7 | 19 |
| 20 | C4-A1 | 1200 | 0.033 | 4.9 | 585 | 364 | 1.6 | 20 |
| 21 | C4-A1 | 834 | 0.033 | 7.1 | 559 | 352 | 1.6 | 21 |
| 22 | C4-A1 | 1201 | 0.028 | 4.2 | 572 | 339 | 1.7 | 22 |
| 23 | C4-A1 | 1022 | 0.032 | 5.6 | 571 | 349 | 1.6 | 23 |
| 24 | C4-A1 | 1152 | 0.030 | 4.7 | 580 | 325 | 1.8 | 24 |
| 25 | C4-A2 | 1200 | 0.013 | 1.9 | 620 | 413 | 1.5 | 25 |
| 26 | C4-A2 | 1200 | 0.013 | 1.9 | 637 | 399 | 1.6 | 26 |
| 27 | C4-A2 | 1201 | 0.012 | 1.8 | 619 | 367 | 1.7 | 27 |
| 28 | C4-A2 | 1202 | 0.011 | 1.6 | 643 | 403 | 1.6 | 28 |
| 29 | C4-A2 | 1201 | 0.011 | 1.6 | 644 | 414 | 1.6 | 29 |
| 30 | C4-A2 | 1201 | 0.015 | 2.2 | 627 | 374 | 1.7 | 30 |

Table 14 shows the results obtained in the propylene homopolymerization using oxadiazole CAT-7 catalyst with C2 and C4 activators. The activity values were very low and replication between cells was poor. Overall, even with the control activators, the catalysts produced low molecular weight oligomers with low activity. Changing the activator did not significantly improve reactivity, or affect the molecular weight of the product. These results agree with those reported by Symyx in PCT/US2005/045766, WO 2006/066126, which showed polypropylene polymers with Mw less than 2,000 g/mol produced under similar conditions.

Polymerization with CAT-8 Catalyst and C2 and C4 Activators

Another series of ethylene-octene copolymerization reactions were performed in parallel pressure reactors. In these polymerizations, CAT-8 was used as catalyst. Polymerizations were performed at 100° C. and at 100 psi. The data and run conditions are shown in Table 1S.

TABLE 15

Data for the ethylene-octene copolymerization with CAT-8 catalyst.
General conditions: catalyst = 20 nmol; activator = 22 nmol; 1-octene = 100 μL; solvent = isohexane; total volume = 5 mL; tri(n-octyl)aluminum = 500 nmol; T = 100° C.; P = 100 psi.

| Run | Activator | Time (s) | Yield (g) | Activity (kg/ mmol/h) | Mw (g/mol) | Mn (g/mol) | PDI | Octene incorporation (wt %) | $T_m$ (° C.) |
|---|---|---|---|---|---|---|---|---|---|
| 1 | DMAH-A1 | 88.6 | 0.052 | 96.0 | 65,521 | 40,626 | 1.6 | 5.6 | 119.5 |
| 2 | DMAH-A1 | 207.3 | 0.045 | 35.5 | 65,906 | 40,107 | 1.6 | 6.6 | 121.7 |
| 3 | DMAH-A1 | 74.7 | 0.053 | 116.1 | 69,359 | 41,667 | 1.7 | 7.3 | 120.4 |
| 4 | DMAH-A1 | 1200 | 0.020 | 2.7 | 66,362 | 43,001 | 1.5 | 4.4 | 123.0 |
| 5 | DMAH-A1 | 1200 | 0.030 | 4.1 | 70,713 | 46,467 | 1.5 | 5.6 | 123.9 |
| 6 | DMAH-A1 | 1201 | 0.004 | 0.5 | | | | | |
| 7 | DMAH-A2 | 33.2 | 0.063 | 310.5 | 70,537 | 41,529 | 1.7 | 8.2 | 116.3 |
| 8 | DMAH-A2 | 30.4 | 0.062 | 333.7 | 71,764 | 50,400 | 1.4 | 6.5 | 116.9 |
| 9 | DMAH-A2 | 34.9 | 0.065 | 304.8 | 70,094 | 42,040 | 1.7 | 6.9 | 117.0 |
| 10 | DMAH-A2 | 48.1 | 0.052 | 176.9 | 69,089 | 41,821 | 1.7 | 7.8 | 117.4 |
| 11 | DMAH-A2 | 54.9 | 0.050 | 149.0 | 64,257 | 32,981 | 1.9 | 8.3 | 117.6 |
| 12 | DMAH-A2 | 48.7 | 0.051 | 171.4 | 70,878 | 43,366 | 1.6 | 4.8 | 118.9 |
| 13 | C4-A1 | 19.5 | 0.066 | 553.8 | 62,952 | 37,369 | 1.7 | 8.0 | 116.5 |
| 14 | C4-A1 | 20.5 | 0.063 | 502.9 | 62,576 | 36,266 | 1.7 | 7.6 | 117.2 |
| 15 | C4-A1 | 21.0 | 0.063 | 490.9 | 66,084 | 41,462 | 1.6 | 5.5 | 118.3 |
| 16 | C4-A1 | 22.1 | 0.064 | 473.9 | 66,794 | 41,821 | 1.6 | 9.5 | 117.3 |
| 17 | C4-A1 | 19.6 | 0.063 | 526.0 | 62,234 | 36,836 | 1.7 | 7.3 | 117.1 |
| 18 | C4-A1 | 21.2 | 0.064 | 494.0 | 62,649 | 38,962 | 1.6 | 7.4 | 118.0 |
| 19 | C4-A2 | 44.0 | 0.058 | 215.7 | 69,451 | 42,221 | 1.6 | 6.3 | 117.8 |
| 20 | C4-A2 | 35.8 | 0.059 | 269.7 | 79,665 | 47,582 | 1.7 | 6.8 | 117.7 |
| 21 | C4-A2 | 36.4 | 0.058 | 260.7 | 71,849 | 48,244 | 1.5 | 6.8 | 118.0 |
| 22 | C4-A2 | 54.5 | 0.054 | 162.1 | 74,949 | 50,289 | 1.5 | 6.6 | 119.0 |
| 23 | C4-A2 | 89.1 | 0.042 | 77.1 | 74,523 | 44,726 | 1.7 | 6.8 | 120.2 |
| 24 | C4-A2 | 107.8 | 0.045 | 68.3 | 72,634 | 46,666 | 1.6 | 6.4 | 119.7 |

The experiments detailed in Table 15 showed an overall decline in activity and replication across the multi-cell experiment. This greatly affected the standard deviation in activity values for each activator, except C4-A1. The activity values for the catalyst system containing the control DMAH-A1 activator were especially low. Polymer molecular weights were generally unaffected by the identity of the borate for the DMAH activator, which produced low molecular weight materials. Molecular weights for these polymers averaged ~67,000 g/mol. However, polymer molecular weights were higher for the C4-A2 and C2-A2 systems (~72,000 g/mol) than the corresponding A1 borates (~65,000 g/mol). Octene incorporation was unaffected by the identity of the borate, with all systems incorporating about the same range of percent octene (~5.5-7.5%). Surprisingly, polymers produced using DMAH-A1 had unusually higher peak melting points (averaging 121.7° C.) than the other polymers produced using A1 activators (averaging 117° C.). This was surprising, given the otherwise similar molecular weights and octene incorporation.

Polymerization with CAT-9 Catalyst and C2 and C4 Activators

Another series of ethylene-octene copolymerization reactions were performed in parallel pressure reactors. In these polymerizations, CAT-9 was used as catalyst. Activators were methylalumoxane (MAO), DMAH-A1, DMAH-A2, C4-A1, C4-A2, C2-A1, and C2-A2. Polymerizations were performed at 100° C. and at 100 psi. The data and run conditions are shown in Tables 16 and 17.

TABLE 16

Data for the ethylene-octene copolymerization with CAT-9 catalyst. General conditions: catalyst = 20 nmol; ammonium borate activator = 22 nmol; MAO activator = 10,000 nmol; 1-octene = 100 μL; solvent = isohexane; total volume = 5 mL; tri(n-octyl)aluminum = 500 nmol; T = 100° C.; P = 100 psi.

| Run | Activator | Time (s) | Yield (g) | Activity (kg/mmol/h) | Mw (g/mol) | Mn (g/mol) | PDI | Octene incorporation (wt %) | $T_m$ (° C.) |
|---|---|---|---|---|---|---|---|---|---|
| 1 | MAO | 27.7 | 0.080 | 519.9 | 137,222 | 82,490 | 1.7 | 12.6 | 104.5 |
| 2 | MAO | 24.1 | 0.086 | 642.3 | 153,088 | 88,608 | 1.7 | 13.7 | 102.8 |
| 3 | MAO | 22.9 | 0.080 | 628.8 | 197,868 | 118,678 | 1.7 | 16.5 | 102.0 |
| 4 | MAO | 22.1 | 0.082 | 667.9 | 214,851 | 126,059 | 1.7 | 16.2 | 102.7 |
| 5 | MAO | 24.3 | 0.078 | 577.8 | 251,989 | 136,153 | 1.9 | 19.2 | 103.4 |
| 6 | MAO | 24.9 | 0.075 | 542.2 | 285,764 | 147,391 | 1.9 | 16.0 | 102.2 |
| 7 | MAO | 26.5 | 0.071 | 482.3 | 279,764 | 158,492 | 1.8 | 17.0 | 102.4 |
| 8 | MAO | 23.3 | 0.073 | 563.9 | 299,068 | 156,605 | 1.9 | 14.2 | 103.7 |
| 9 | DMAH-A1 | 25.4 | 0.094 | 666.1 | 185,671 | 115,979 | 1.6 | 16.8 | 101.5 |
| 10 | DMAH-A1 | 24.4 | 0.096 | 708.2 | 183,632 | 108,835 | 1.7 | 18.2 | 100.7 |
| 11 | DMAH-A1 | 26.1 | 0.092 | 634.5 | 181,796 | 107,001 | 1.7 | 20.6 | 99.7 |
| 12 | DMAH-A1 | 21.9 | 0.091 | 747.9 | 193,041 | 109,550 | 1.8 | 19.6 | 100.4 |
| 13 | DMAH-A1 | 23.8 | 0.082 | 620.2 | 190,935 | 104,604 | 1.8 | 16.1 | 102.2 |
| 14 | DMAH-A1 | 23.2 | 0.086 | 667.2 | 173,719 | 101,604 | 1.7 | 20.8 | 100.5 |
| 15 | DMAH-A1 | 23.2 | 0.085 | 659.5 | 188,323 | 111,696 | 1.7 | 18.4 | 102.3 |
| 16 | DMAH-A2 | 25.3 | 0.086 | 611.9 | 183,011 | 113,350 | 1.6 | 15.8 | 104.7 |
| 17 | DMAH-A2 | 26.8 | 0.080 | 537.3 | 176,446 | 108,125 | 1.6 | 14.5 | 105.5 |
| 18 | DMAH-A2 | 26.1 | 0.084 | 579.3 | 177,123 | 105,434 | 1.7 | 18.0 | 101.0 |
| 19 | DMAH-A2 | 24.8 | 0.080 | 580.6 | 178,785 | 94,468 | 1.9 | 16.6 | 102.5 |
| 20 | DMAH-A2 | 28.9 | 0.064 | 398.6 | 210,426 | 127,596 | 1.6 | 11.0 | 106.6 |
| 21 | DMAH-A2 | 28.0 | 0.081 | 520.7 | 209,419 | 117,579 | 1.8 | 15.7 | 104.0 |
| 22 | DMAH-A2 | 28.7 | 0.079 | 495.5 | 179,927 | 104,304 | 1.7 | 17.6 | 105.8 |
| 23 | DMAH-A2 | 30.4 | 0.071 | 420.4 | 194,397 | 114,177 | 1.7 | 15.2 | 107.9 |
| 24 | C4-A2 | 19.9 | 0.088 | 796.0 | 171,354 | 96,810 | 1.8 | 16.0 | 106.6 |
| 25 | C4-A2 | 21.9 | 0.088 | 723.3 | 180,287 | 105,990 | 1.7 | 20.0 | 106.7 |
| 26 | C4-A2 | 20.8 | 0.087 | 752.9 | 159,906 | 97,909 | 1.6 | 16.3 | 106.0 |
| 27 | C4-A2 | 19.8 | 0.081 | 736.4 | 168,248 | 98,614 | 1.7 | 14.9 | 106.5 |
| 28 | C4-A2 | 19.4 | 0.081 | 751.5 | 163,840 | 94,996 | 1.7 | 20.4 | 105.8 |
| 29 | C4-A2 | 16.5 | 0.078 | 850.9 | 162,455 | 98,737 | 1.6 | 18.0 | 106.2 |
| 30 | C4-A2 | 22.5 | 0.085 | 680.0 | 168,458 | 99,598 | 1.7 | 20.7 | 105.5 |
| 31 | C4-A2 | 20.1 | 0.077 | 689.6 | 183,448 | 111,094 | 1.7 | 17.4 | 108.1 |

In Table 16, runs 24-31 using C4-A2 activator performed with equivalent activities to the control activators MAO and DMAH-A1L and DMAH-A2, with insignificant differences in reactivity between A1/A2 borates. The catalyst/activator systems of runs 9-31 containing borates produced polymers of molecular weights with a much smaller range than the MAO system (runs 1-8). Changing the borate had minimal effect on the molecular weights of the resulting polymers. However, the incorporation of octene was higher for the Al activators, which lowered the melting points of the polymers from the A1 systems.

TABLE 17

Data for the ethylene-octene copolymerization with CAT-9 catalyst. General conditions: catalyst = 20 nmol; ammonium borate activator = 22 nmol; MAO activator = 10,000 nmol; 1-octene = 100 µL; solvent = isohexane; total volume = 5 mL; tri(n-octyl)aluminum = 500 nmol; T = 100° C.; P = 100 psi.

| run | Activator | time (s) | yield (g) | activity (kg/ mmol/h) | Mw (g/mol) | Mn (g/mol) | PDI | Octene incorporation (wt %) | $T_m$ (° C.) |
|---|---|---|---|---|---|---|---|---|---|
| 1 | MAO | 28.3 | 0.079 | 502.5 | 141,791 | 88,319 | 1.6 | 13.2 | 105.2 |
| 2 | MAO | 27.2 | 0.082 | 542.6 | 143,500 | 90,940 | 1.6 | 12.3 | 105.0 |
| 3 | MAO | 28.0 | 0.080 | 514.3 | 157,480 | 89,872 | 1.8 | 13.8 | 104.9 |
| 4 | MAO | 27.3 | 0.071 | 468.1 | 277,796 | 155,589 | 1.8 | 13.9 | 103.0 |
| 5 | MAO | 27.4 | 0.072 | 473.0 | 278,037 | 148,218 | 1.9 | 12.2 | 103.6 |
| 6 | MAO | 26.9 | 0.074 | 495.2 | 283,318 | 162,846 | 1.7 | 13.1 | 103.9 |
| 7 | DMAH-A1 | 25.1 | 0.090 | 645.4 | 182,185 | 114,533 | 1.6 | 19.6 | 100.8 |
| 8 | DMAH-A1 | 20.6 | 0.096 | 838.8 | 177,239 | 92,882 | 1.9 | 18.5 | 102.2 |
| 9 | DMAH-A1 | 24.1 | 0.090 | 672.2 | 181,536 | 109,924 | 1.7 | 19.1 | 100.4 |
| 10 | DMAH-A1 | 24.5 | 0.079 | 580.4 | 153,296 | 94,401 | 1.6 | 17.8 | 101.4 |
| 11 | DMAH-A1 | 24.6 | 0.085 | 622.0 | 167,008 | 98,681 | 1.7 | 18.1 | 100.4 |
| 12 | DMAH-A1 | 287.8 | 0.041 | 25.6 | 178,420 | 104,636 | 1.7 | 9.6 | 109.2 |
| 13 | DMAH-A2 | 30.3 | 0.069 | 409.9 | 188,065 | 116,818 | 1.6 | 14.9 | 106.7 |
| 14 | DMAH-A2 | 28.2 | 0.085 | 542.6 | 182,239 | 107,008 | 1.7 | 16.2 | 105.7 |
| 15 | DMAH-A2 | 25.2 | 0.085 | 607.1 | 182,218 | 101,783 | 1.8 | 16.6 | 103.7 |
| 16 | DMAH-A2 | 21.5 | 0.077 | 644.7 | 166,544 | 104,000 | 1.6 | 17.0 | 104.9 |
| 17 | DMAH-A2 | 25.7 | 0.080 | 560.3 | 170,020 | 104,777 | 1.6 | 15.4 | 105.5 |
| 18 | DMAH-A2 | 28.0 | 0.082 | 527.1 | 167,106 | 97,856 | 1.7 | 16.4 | 105.3 |
| 19 | C2-A1 | 22.4 | 0.094 | 755.4 | 183,600 | 116,398 | 1.6 | 17.5 | 101.6 |
| 20 | C2-A1 | 21.9 | 0.089 | 731.5 | 189,770 | 102,639 | 1.8 | 20.1 | 102.0 |
| 21 | C2-A1 | 23.6 | 0.087 | 663.6 | 186,343 | 118,461 | 1.6 | 21.5 | 99.4 |
| 22 | C2-A1 | 22.6 | 0.082 | 653.1 | 162,200 | 87,814 | 1.8 | 17.5 | 103.6 |
| 23 | C2-A1 | 21.0 | 0.087 | 745.7 | 168,417 | 87,955 | 1.9 | 17.4 | 101.9 |
| 24 | C2-A1 | 21.1 | 0.093 | 793.4 | 171,511 | 100,073 | 1.7 | 16.8 | 103.0 |
| 25 | C2-A2 | 21.1 | 0.082 | 699.5 | 154,174 | 89,771 | 1.7 | 17.8 | 105.7 |
| 26 | C2-A2 | 22.6 | 0.083 | 661.1 | 153,748 | 92,403 | 1.7 | 16.6 | 106.0 |
| 27 | C2-A2 | 21.2 | 0.082 | 696.2 | 167,135 | 101,134 | 1.7 | 18.2 | 108.0 |
| 28 | C2-A2 | 21.7 | 0.076 | 630.4 | 190,016 | 116,530 | 1.6 | 14.3 | 104.0 |
| 29 | C2-A2 | 21.3 | 0.080 | 676.1 | 183,426 | 109,296 | 1.7 | 18.4 | 105.8 |
| 30 | C2-A2 | 23.3 | 0.082 | 633.5 | 191,075 | 109,856 | 1.7 | 17.2 | 104.8 |
| 31 | C4-A1 | 23.3 | 0.089 | 687.6 | 166,163 | 91,232 | 1.8 | 17.6 | 101.7 |
| 32 | C4-A1 | 23.0 | 0.094 | 735.7 | 174,433 | 100,477 | 1.7 | 18.6 | 103.2 |
| 33 | C4-A1 | 22.0 | 0.093 | 760.9 | 182,345 | 101,181 | 1.8 | 16.0 | 102.9 |
| 34 | C4-A1 | 32.4 | 0.061 | 338.9 | 232,555 | 145,685 | 1.6 | 13.4 | 101.0 |
| 35 | C4-A1 | 23.2 | 0.086 | 667.2 | 199,807 | 119,361 | 1.7 | 19.9 | 99.7 |
| 36 | C4-A1 | 22.3 | 0.086 | 694.2 | 206,898 | 123,436 | 1.7 | 20.8 | 101.9 |
| 37 | C4-A2 | 21.5 | 0.085 | 711.6 | 152,838 | 82,692 | 1.8 | 15.2 | 107.7 |
| 38 | C4-A2 | 20.8 | 0.085 | 735.6 | 168,480 | 101,539 | 1.7 | 15.2 | 108.4 |
| 39 | C4-A2 | 25.2 | 0.079 | 564.3 | 168,864 | 101,634 | 1.7 | 15.4 | 107.5 |
| 40 | C4-A2 | 18.8 | 0.079 | 756.4 | 202,778 | 120,099 | 1.7 | 15.9 | 106.0 |
| 41 | C4-A2 | 22.6 | 0.076 | 605.3 | 188,942 | 113,000 | 1.7 | 16.0 | 105.5 |
| 42 | C4-A2 | 23.5 | 0.074 | 566.8 | 185,108 | 107,245 | 1.7 | 14.7 | 105.2 |
| 43 | C4-A2 | 27.5 | 0.094 | 615.3 | 175,350 | 105,141 | 1.7 | 14.8 | 108.7 |
| 44 | C4-A2 | 21.4 | 0.085 | 715.0 | 159,252 | 101,457 | 1.6 | 16.0 | 108.2 |
| 45 | C4-A2 | 22.8 | 0.072 | 568.4 | 197,532 | 120,218 | 1.6 | 15.2 | 108.0 |
| 46 | C4-A2 | 74.7 | 0.041 | 98.8 | 201,514 | 123,869 | 1.6 | 8.6 | 110.2 |
| 47 | C4-A2 | 21.8 | 0.078 | 644.0 | 188,688 | 103,390 | 1.8 | 15.8 | 106.8 |

As shown in runs 19-47 of Table 17, C4-A1/A2, and C2-A1/A2 activators performed well, with equivalent or higher activity to the control MAO and DMAH-A1/A2 activators. The polymers produced by the ammonium borate activator systems had very narrow molecular weight distribution. Similarly to the results of Table 13, the polymers produced by MAO have a very large range in molecular weight. The polymer molecular weights were not affected by the change in borate between A1 and A2. The incorporation of octene is affected by the borate, with A1 activators yielding polymer with slightly higher % octene (16-21%) versus the polymers made using A2 activators (15-18%). Correspondingly, the polymers with higher percent octene had lower peak melting points. The two batches of C4-A2 appeared to be equivalent in terms of activity and polymers produced.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

The invention claimed is:

1. A compound represented by Formula (I):

$$[Ar(EHR^1R^2)\ (OR^3)]_d^+[M^{k+}Q_n]^{d-} \quad (I)$$

wherein:

Ar is a phenyl group;

E is nitrogen or phosphorous;

$R^1$ is a $C_1$-$C_{30}$, unsubstituted linear alkyl group;

$R^2$ is a $C_1$-$C_{30}$, unsubstituted linear alkyl group;

$R^3$ is a $C_{10}$-$C_{30}$, unsubstituted linear alkyl group;

M is boron or aluminum;

d is 1, 2 or 3; k is 1, 2, or 3; n is 2, 3, 4, 5, or 6; n-k=d; and each Q is a perfluorophenyl, a perchlorophenyl, a perfluoronapthyl, or a perchloronapthyl.

2. The compound of claim 1, wherein $R^1$ is a $C_1$ to $C_{10}$ linear alkyl group.

3. The compound of claim 1, wherein $R^1$ is methyl, ethyl, propyl, butyl, pentyl, or hexyl.

4. The compound of claim 1, wherein $R^2$ is a $C_1$-$C_{20}$, optionally substituted, linear alkyl group.

5. The compound of claim 1, wherein $R^1$ is methyl.

6. The compound of claim 1, wherein $R^2$ is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

7. The compound of claim 1, wherein $R^3$ is n-decyl, n-undecyl, n-dodecyl, n-tridecyl, n-tetradecyl, n-pentadecyl, n-hexadecyl, n-heptadecyl, n-octadecyl, n-nonadecyl, or n-icosyl.

8. The compound of claim 1, wherein E is nitrogen.

9. The compound of claim 1, wherein M is boron and k is 3.

10. The compound of claim 1, wherein Q is the perfluorophenyl.

11. The compound of claim 1, wherein $R^1$, $R^2$, and $R^3$ together comprise 20 or more carbon atoms.

12. The compound of claim 1, wherein E is phosphorous.

13. The compound of claim 1, wherein the compound has a solubility of at least 10 mM at 25° C. in methylcyclohexane.

14. The compound of claim 1, wherein the compound has a solubility of at least 10 mM at 25° C. in isohexane.

15. The compound of claim 1, wherein the compound has a solubility of at least 10 mM at 25° C. in methylcyclohexane and a solubility of at least 10 mM at 25° C. in isohexane.

16. A catalyst system comprising a catalyst and an activator comprising the compound of claim 1.

17. The catalyst system of claim 16, further comprising a support material.

18. A solution comprising the compound of claim 1 and an aliphatic solvent; wherein aromatic solvents are absent.

19. A solution comprising the catalyst system of claim 16 and an aliphatic solvent; wherein aromatic solvents are absent.

* * * * *